US008986373B2

(12) United States Patent
Chau et al.

(10) Patent No.: US 8,986,373 B2
(45) Date of Patent: *Mar. 24, 2015

(54) METHOD FOR IMPLANTING A PROSTHETIC MITRAL VALVE

(71) Applicant: Edwards Lifesciences Corporation, Irvine, CA (US)

(72) Inventors: Mark Chau, Aliso Viejo, CA (US); Marlowe E. Patterson, Orange, CA (US); Seung-Beom Yi, Mission Viejo, CA (US); Stephen C. Geist, Costa Mesa, CA (US); Travis Oba, Brea, CA (US); David L. Hauser, Newport Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/025,701

(22) Filed: Sep. 12, 2013

(65) Prior Publication Data

US 2014/0012373 A1 Jan. 9, 2014

Related U.S. Application Data

(63) Continuation of application No. 13/597,122, filed on Aug. 28, 2012, now Pat. No. 8,585,755, which is a continuation of application No. 12/959,292, filed on Dec. 2, 2010, now Pat. No. 8,449,599.

(60) Provisional application No. 61/266,774, filed on Dec. 4, 2009, provisional application No. 61/287,099, filed on Dec. 16, 2009.

(51) Int. Cl.
A61F 2/24 (2006.01)
A61F 11/00 (2006.01)

(52) U.S. Cl.
CPC ............ *A61F 2/2409* (2013.01); *A61F 2/2418* (2013.01); *A61F 2/2445* (2013.01);

(Continued)

(58) Field of Classification Search
CPC ................................. A61F 2/2418; A61F 2/06
USPC ................. 623/1.24, 1.26, 2.1–2.19; 606/108
See application file for complete search history.

(56) References Cited

U.S. PATENT DOCUMENTS 3,409,013 A 11/1968 Berry
3,472,230 A 10/1969 Fogarty et al.
(Continued)

FOREIGN PATENT DOCUMENTS

DE 2246526 3/1973
DE 19532846 3/1997
(Continued)

OTHER PUBLICATIONS

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

(Continued)

*Primary Examiner* — Jason-Dennis Stewart
(74) *Attorney, Agent, or Firm* — David L. Hauser; Klarquist Sparkman, LLP

(57) ABSTRACT

Embodiments of a method for implanting a prosthetic valve at the native mitral valve region of the heart, the prosthetic valve including a main body that is radially compressible to a radially compressed state and self-expandable from the compressed state to a radially expanded state. The prosthetic apparatus also comprises at least one ventricular anchor coupled to the main body and disposed outside of the main body with a leaflet-receiving space between the anchor and an outer surface of the main body to receive a native valve leaflet. Apparatus for delivering and implanting the prosthetic valve are also described.

15 Claims, 40 Drawing Sheets

(52) U.S. Cl.
CPC ......... *A61F2220/0008* (2013.01); *A61F 2/246* (2013.01); *A61F 2250/006* (2013.01); *A61F 2/2412* (2013.01)
USPC ........... 623/2.17; 623/2.1; 623/2.18; 606/108

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,108,370 A | 4/1992 | Walinsky |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,232,446 A | 8/1993 | Arney |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane et al. |
| 5,411,522 A | 5/1995 | Trott |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely |
| 5,554,185 A | 9/1996 | Block et al. |
| 5,571,175 A | 11/1996 | Vanney et al. |
| 5,591,185 A | 1/1997 | Kilmer et al. |
| 5,599,305 A | 2/1997 | Hermann et al. |
| 5,607,464 A | 3/1997 | Trescony et al. |
| 5,609,626 A | 3/1997 | Quijano et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,906,619 A | 5/1999 | Olson et al. |
| 5,925,063 A | 7/1999 | Khosravi |
| 5,957,949 A | 9/1999 | Leonhardt et al. |
| 5,968,068 A | 10/1999 | Dehdashtian et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,171,335 B1 | 1/2001 | Wheatley et al. |
| 6,174,327 B1 | 1/2001 | Mertens et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,040 B1 | 6/2001 | Inderbitzen |
| 6,245,102 B1 | 6/2001 | Jayaraman |
| 6,287,339 B1 | 9/2001 | Vazquez et al. |
| 6,299,637 B1 | 10/2001 | Shaolian |
| 6,302,906 B1 | 10/2001 | Goecoechea et al. |
| 6,306,141 B1 | 10/2001 | Jervis |
| 6,312,465 B1 | 11/2001 | Griffin et al. |
| 6,350,277 B1 | 2/2002 | Kocur |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,527,979 B2 | 3/2003 | Constantz |
| 6,569,196 B1 | 5/2003 | Vesely et al. |
| 6,582,462 B1 | 6/2003 | Andersen et al. |
| 6,605,112 B1 | 8/2003 | Moll |
| 6,730,118 B2 | 5/2004 | Spenser et al. |
| 6,733,525 B2 | 5/2004 | Yang et al. |
| 6,790,229 B1 | 9/2004 | Berreklouw |
| 6,830,584 B1 | 12/2004 | Seguin |
| 6,893,460 B2 | 5/2005 | Spenser et al. |
| 6,908,481 B2 | 6/2005 | Cribier |
| 6,974,476 B2 | 12/2005 | McGuckin et al. |
| 7,018,406 B2 | 3/2006 | Seguin et al. |
| 7,018,408 B2 | 3/2006 | Bailey et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,381,210 B2 | 6/2008 | Zarbatany et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |

(56) References Cited

U.S. PATENT DOCUMENTS

| | | | |
|---|---|---|---|
| 7,462,191 B2 | 12/2008 | Spenser et al. | |
| 7,510,575 B2 | 3/2009 | Spenser et al. | |
| 7,524,330 B2 | 4/2009 | Berreklouw | |
| 7,530,253 B2 | 5/2009 | Spenser | |
| 7,579,381 B2 | 8/2009 | Dove | |
| 7,585,321 B2 | 9/2009 | Cribier | |
| 7,618,446 B2 | 11/2009 | Andersen et al. | |
| 7,621,948 B2 | 11/2009 | Herrmann | |
| 7,704,222 B2 | 4/2010 | Wilk et al. | |
| 7,736,327 B2 | 6/2010 | Wilk et al. | |
| 7,892,281 B2 | 2/2011 | Seguin et al. | |
| 7,914,575 B2 | 3/2011 | Guyenot et al. | |
| 7,993,394 B2 | 8/2011 | Hariton et al. | |
| 8,007,992 B2 | 8/2011 | Tian et al. | |
| 8,029,556 B2 | 10/2011 | Rowe | |
| 8,092,521 B2 | 1/2012 | Figulla et al. | |
| 8,118,866 B2 | 2/2012 | Herrmann et al. | |
| 8,167,932 B2 | 5/2012 | Bourang | |
| 8,206,437 B2 | 6/2012 | Bonhoeffer et al. | |
| 8,216,174 B2 | 7/2012 | Wilk et al. | |
| 8,317,858 B2 | 11/2012 | Straubinger et al. | |
| 8,398,704 B2 | 3/2013 | Straubinger et al. | |
| 8,407,380 B2 | 3/2013 | Matsunaga | |
| 8,416,643 B2 | 4/2013 | Magee | |
| 8,449,599 B2 | 5/2013 | Chau | |
| 2001/0021872 A1 | 9/2001 | Bailey et al. | |
| 2002/0032481 A1 | 3/2002 | Gabbay | |
| 2002/0173842 A1 | 11/2002 | Buchanan | |
| 2003/0050694 A1 | 3/2003 | Yang et al. | |
| 2003/0100939 A1 | 5/2003 | Yodfat et al. | |
| 2003/0158597 A1 | 8/2003 | Quiachon | |
| 2003/0212454 A1 | 11/2003 | Scott et al. | |
| 2004/0039436 A1 | 2/2004 | Spenser et al. | |
| 2004/0092858 A1 | 5/2004 | Wilson et al. | |
| 2004/0133263 A1 | 7/2004 | Dusbabek et al. | |
| 2004/0186563 A1 | 9/2004 | Lobbi | |
| 2004/0186565 A1 | 9/2004 | Schreck | |
| 2004/0260389 A1 | 12/2004 | Case et al. | |
| 2005/0137688 A1 | 6/2005 | Salahieh et al. | |
| 2005/0137695 A1 | 6/2005 | Salahieh et al. | |
| 2005/0137698 A1 | 6/2005 | Salahieh et al. | |
| 2005/0203614 A1 | 9/2005 | Forster et al. | |
| 2005/0203617 A1 | 9/2005 | Forster et al. | |
| 2005/0234546 A1 | 10/2005 | Nugent et al. | |
| 2005/0288766 A1 | 12/2005 | Plain et al. | |
| 2006/0025857 A1 | 2/2006 | Bergheim et al. | |
| 2006/0058872 A1 | 3/2006 | Salahieh et al. | |
| 2006/0142837 A1 | 6/2006 | Haverkost et al. | |
| 2006/0149350 A1 | 7/2006 | Patel et al. | |
| 2006/0161249 A1 | 7/2006 | Realyvasquez et al. | |
| 2006/0195134 A1 | 8/2006 | Crittenden | |
| 2006/0229719 A1 | 10/2006 | Marquez et al. | |
| 2006/0241745 A1 | 10/2006 | Solem | |
| 2006/0259135 A1 | 11/2006 | Navia et al. | |
| 2006/0259137 A1 | 11/2006 | Artof et al. | |
| 2006/0276874 A1 | 12/2006 | Wilson et al. | |
| 2007/0005131 A1 | 1/2007 | Taylor | |
| 2007/0005231 A1 | 1/2007 | Seguchi | |
| 2007/0010877 A1 | 1/2007 | Salahieh et al. | |
| 2007/0016286 A1* | 1/2007 | Herrmann et al. | 623/2.11 |
| 2007/0027534 A1 | 2/2007 | Bergeim et al. | |
| 2007/0088431 A1 | 4/2007 | Bourang et al. | |
| 2007/0100439 A1 | 5/2007 | Cangialosi et al. | |
| 2007/0100440 A1* | 5/2007 | Figulla et al. | 623/2.18 |
| 2007/0112422 A1 | 5/2007 | Dehdashtian | |
| 2007/0142906 A1 | 6/2007 | Figulla et al. | |
| 2007/0203503 A1 | 8/2007 | Salahieh et al. | |
| 2007/0203575 A1 | 8/2007 | Forster et al. | |
| 2007/0213813 A1 | 9/2007 | Von Segesser et al. | |
| 2007/0270943 A1 | 11/2007 | Solem | |
| 2008/0065011 A1 | 3/2008 | Marchand et al. | |
| 2008/0071361 A1 | 3/2008 | Tuval et al. | |
| 2008/0071362 A1 | 3/2008 | Tuval et al. | |
| 2008/0071363 A1 | 3/2008 | Tuval et al. | |
| 2008/0071366 A1 | 3/2008 | Tuval et al. | |
| 2008/0071368 A1 | 3/2008 | Tuval et al. |
| 2008/0071369 A1 | 3/2008 | Tuval et al. |
| 2008/0082166 A1 | 4/2008 | Styrc et al. |
| 2008/0114442 A1 | 5/2008 | Mitchell et al. |
| 2008/0125853 A1 | 5/2008 | Bailey et al. |
| 2008/0154355 A1 | 6/2008 | Benichou et al. |
| 2008/0161911 A1 | 7/2008 | Revuelta et al. |
| 2008/0177381 A1 | 7/2008 | Navia et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0255660 A1 | 10/2008 | Guyenot et al. |
| 2008/0255661 A1 | 10/2008 | Straubinger et al. |
| 2008/0281411 A1 | 11/2008 | Berreklouw |
| 2009/0005863 A1 | 1/2009 | Goetz et al. |
| 2009/0054968 A1 | 2/2009 | Bonhoeffer et al. |
| 2009/0054974 A1 | 2/2009 | McGuckin, Jr. et al. |
| 2009/0076598 A1 | 3/2009 | Salahieh et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0164005 A1 | 6/2009 | Dove et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0216310 A1 | 8/2009 | Straubinger et al. |
| 2009/0216313 A1 | 8/2009 | Straubinger et al. |
| 2009/0216322 A1 | 8/2009 | Le et al. |
| 2009/0222076 A1 | 9/2009 | Figulla et al. |
| 2009/0234443 A1 | 9/2009 | Ottma et al. |
| 2009/0240320 A1 | 9/2009 | Tuval et al. |
| 2009/0276040 A1 | 11/2009 | Rowe et al. |
| 2009/0281619 A1 | 11/2009 | Le et al. |
| 2009/0287299 A1 | 11/2009 | Tabor et al. |
| 2009/0319037 A1 | 12/2009 | Rowe et al. |
| 2010/0016958 A1 | 1/2010 | St. Goar et al. |
| 2010/0049313 A1 | 2/2010 | Alon et al. |
| 2010/0131054 A1 | 5/2010 | Tuval et al. |
| 2010/0137979 A1 | 6/2010 | Tuval et al. |
| 2010/0174362 A1 | 7/2010 | Straubinger et al. |
| 2010/0204781 A1 | 8/2010 | Alkhatib |
| 2010/0217382 A1 | 8/2010 | Chau et al. |
| 2010/0262231 A1 | 10/2010 | Tuval et al. |
| 2011/0015616 A1 | 1/2011 | Straubinger et al. |
| 2011/0015729 A1 | 1/2011 | Jimenez et al. |
| 2011/0137397 A1 | 6/2011 | Chau et al. |
| 2011/0208290 A1 | 8/2011 | Straubinger et al. |
| 2011/0208297 A1 | 8/2011 | Tuval et al. |
| 2011/0208298 A1 | 8/2011 | Tuval et al. |
| 2011/0238159 A1 | 9/2011 | Guyenot et al. |
| 2011/0288634 A1 | 11/2011 | Tuval et al. |
| 2011/0319989 A1 | 12/2011 | Lane et al. |
| 2012/0035722 A1 | 2/2012 | Tuval et al. |
| 2012/0046741 A1 | 2/2012 | Tuval et al. |
| 2012/0046742 A1 | 2/2012 | Tuval et al. |
| 2012/0101570 A1 | 4/2012 | Tuval et al. |
| 2012/0123529 A1 | 5/2012 | Levi et al. |
| 2012/0185039 A1 | 7/2012 | Tuval et al. |
| 2012/0197386 A1 | 8/2012 | Von Segesser et al. |
| 2012/0209374 A1 | 8/2012 | Bonhoeffer et al. |
| 2012/0283823 A1 | 11/2012 | Bonhoeffer et al. |
| 2012/0310336 A1 | 12/2012 | Figulla et al. |
| 2013/0073035 A1 | 3/2013 | Tuval et al. |
| 2013/0079869 A1 | 3/2013 | Straubinger et al. |

FOREIGN PATENT DOCUMENTS

| | | |
|---|---|---|
| DE | 19546692 | 6/1997 |
| DE | 19857887 | 7/2000 |
| DE | 19907646 | 8/2000 |
| DE | 10010074 | 10/2001 |
| DE | 10049812 | 4/2002 |
| DE | 10049813 | 4/2002 |
| DE | 10049814 | 4/2002 |
| DE | 10049815 | 4/2002 |
| DE | 102006052564 | 12/2007 |
| EP | 0103546 | 3/1984 |
| EP | 0144167 | 6/1985 |
| EP | 0597967 | 12/1994 |

(56) References Cited

FOREIGN PATENT DOCUMENTS

| | | |
|---|---|---|
| EP | 0592410 | 10/1995 |
| EP | 0850607 | 7/1998 |
| EP | 1057460 | 12/2000 |
| EP | 1088529 | 4/2001 |
| EP | 1469797 | 10/2004 |
| EP | 1570809 | 9/2005 |
| EP | 1653888 | 5/2006 |
| FR | 2815844 | 5/2002 |
| FR | 2788217 | 7/2007 |
| GB | 2056023 | 3/1981 |
| SU | 1271508 | 11/1986 |
| WO | WO 91/17720 | 11/1991 |
| WO | WO 92/17118 | 10/1992 |
| WO | WO 93/01768 | 2/1993 |
| WO | WO 97/24080 | 7/1997 |
| WO | WO 98/29057 | 7/1998 |
| WO | WO 99/33414 | 7/1999 |
| WO | WO 99/40964 | 8/1999 |
| WO | WO 99/47075 | 9/1999 |
| WO | WO 00/18333 | 4/2000 |
| WO | WO 00/41652 | 7/2000 |
| WO | WO 00/47139 | 8/2000 |
| WO | WO 01/28459 | 4/2001 |
| WO | WO 01/35878 | 5/2001 |
| WO | WO 01/49213 | 7/2001 |
| WO | WO 01/54624 | 8/2001 |
| WO | WO 01/54625 | 8/2001 |
| WO | WO 01/62189 | 8/2001 |
| WO | WO 01/64137 | 9/2001 |
| WO | WO 01/76510 | 10/2001 |
| WO | WO 02/22054 | 3/2002 |
| WO | WO 02/36048 | 5/2002 |
| WO | WO 02/41789 | 5/2002 |
| WO | WO 02/43620 | 6/2002 |
| WO | WO 02/47575 | 6/2002 |
| WO | WO 02/49540 | 6/2002 |
| WO | WO 03/047468 | 6/2003 |
| WO | WO 2005/034812 | 4/2005 |
| WO | WO 2005/087140 | 9/2005 |
| WO | WO 2005/102015 | 11/2005 |
| WO | WO 2006/014233 | 2/2006 |
| WO | WO 2006/034008 | 3/2006 |
| WO | 2006113906 A1 | 10/2006 |
| WO | WO 2006/108090 | 10/2006 |
| WO | WO 2006/111391 | 10/2006 |
| WO | WO 2006/138173 | 12/2006 |
| WO | WO 2008/005405 | 1/2008 |
| WO | WO 2008/035337 | 3/2008 |
| WO | WO 2008/147964 | 12/2008 |
| WO | WO 2008/150529 | 12/2008 |
| WO | WO 2009/024859 | 2/2009 |
| WO | WO 2009/116041 | 9/2009 |

OTHER PUBLICATIONS

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.
Al Zaibag, Muayed, et al., "Percutaneous Balloon Valvotomy in Tricuspid Stenosis," British Heart Journal, Jan. 1987, vol. 57, No. 1, pp. 51-53.
Andersen, et al., "Transluminal implantation of artificial heart valves. Description of a new expandable aortic valve and initial results with implantation by catheter technique in closed chest pigs." European Heart Journal (1992), 13, 704-708.
Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.
Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.
Dake, Transluminal Placement of Endovascular Stent-Grafts for the Treatment of Descending Thoracic Aortic Aneurysms, New Engl.J. Med., 1994; 331:1729-34.
Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.
Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.
Inoune, M.D., Kanji, et al., "Clinical Application of Transvenous Mitral Commissurotomy by a New Balloon Catheter," The Journal of Thoracic and Cardiovascular Surgery 87:394-402, 1984.
Lawrence, Jr., M.D., David D., "Percutaneous Endovascular Graft: Experimental Evaluation," Radiology 1897; 163: 357-360.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.
Rashkind, M.D., William J., "Creation of an Atrial Septal Defect Withoput Thoracotomy," the Journal of the American Medical Association, vol. 196, No. 11, Jun. 13, 1966, pp. 173-174.
Rashkind, M.D., William J., "Historical Aspects of Interventional Cardiology: Past, Present, Future," Texas Heart Institute Journal, Interventional Cardiology, pp. 363-367.
Rösch, M.D., Josef, "The Birth, Early Years and Future of Interventional Radiology," J Vasc Interv Radiol 2003; 14:841-853.
Ross, F.R.C.S., D.N., "Aortic Valve Surgery," Guy's Hospital, London, pp. 192-197, approximately 1968.
Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.
Selby, M.D., J. Bayne, "Experience with New Retrieval Forceps for Foreign Body Removal in the Vascular, Urinary, and Biliary Systems," Radiology 1990; 176:535-538.
Serruys, P.W., et al., "Stenting of Coronary Arteries. Are we the Sorcerer's Apprentice?," European Heart Journal (1989) 10, 774-782, pp. 37-45, Jun. 13, 1989.
Sigwart, Ulrich, "An Overview of Intravascular Stents: Old and New," Chapter 48, Textbook of Interventional Cardiology, $2^{nd}$ Edition, W.B. Saunders Company, Philadelphia, PA, © 1994, 1990, pp. 803-815.
Uchida, Barry T., et al., "Modifications of Gianturco Expandable Wire Stents," AJR:150, May 1988, Dec. 3, 1987, pp. 1185-1187.
Urban, M.D., Philip, "Coronary Artery Stenting," Editions Médecine et Hygiéne, Genéve, 1991, pp. 5-47.
Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.
Wheatley, M.D., David J., "Valve Prostheses," Rob & Smith's Operative Surgery, Fourth Edition, pp. 415-424, Butterworths 1986.

* cited by examiner

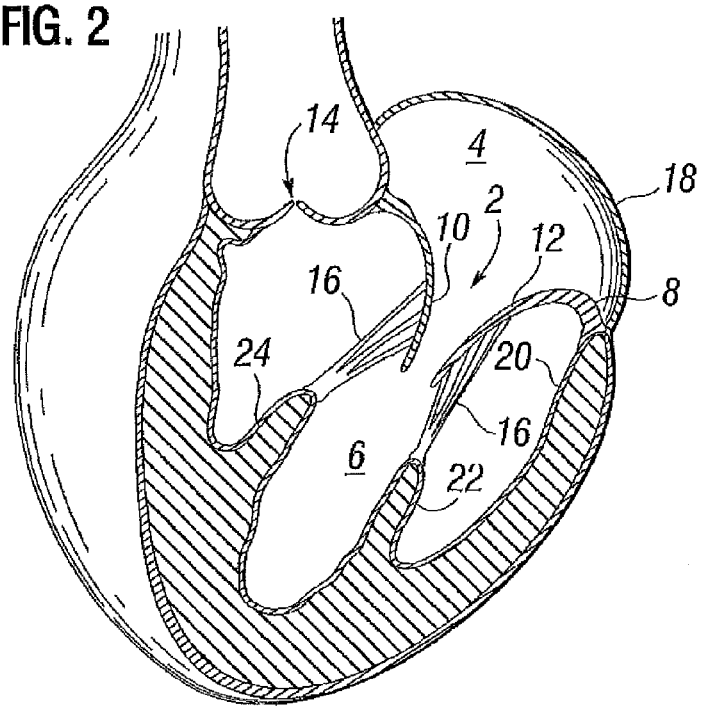
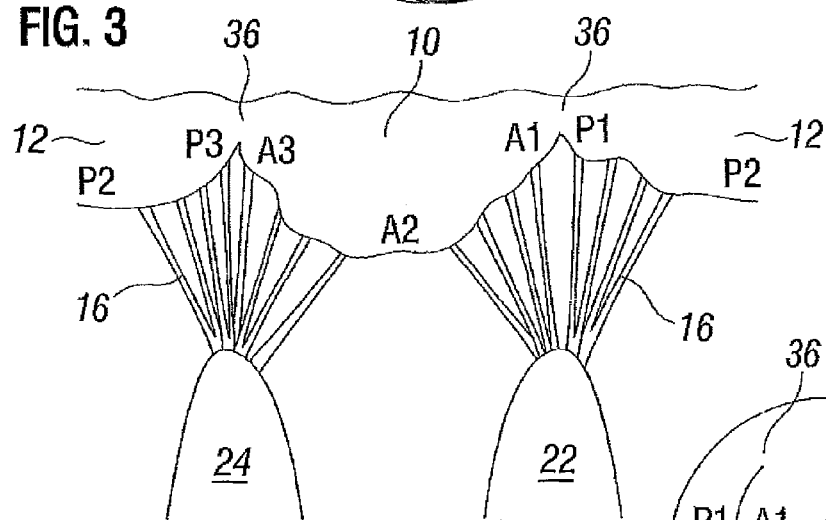
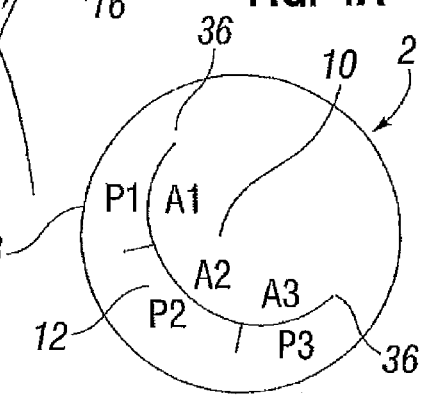

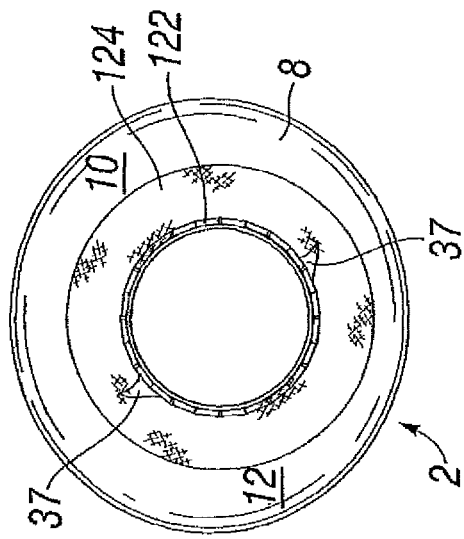
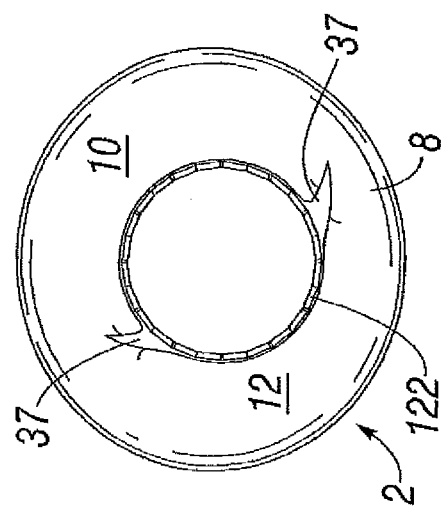
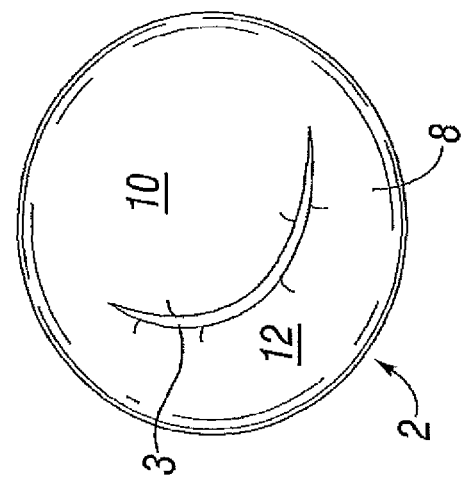

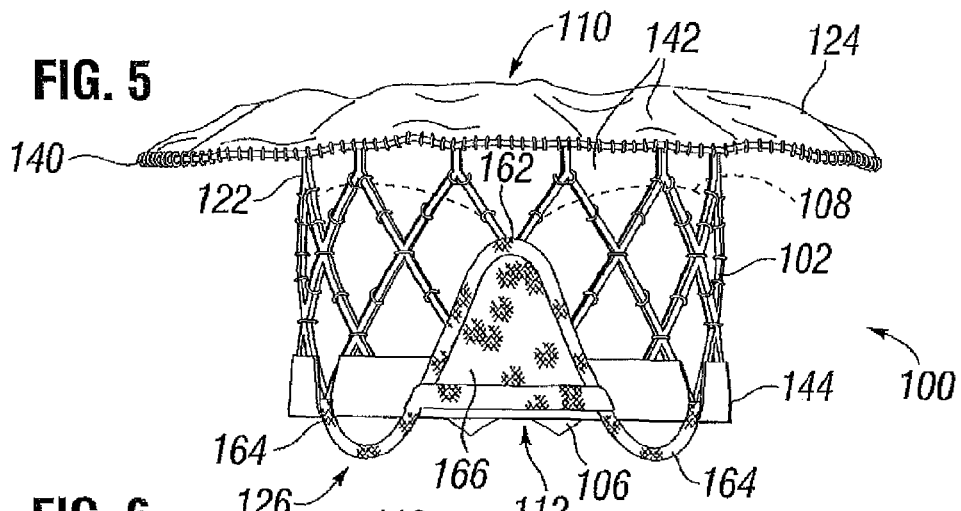
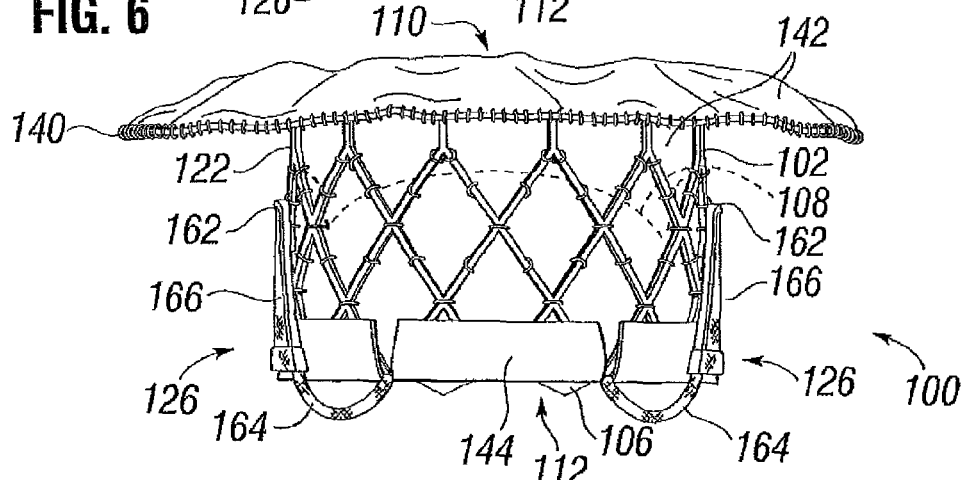
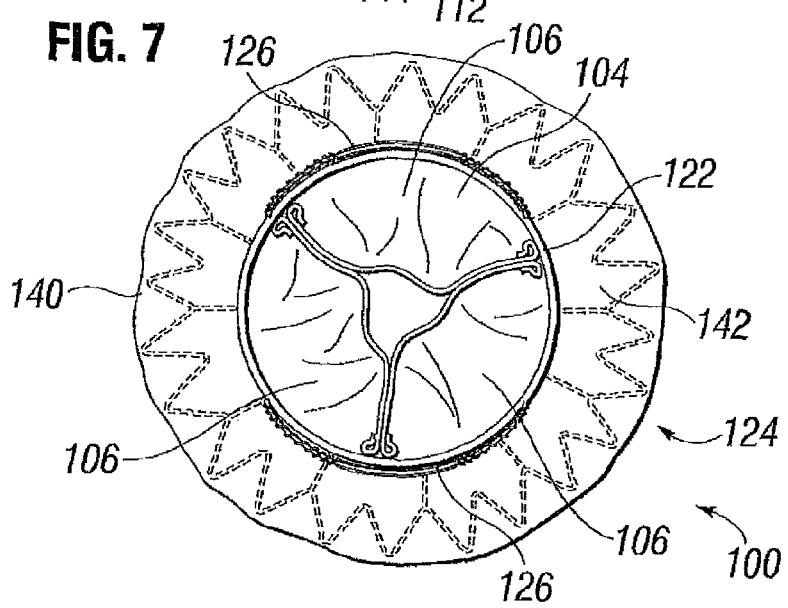

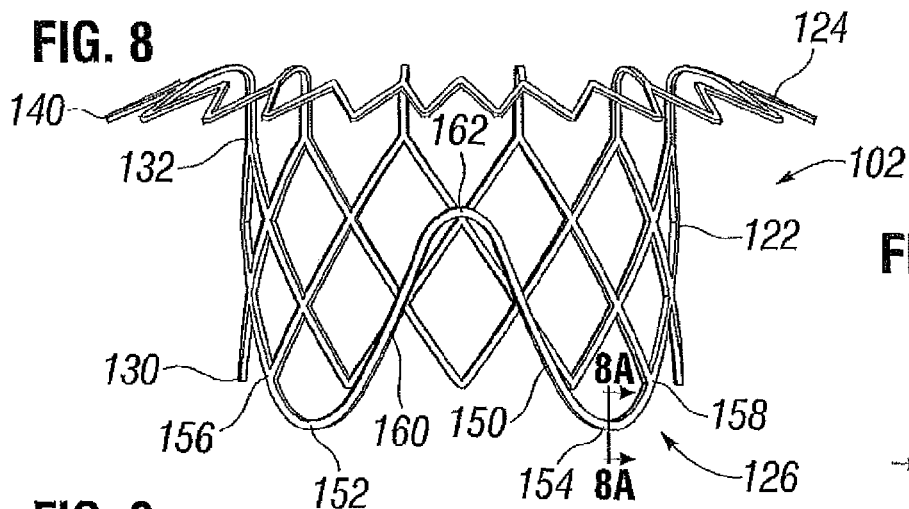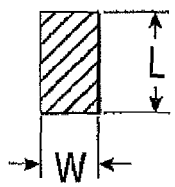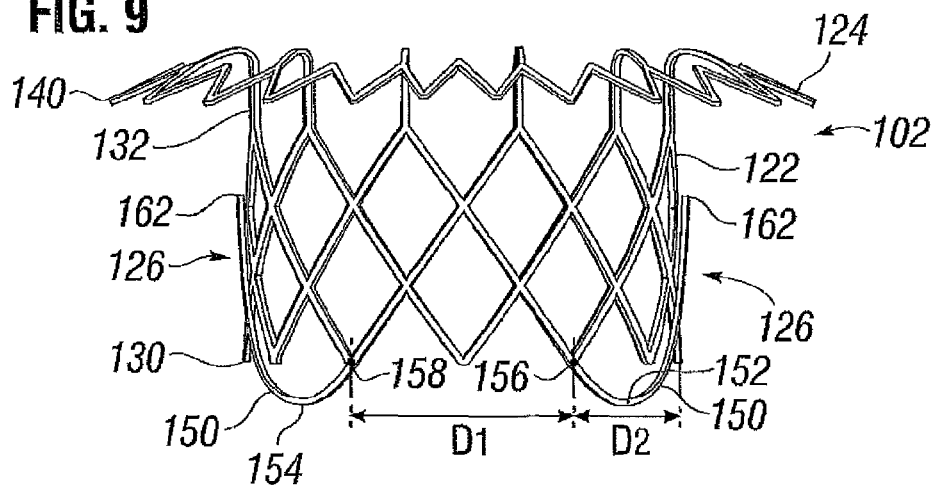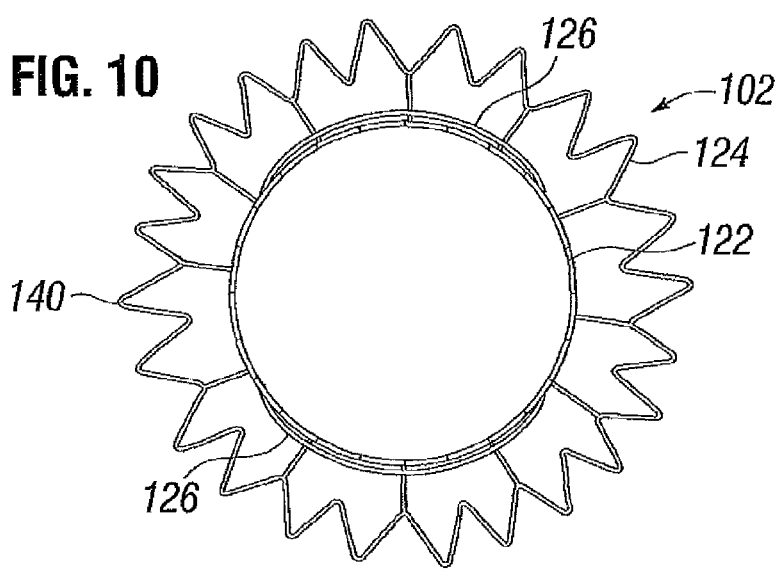

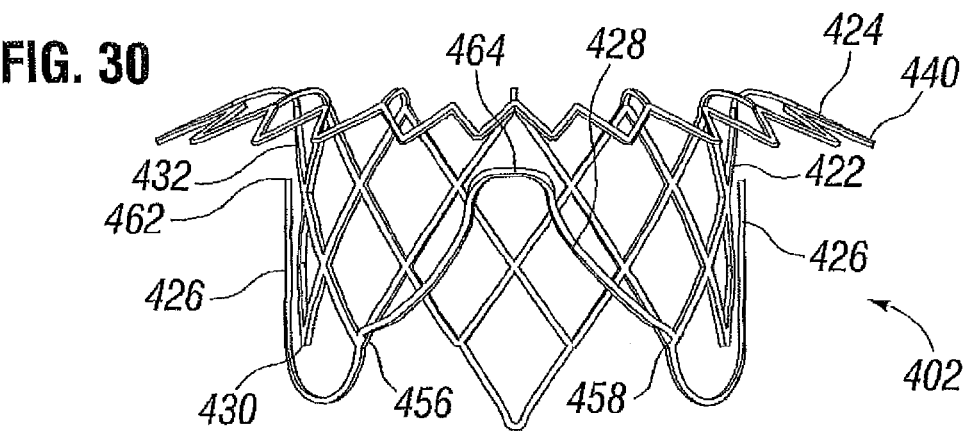
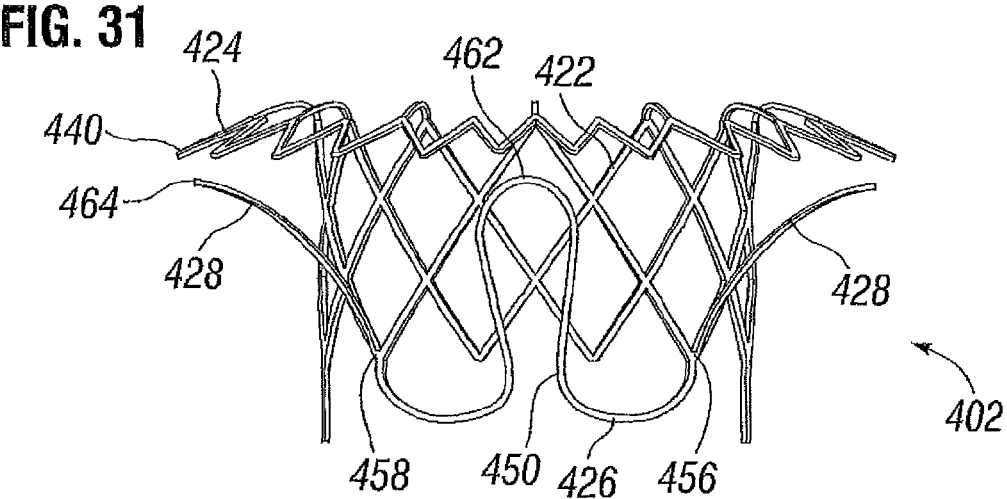
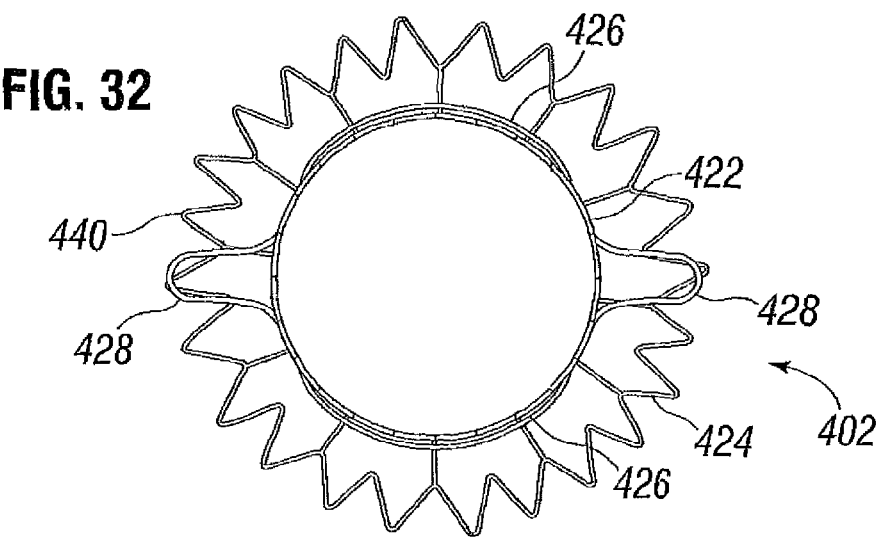

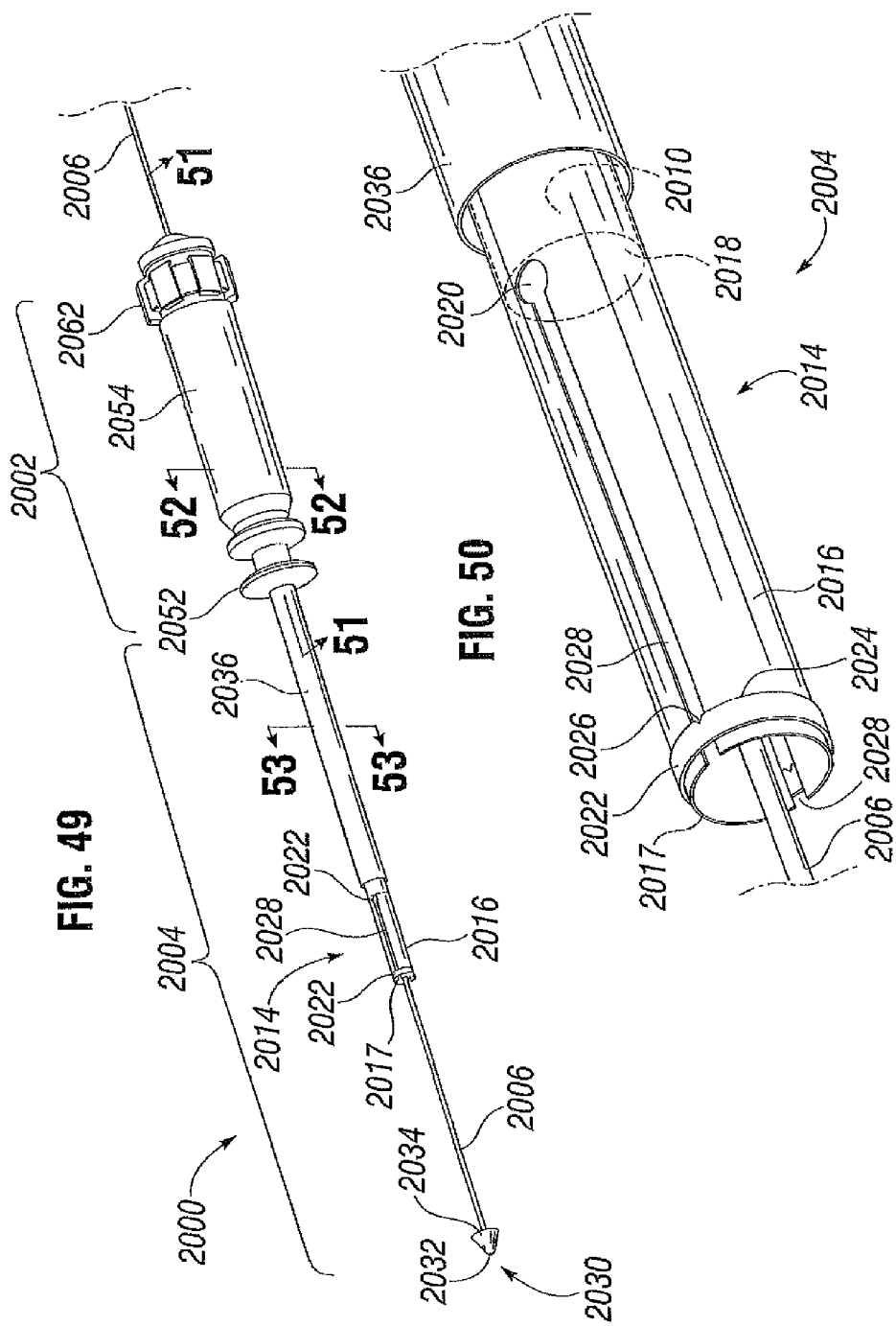

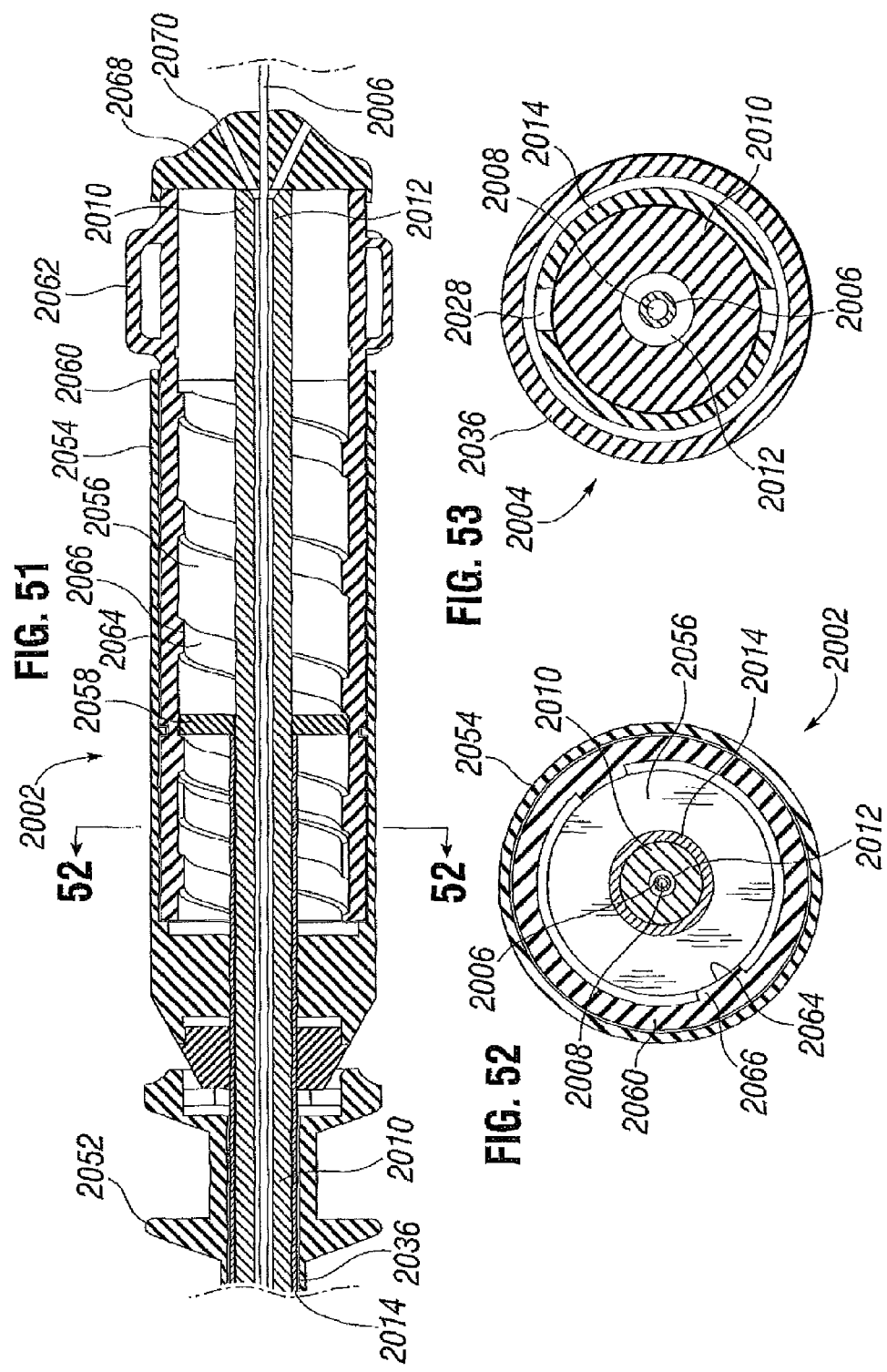

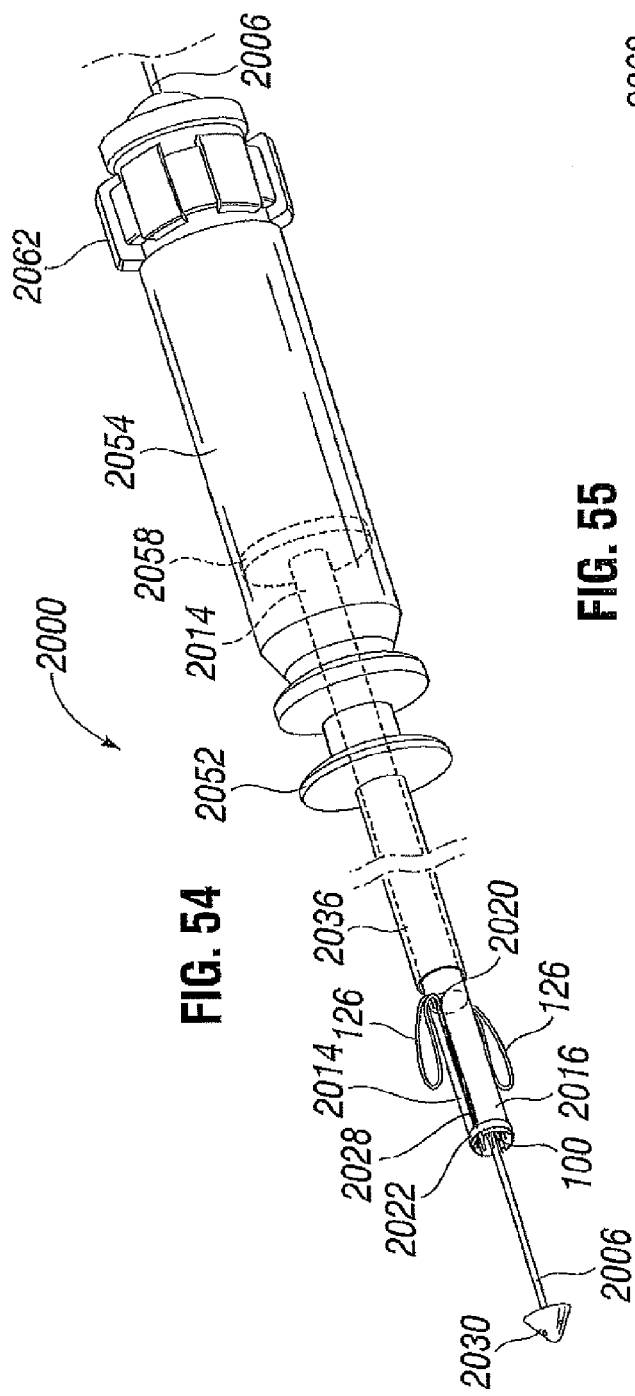
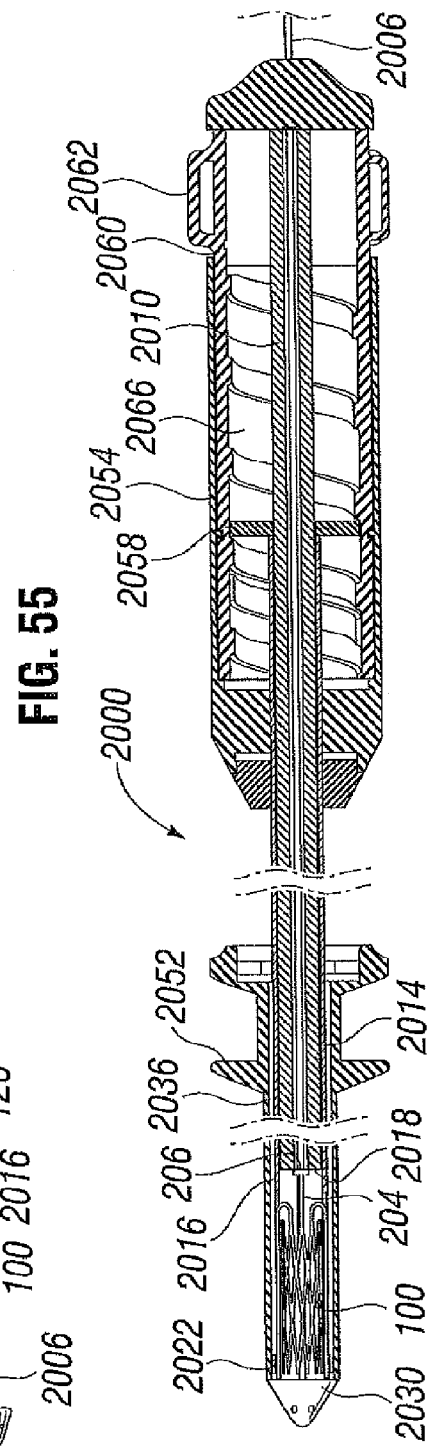

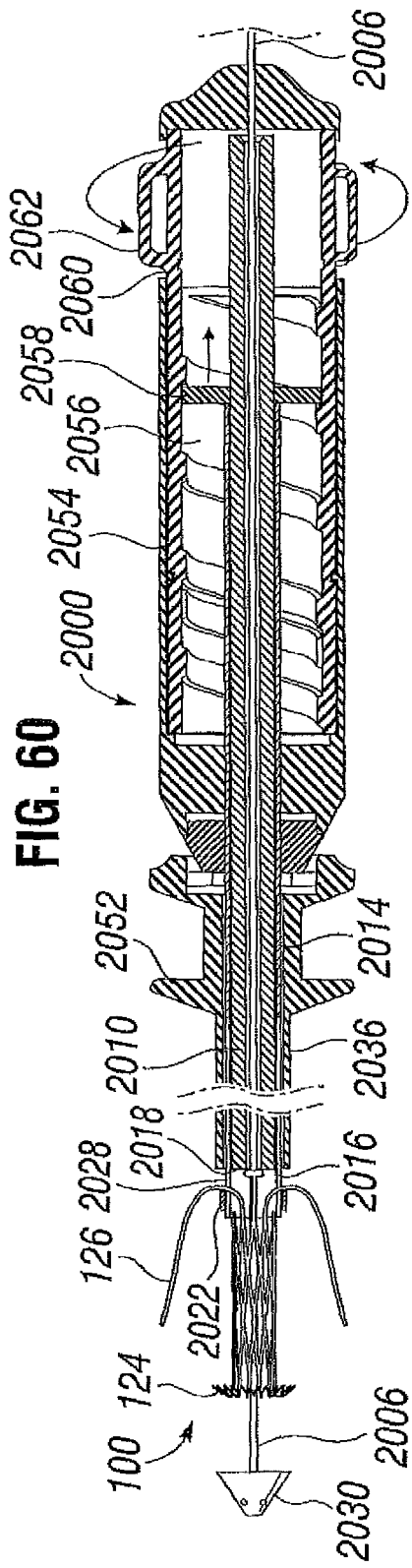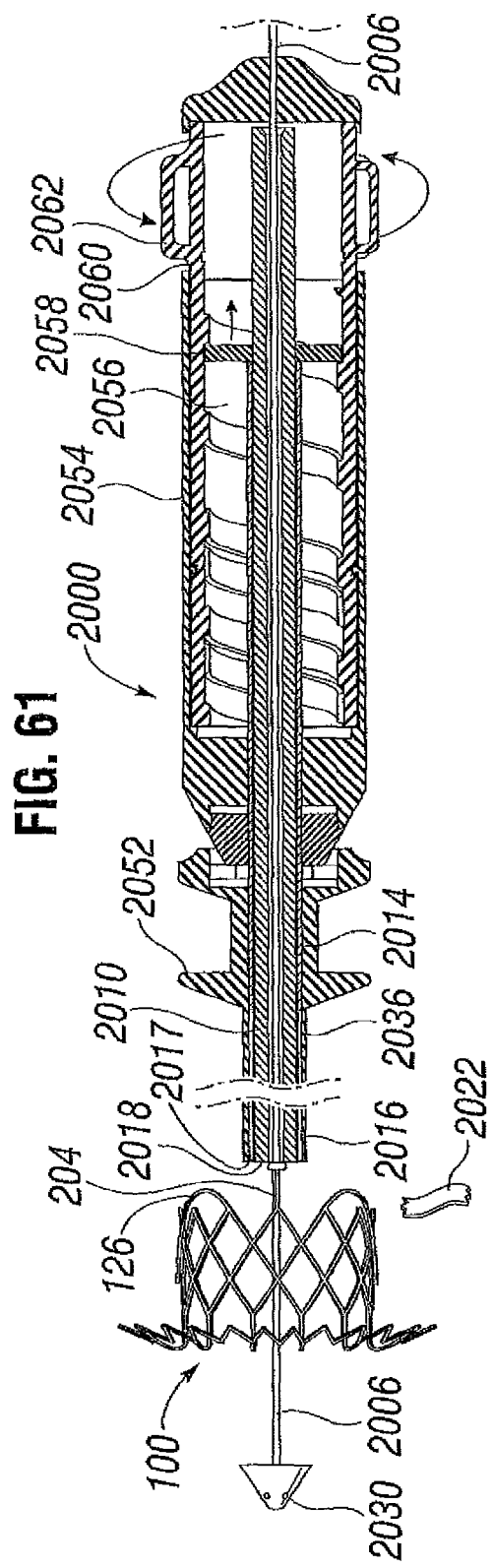

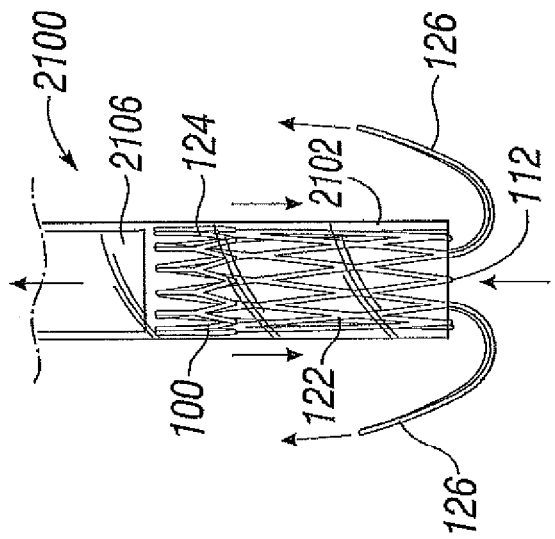
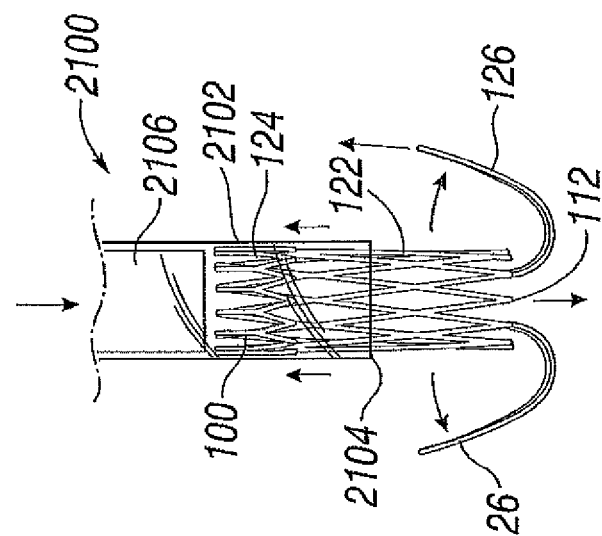
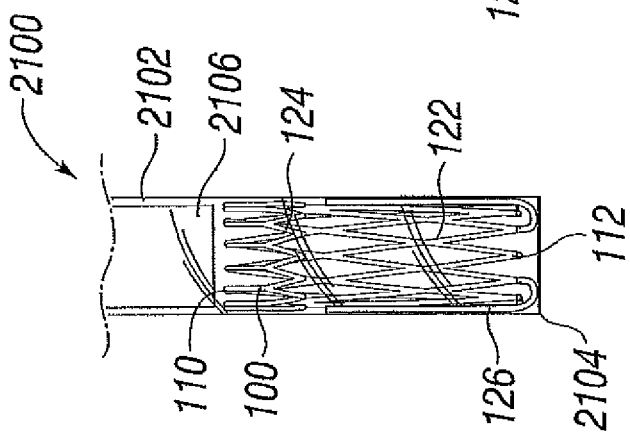

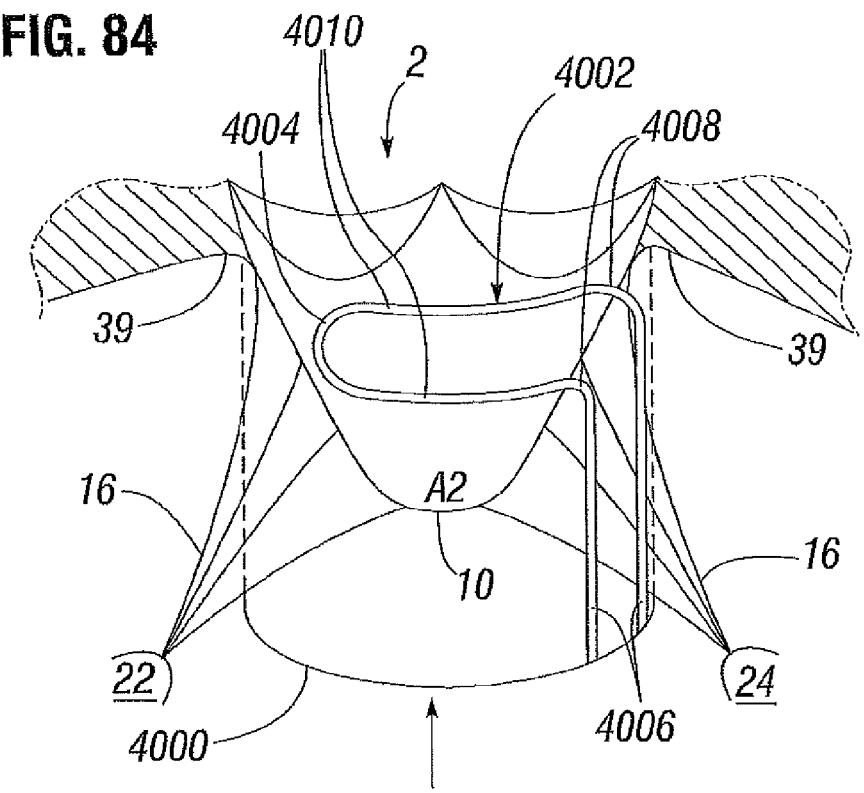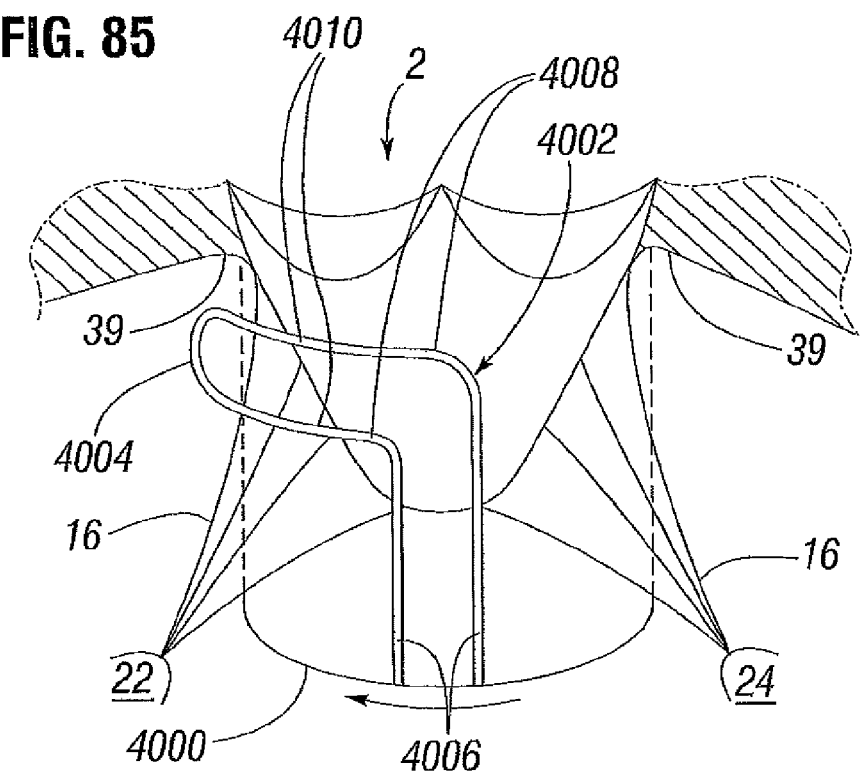

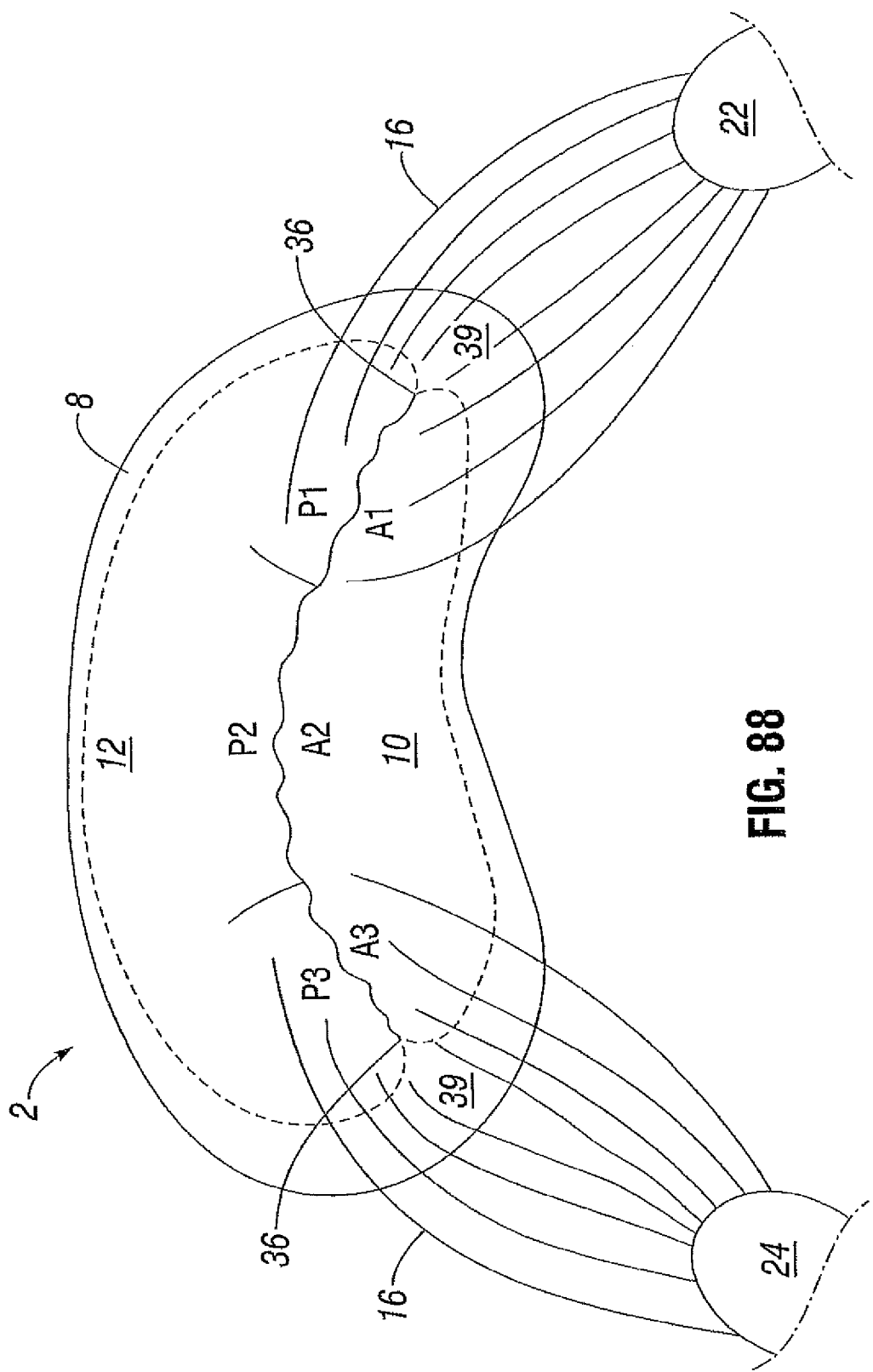

METHOD FOR IMPLANTING A PROSTHETIC MITRAL VALVE

CROSS REFERENCE TO RELATED APPLICATIONS

The present application is a continuation of U.S. patent application Ser. No. 13/597,122, filed Aug. 28, 2012, which is a continuation of U.S. patent application Ser. No. 12/959,292, filed Dec. 2, 2010, which issued as U.S. Pat. No. 8,449,599, which claims the benefit of U.S. Provisional Application Nos. 61/266,774, filed Dec. 4, 2009, and 61/287,099, filed Dec. 16, 2009, all of which are incorporated herein by reference.

FIELD

This disclosure pertains generally to prosthetic devices for repairing and/or replacing native heart valves, and in particular to prosthetic valves for replacing defective mitral valves, as well as methods and devices for delivering and implanting the same within a human heart.

BACKGROUND

Prosthetic valves have been used for many years to treat cardiac valvular disorders. The native heart valves (i.e., the aortic, pulmonary, tricuspid and mitral valves) serve critical functions in assuring the forward flow of an adequate supply of blood through the cardiovascular system. These heart valves can be rendered less effective by congenital malformations, inflammatory processes, infectious conditions or disease. Such damage to the valves can result in serious cardiovascular compromise or death. For many years the definitive treatment for such disorders was the surgical repair or replacement of the valve during open heart surgery. However, such surgeries are highly invasive and are prone to many complications. Therefore, elderly and frail patients with defective heart valves often go untreated. More recently a transvascular technique has been developed for introducing and implanting a prosthetic heart valve using a flexible catheter in a manner that is much less invasive than open heart surgery.

In this technique, a prosthetic valve is mounted in a crimped state on the end portion of a flexible catheter and advanced through a blood vessel of the patient until the valve reaches the implantation site. The valve at the catheter tip is then expanded to its functional size at the site of the defective native valve such as by inflating a balloon on which the valve is mounted.

Another known technique for implanting a prosthetic aortic valve is a transapical approach where a small incision is made in the chest wall of a patient and the catheter is advanced through the apex (i.e., bottom tip) of the heart. Transapical techniques are disclosed in U.S. Patent Application Publication No. 2007/0112422, which is hereby incorporated by reference. Like the transvascular approach, the transapical approach can include a balloon catheter having a steering mechanism for delivering a balloon-expandable prosthetic heart valve through an introducer to the aortic annulus. The balloon catheter can include a deflecting segment just proximal to the distal balloon to facilitate positioning of the prosthetic heart valve in the proper orientation within the aortic annulus.

The above techniques and others have provided numerous options for high operative risk patients with aortic valve disease to avoid the consequences of open heart surgery and cardiopulmonary bypass. While devices and procedures for the aortic valve are well-developed, such catheter-based procedures are not necessarily applicable to the mitral valve due to the distinct differences between the aortic and mitral valve. The mitral valve has complex subvalvular apparatus, i.e., chordae tendinae, which are not present in the aortic valve.

Surgical mitral valve repair techniques (e.g., mitral annuloplasty) have increased in popularity due to their high success rates, and clinical improvements noted after repair. In addition to the existing mitral valve repair technologies, there are a number of new technologies aimed at making mitral valve repair a less invasive procedure. These technologies range from iterations of the Alfieri stitch procedure to coronary sinus-based modifications of mitral anatomy to subvalvular plications or ventricular remodeling devices, which would incidentally correct mitral regurgitation.

However, for mitral valve replacement, few less-invasive options are available. There are approximately 25,000 mitral valve replacements (MVR) each year in the United States. However, it is estimated that over 300,000 patients who meet guidelines for treatment are denied treatment based on their age and/or co-morbities. Thus, a need exists for minimally invasive techniques for replacing the mitral valve.

SUMMARY

Prosthetic mitral valves, components thereof, and methods and devices for implanting the same are described herein.

A prosthetic apparatus is described that is configured for implanting at the native mitral valve region of the heart and includes a main body that is radially compressible to a radially compressed state and self-expandable from the compressed state to a radially expanded state. The prosthetic apparatus also comprises at least one ventricular anchor coupled to the main body and disposed outside of the main body such that when the main body is compressed to the compressed state, a leaflet-receiving space between the ventricular anchor and an outer surface of the main body increases to receive a native valve leaflet therebetween. When the main body self-expands to the expanded state in the absence of any substantial external inward forces on the main body or the ventricular anchor, the space decreases to capture the leaflet between the main body and the ventricular anchor.

In some embodiments, a prosthetic apparatus, for implanting at the native mitral valve region of the heart, includes a frame having a main body and at least one ventricular anchor coupled to and disposed outside of the main body. The prosthetic apparatus also includes a plurality of leaflets supported by the main body that form a one-way valve for the flow of blood through the main body. The main body is radially compressible to a radially compressed state for delivery into the body and self-expandable from the compressed state to a radially expanded state. The ventricular anchor comprises a base that is fixedly secured to the main body, a free end portion opposite the base, and an intermediate portion defining a leaflet-receiving space between the ventricular anchor and the main body for receiving a leaflet of the native valve. Expansion of the main body from its compressed state to its radially expanded state in the absence of any radial inward forces on the ventricular anchor causes the leaflet-receiving space to decrease.

In other embodiments, a prosthetic apparatus for implanting at the native mitral valve region includes a main body, at least one ventricular anchor and at least one atrial anchor. The main body is configured for placement within the native mitral valve and is compressible to a compressed state for delivery into the heart and self-expandable from the compressed state to an expanded state. At least one ventricular anchor is coupled to and disposed outside of the main body such that, in the expanded state, a leaflet-receiving space exists between the ventricular anchor and an outer surface of the main body to receive a free edge portion of a native valve leaflet. The ventricular anchor comprises an engagement portion configured to extend behind the received native leaflet and contact a ventricular surface of the native mitral annulus, the annulus connection portion of the received native leaflet, or both the ventricular surface of the native annulus and the annulus connection portion of the received native leaflet. At least one atrial sealing member is coupled to and disposed outside of the main body and is configured to contact an atrial portion of the native mitral annulus, the annulus connection portion of the received native leaflet, or both the atrial surface of the native annulus and the annulus connection portion of the received native leaflet at a location opposite from the engagement portion of the ventricular anchor for retention of the prosthetic apparatus and/or prevention of paravalvular leakage.

Exemplary delivery systems are also described for delivering a prosthetic apparatus into the heart. Some embodiments include an inner sheath having a distal end portion having at least one longitudinal slot extending proximally from a distal end of the inner sheath. The distal end portion of the inner sheath is configured to contain the prosthetic apparatus in a radially compressed state. An outer sheath is positioned concentrically around the inner sheath and at least one of the inner sheath and outer sheath is movable axially relative to the other between a first position in which the outer sheath extends over at least a portion of the longitudinal slot and a second position in which the at least a portion of the longitudinal slot is uncovered by the outer sheath so to allow a portion of the prosthetic apparatus contained within the inner sheath to expand radially outward through the slot.

Exemplary methods are also described for implanting a prosthetic apparatus at the native mitral valve region of the heart. One such method includes delivering the prosthetic apparatus into the heart in a radially compressed state; allowing a ventricular anchor to self-expand away from a main body of the frame while the main body is held in the compressed state, thereby increasing a gap between the ventricular anchor and an outer surface of the main body; positioning the main body in the annulus of the native mitral valve and the ventricular anchor adjacent the ventricular side of a native mitral valve leaflet such that the leaflet is disposed in the gap between the ventricular anchor and the outer surface of the main body; and allowing the main body to self-expand to an expanded state such that the gap decreases to capture the leaflet between the outer surface of the main body and the ventricular anchor.

BRIEF DESCRIPTION OF THE DRAWINGS

FIG. 2 is another cross sectional view of the human heart showing the mitral valve region.

FIG. 3 is a schematic view of the native mitral valve anatomy showing the mitral leaflets attached to the papillary muscles via chordae tendineae.

FIG. 4A is a diagram of native mitral valve showing Carpentier nomenclature.

FIG. 4B shows a native mitral valve with a gap between the leaflets.

FIGS. 4C and 4D show an exemplary prosthetic valve positioned within a native mitral valve.

FIG. 5 is a side view of an exemplary embodiment of a prosthetic valve.

FIG. 6 shows the prosthetic valve of FIG. 5 rotated 90 degrees with respect to a longitudinal axis of the value.

FIG. 7 is a ventricular (outflow) view of the prosthetic valve shown of FIG. 5.

FIGS. 8-10 are views corresponding to FIGS. 5-7, showing an exemplary embodiment of a frame of the prosthetic valve of FIGS. 5-7.

FIGS. 30-32 show the frame of the prosthetic valve shown in FIGS. 27-29.

FIG. 49 shows an exemplary embodiment of a delivery system for delivering and implanting a prosthetic valve at a native mitral valve region of the heart.

FIG. 50 is a detailed view of the distal portion of the delivery system of FIG. 49.

FIG. 51 is a cross-sectional view of a handle portion of the delivery system of FIG. 49, taken along section line 51-51.

FIG. 52 is a cross sectional view of the handle portion of the delivery system of FIG. 49, taken along section line 52-52.

FIG. 53 is a cross sectional view of an insertable portion of the delivery system of FIG. 49, taken along section line 53-53.

FIG. 54 shows the delivery system of FIG. 49 with a prosthetic valve loaded within a slotted inner sheath with the ventricular anchors extending outward through slots of the inner sheath.

FIG. 55 is a cross-sectional view of the delivery system of FIG. 49 in a delivery position containing the prosthetic valve within inner and outer sheaths and between a nose cone and a tip of a pusher shaft.

FIG. 60 is a cross-sectional view of the delivery system of FIG. 49 showing the slotted inner sheath retracted to a point where the ventricular anchors of the prosthetic valve contact a notched retaining band around the slotted inner sheath.

FIG. 61 is a cross-sectional view of the delivery system of FIG. 49 showing the slotted inner sheath fully retracted after the band has been broken, and the prosthetic valve in an expanded state after being fully deployed from the sheath.

FIG. 63 shows an exemplary embodiment of a prosthetic valve within a catheter sheath for delivering to a native valve region of the heart, according to another embodiment.

FIG. 64 shows the prosthetic valve of FIG. 63 with the catheter sheath pulled back such that the ventricular anchors are free to expand but the main body remains compressed.

FIG. 65 shows the prosthetic valve of FIG. 63 with the outer sheath recapturing the main body such that only the ventricular anchors are exposed.

FIGS. 84 and 85 show an exemplary method for implanting an exemplary prosthetic apparatus having "L" shaped ventricular anchors.

FIG. 88 is ventricular view of the native mitral valve region.

DETAILED DESCRIPTION

Described herein are embodiments of prosthetic valves and components thereof that are primarily intended to be implanted at the mitral valve region of a human heart, as well as apparatus and methods for implanting the same. The prosthetic valves can be used to help restore and/or replace the functionality of a defective native valve.

The Human Heart

Figure 1:
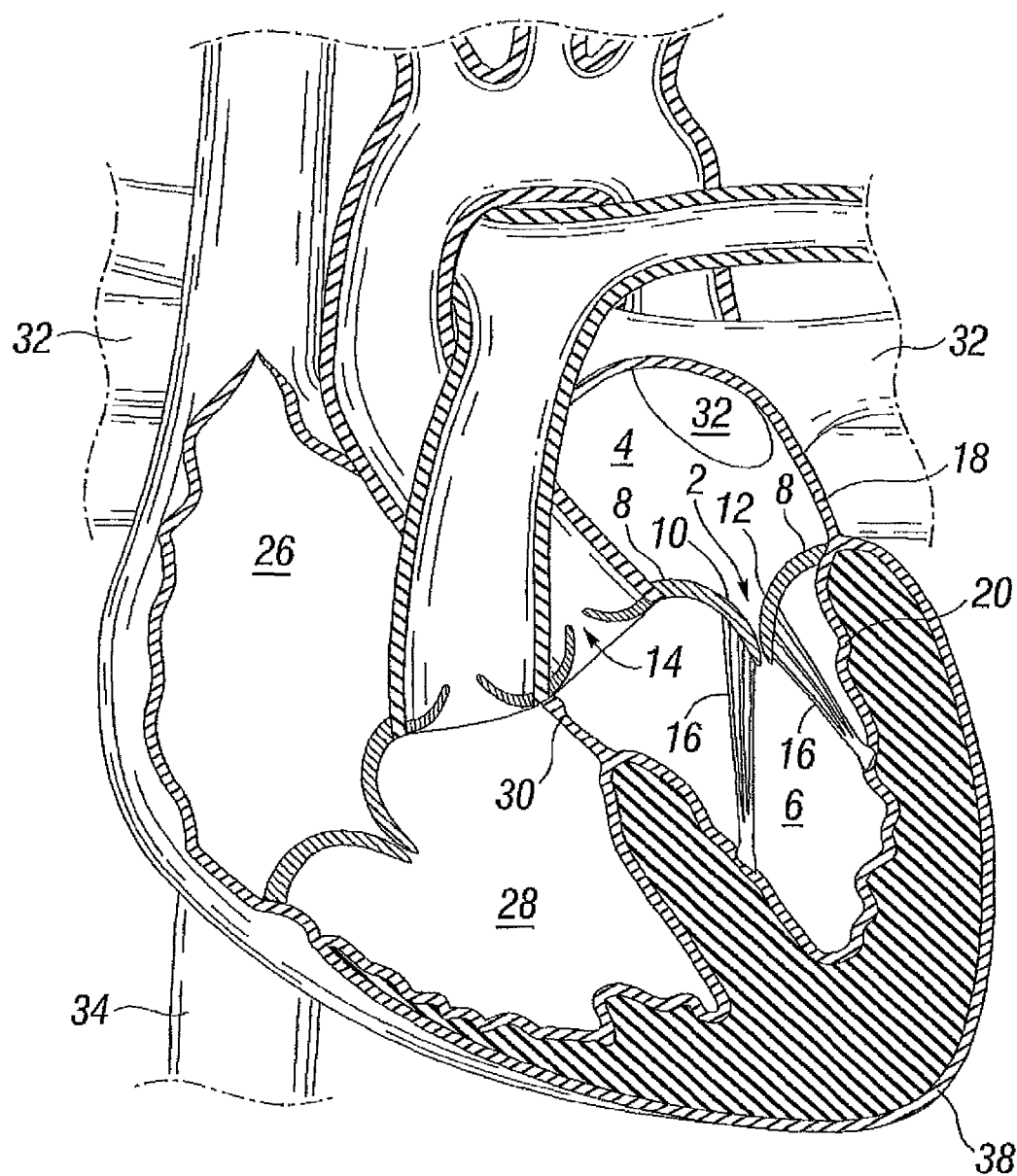
FIG. 1 is a cross sectional view of the human heart.
Figure 11:
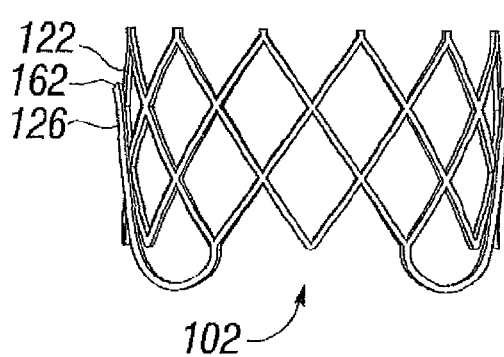
FIGS. 11-16 are a series of side views of the frame of FIG. 9, without the atrial sealing member, showing the leaflet-receiving spaces between the ventricular anchors and the main body increasing as the main body is radially compressed.
Figure 14:
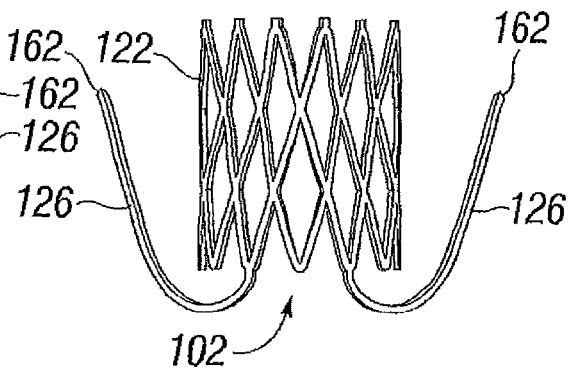
Figure 12:
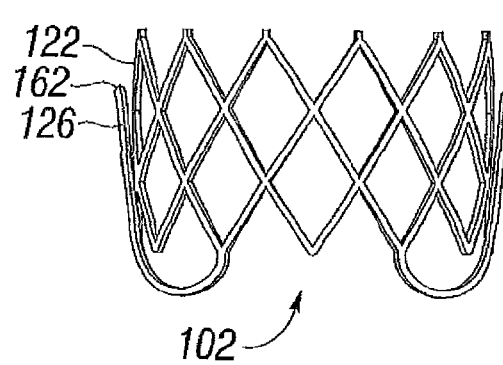
Figure 15:
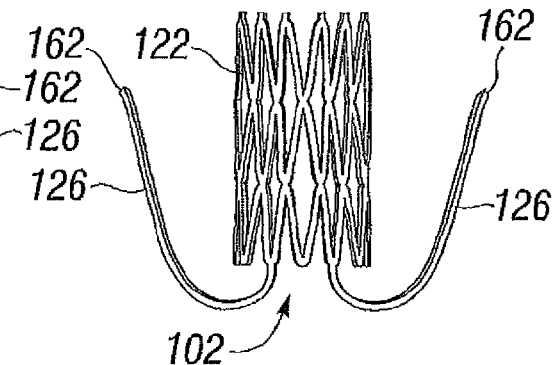
Figure 13:
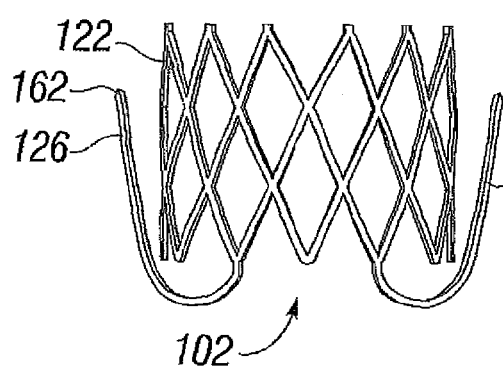
Figure 16:
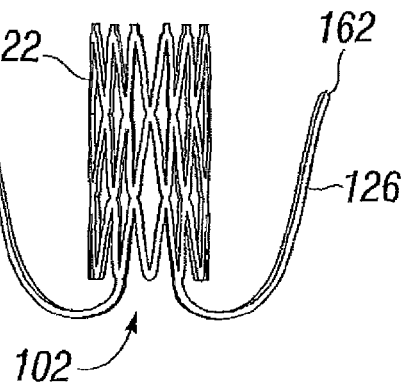
Figure 17:
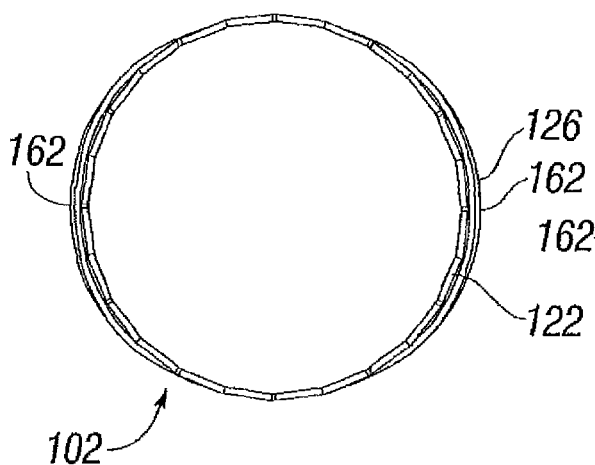
FIGS. 17-22 are a series of end views corresponding to FIGS. 11-16, respectively.
Figure 20:
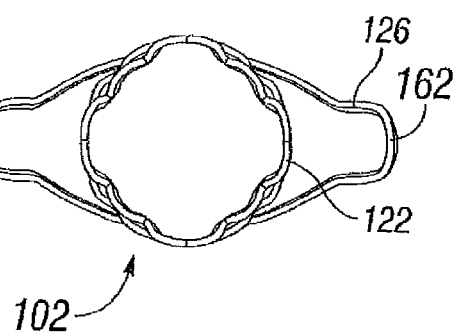
Figure 18:
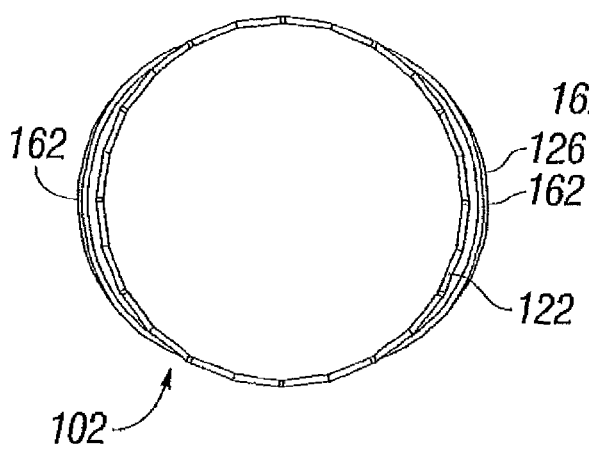
Figure 21:
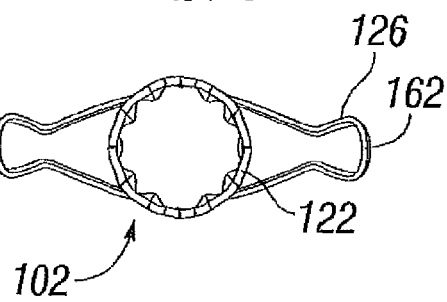
Figure 19:
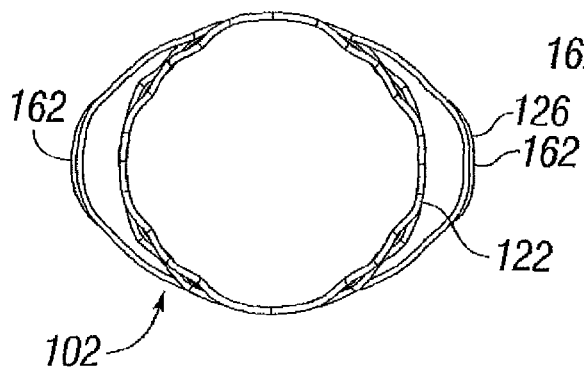
Figure 22:
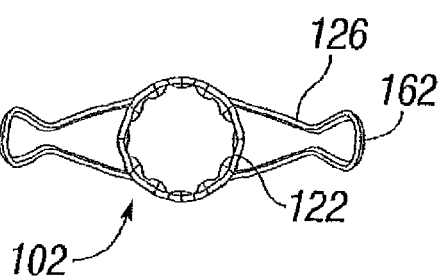

Relevant portions of the human heart are shown in FIGS. 1 and 2. A healthy heart has a generally conical shape that tapers to a lower apex 38. The heart is four-chambered and comprises the left atrium 4, right atrium 26, left ventricle 6, and right ventricle 28. The left and right sides of the heart are separated by a wall generally referred to as the septum 30. The native mitral valve 2 of the human heart connects the left atrium 4 to the left ventricle 6. The initial valve 2 has a very different anatomy than other native heart valves, such as the aortic valve 14.

The mitral valve 2 includes an annulus portion 8, which is an annular portion of the native valve tissue surrounding the mitral valve orifice, and a pair of cusps, or leaflets, 10, 12 extending downward from the annulus 8 into the left ventricle 6. The mitral valve annulus 8 can form a "D" shaped, oval, or otherwise out-of-round cross-sectional shape having major and minor axes. The anterior leaflet 10 can be larger than the posterior leaflet 12, as shown schematically in FIG. 4A, forming a generally "C" shaped boundary between the abutting free edges of the leaflets when they are closed together. FIG. 4B shows the native mitral valve 2 with a slight gap 3 between the leaflets 10, 12, such as with a defective native mitral valve that fails to completely close, which can lead to mitral regurgitation and/or other undesirable conditions.

When operating properly, the anterior leaflet 10 and the posterior leaflet 12 function together as a one-way valve to allow blood to flow only from the left atrium 4 to the left ventricle 6. The left atrium 4 receives oxygenated blood from the pulmonary veins 32. When the muscles of the left atrium 4 contract and the left ventricle dilates, the oxygenated blood that is collected in the left atrium 4 flows into the left ventricle 6. When the muscles of the left atrium 4 relax and the muscles of the left ventricle 6 contract, the increased blood pressure in the left ventricle urges the two leaflets together, thereby closing the one-way mitral valve so that blood cannot flow back to the left atrium and is instead expelled out of the left ventricle through the aortic valve 14.

To prevent the two leaflets 10, 12 from prolapsing under pressure and folding back through the mitral annulus 8 toward the left atrium 4, a plurality of fibrous cords called chordae tendineae 16 tether the leaflets 10, 12 to papillary muscles in the left ventricle 6. Referring to FIGS. 3 and 4, chordae 16 are attached to and extend between the postero-medial papillary muscle 22 and the postero-medial margins of both the anterior leaflet 10 and the posterior leaflet 12 (A1 and P1 areas, respectively, as identified by Carpentier nomenclature). Similarly, chordae 16 are attached to and extend between the antero-lateral papillary muscle 24 and the antero-lateral margins of both the anterior leaflet 10 and the posterior leaflet 12 (A3 and P3 areas, respectively, as identified by Carpentier nomenclature). The A2 and P2 areas are relatively free of chordae attachment points and provide a region where a prosthetic mitral valve can be anchored (see FIG. 3). In addition, the organization of the chordae provides an approach path to deliver a prosthetic mitral valve with minimal risk of chordae entanglement.

Prosthetic Valve

When the native mitral valve fails to function properly, a prosthetic valve replacement can help restore the proper functionality. Compared to the aortic valve 14, however, which has a relatively round and firm annulus (especially in the case of aortic stenosis), the mitral valve annulus 8 can be relatively less firm and more unstable. Consequently, it may not be possible to secure a prosthetic valve that is designed primarily for the aortic valve within the native mitral valve annulus 8 by relying solely on friction from the radial force of an outer surface of a prosthetic valve pressed against the native mitral annulus 8. Accordingly, the prosthetic valves described herein can rely on ventricular anchors instead of, or in addition to, radial friction forces, to secure the prosthetic valve within the native mitral valve annulus 8 (see FIG. 23, for example).

In addition to providing an anchoring means for the prosthetic valve, the ventricular anchors can also remodel the left ventricle 6 to help treat an underlying cause of mitral regurgitation—left ventricle enlargement/dilation. The ventricular anchors can pull the native mitral valve leaflets 10, 12 closer together and toward the left atrium and, via the chordae 16, thereby pull the papillary muscles 22, 24 closer together, which can positively remodel the ventricle acutely and prevent the left ventricle from further enlarging. Thus, the ventricular anchors can also be referred to as tensioning members or reshaping members.

FIGS. 5-7 illustrate an exemplary prosthetic valve 100, according to one embodiment, that can be implanted in the native mitral valve region of the heart to replace the functionality of the native mitral valve 2. The prosthetic valve 100 comprises a frame 102 and a valve structure 104 supported by and/or within the frame. The valve structure 104 can include a plurality of prosthetic leaflets 106 (three in the illustrated embodiment) and/or other components for regulating the flow of blood in one direction through the prosthetic valve 100. In FIGS. 5 and 6, for example, valve structure 104 is oriented within the frame 102 such that an upper end 110 of the valve structure is the inflow end and a lower end 112 of the valve structure is the outflow end. The valve structure 104 can comprise any of various suitable materials, such as natural tissue (e.g., bovine pericardial tissue) or synthetic materials. The valve structure 104 can be mounted to the frame 102 using suitable techniques and mechanisms. In the illustrated embodiment, for example, the leaflets 106 are sutured to the frame 102 in a tricuspid arrangement, as shown in FIG. 7.

Additional details regarding components and assembly of prosthetic valves (including techniques for mounting leaflets to the frame) are described, for example, in U.S. Patent Application Publication No. 2009/0276040 A1 and U.S. patent application Ser. No. 12/393,010, which are incorporated by reference herein.

Figure 23:
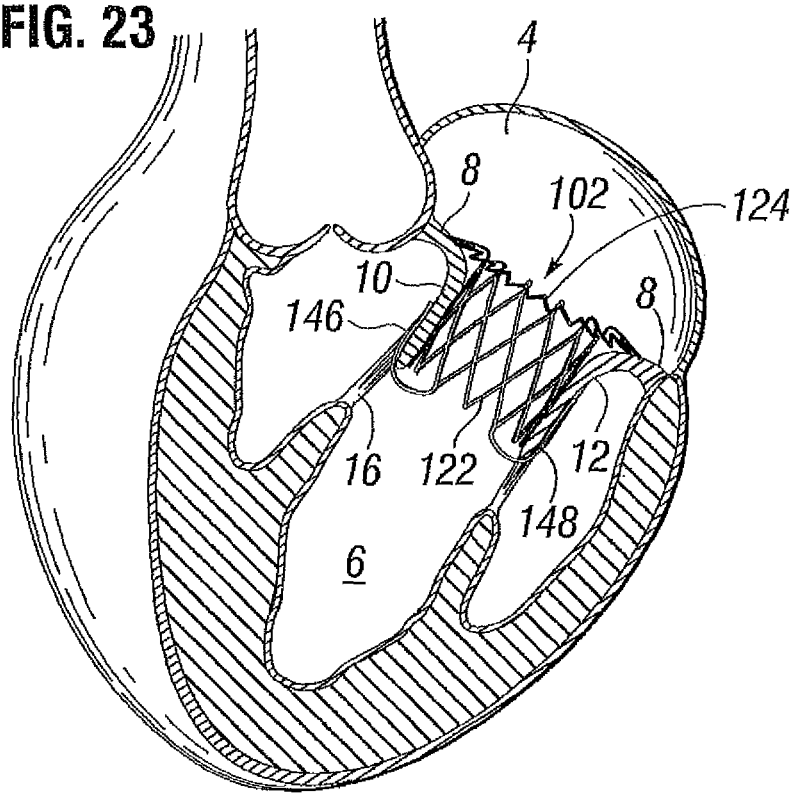
FIG. 23 is a cross-sectional view of the heart showing the frame of FIG. 9 implanted in the mitral valve region, wherein the native mitral valve leaflets are captured between the main body and the ventricular anchors.

As shown in FIGS. 8-10, the frame 102 can comprise a tubular main body 122, one or more ventricular anchors 126 extending from a ventricular end 130 of the main body and optionally an atrial sealing member 124 extending radially outward from an atrial end 132 of the main body. When the frame 102 is implanted in the native mitral valve region of the heart, as shown in FIG. 23, the main body 122 is positioned within the native mitral valve annulus 8 with the ventricular end 130 of the main body 122 being a lower outlet end, the atrial end 132 of the main body 132 being an upper inlet end, the ventricular anchors 126 being located in the left ventricle 6, and the atrial sealing member 124 being located in the left atrium 4.

The frame 102 can be made of a wire mesh and can be radially collapsible and expandable between a radially expanded state and a radially compressed state (as shown schematically in a series of successive stages in FIGS. 11-16 and 17-22) to enable delivery and implantation at the mitral valve region of the heart (or within another native heart valve). The embodiments of the frame 102 shown in FIGS. 11-22 do not include an atrial sealing member 124, though other embodiments of the frame 102 do include an atrial sealing member 124. The wire mesh can include metal wires or struts arranged in a lattice pattern, such as the sawtooth or zig-zag pattern shown in FIGS. 8-10 for example, but other patterns may also be used. The frame 102 can comprise a shape-memory material, such as Nitinol for example, to enable self-expansion from the radially compressed state to the expanded state. In alternative embodiments, the frame 102 can be plastically expandable from a radially compressed state to an expanded state by an expansion device, such as an inflatable balloon (not shown) for example. Such plastically expanding frames can comprise stainless steel, chromium alloys, and/or other suitable materials.

In an expanded state, as shown in FIGS. 8-10, the main body 122 of the frame 102 can form an open-ended tube. The valve structure 104 can be coupled to an inner surface of the frame 102, such as via a material layer 142 on the inner surface of the frame, as discussed below, and can be retained within the lumen formed by the main body 122, as shown in FIG. 7. An outer surface of the main body 122 can have dimensions similar to that of the mitral orifice, i.e., the inner surface of the mitral annulus 8, but not necessarily. In some embodiments, for example, the outer surface of the main body 122 can have diametrical dimensions that are smaller than the diametrical dimensions of the native mitral orifice, such that the main body 122 can fit within the mitral orifice in the expanded state without substantially stretching the native mitral annulus 8, such as in FIG. 23. In such embodiments, the frame 102 need not rely on a pressure fit, or friction fit, between the outer surface of the main body 122 and the inner surface of the mitral annulus 8 for prosthetic valve retention. Instead, the frame 102 can rely on the ventricular anchors 126 and/or the atrial sealing member 124 for retention, as further described below. In other embodiments, however, the main body 122 can be configured to expand to an equal or greater size than the native mitral orifice and thereby create a pressure fit when implanted.

In embodiments wherein the main body 122 comprises diametrical dimensions that are smaller than the diametrical dimensions of the native mitral orifice, the main body can sit loosely, or "float," between the native leaflets 10, 12. As shown in FIG. 4C, this loose fit can create gaps 37 between the leaflets 10, 12 and the main body 122 of the frame. To prevent blood flow between the outside of the prosthetic valve 100 and the native valve tissue, such as through the gaps 37, the annular atrial sealing member 124 can create a fully annular contact area, or seal, with the native tissue on the atrial side of the mitral annulus 8. Accordingly, as shown in FIG. 4D, the atrial sealing member 124 can be sized to fully cover the gaps 37.

The ends of the frame 102 can have a sawtoothed or zig-zag pattern, as shown in FIGS. 8-10, comprising a series of side-by-side "V" shaped portions connected together at their upper ends, for example. This pattern can facilitate compression and can help maximize a surface area with which the frame connects to the native tissue. Alternatively, the ends of the frame 102 can have a straight edge, or some other pattern.

Figure 25:
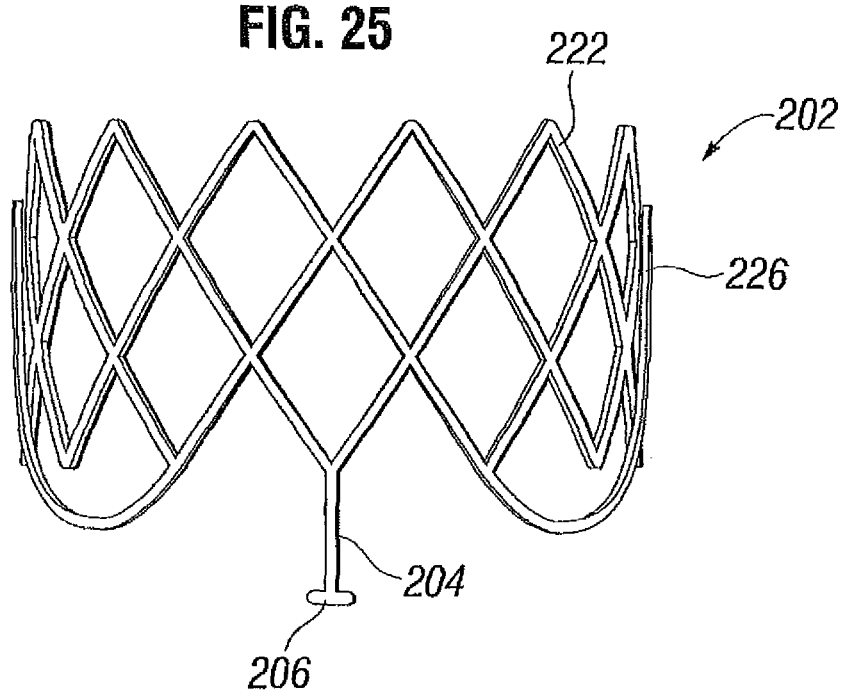
FIG. 25 shows an exemplary embodiment of a frame, with the atrial sealing member excluded, comprising a "T" shaped pushing member extending downward from a ventricular end of the main body.
Figure 26:
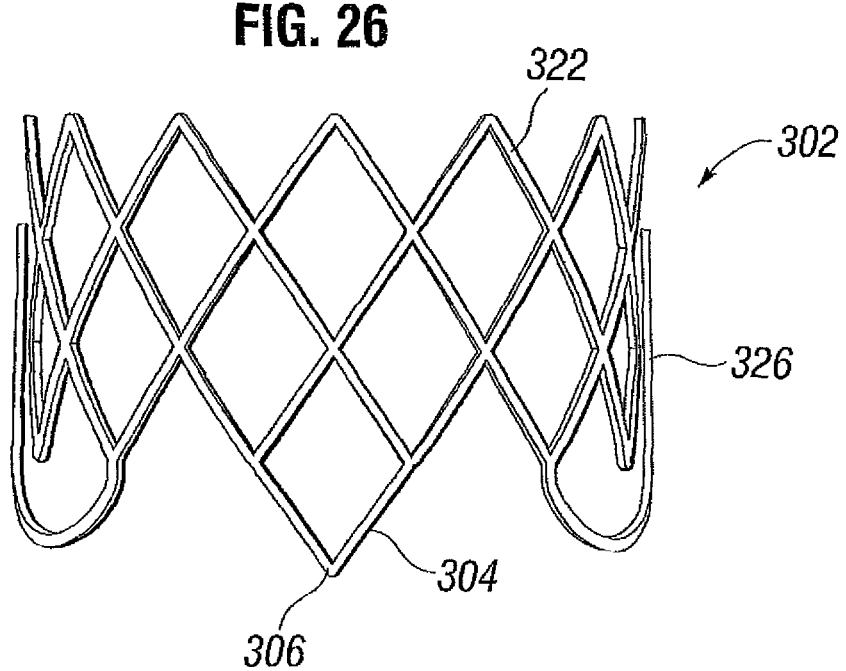
FIG. 26 shows an exemplary embodiment of a frame, with the atrial sealing member excluded, comprising a "V" shaped pushing member extending downward from the ventricular end of the main body.
Figure 27:
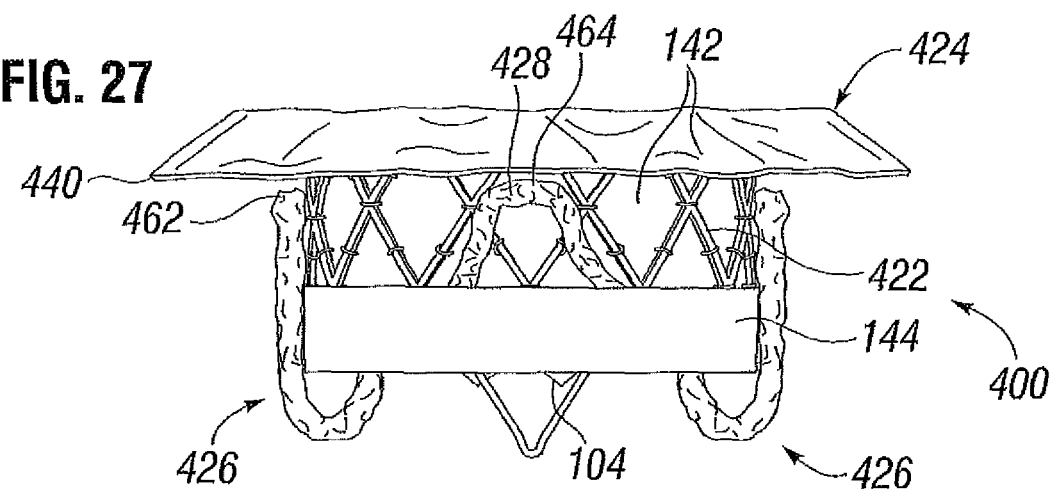
FIGS. 27-29 show an exemplary embodiment of a prosthetic valve having a frame with four ventricular anchors.
Figure 28:
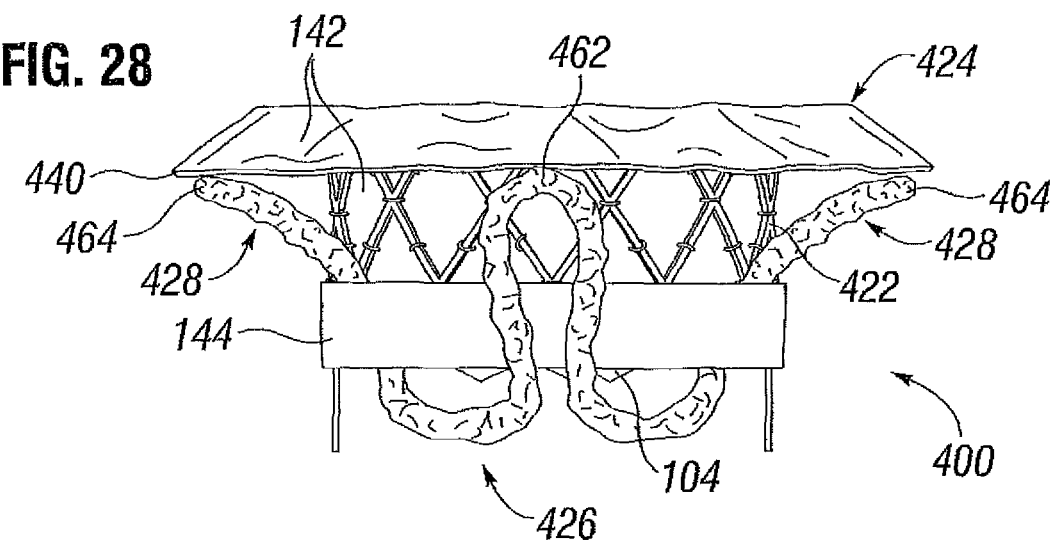
Figure 29:
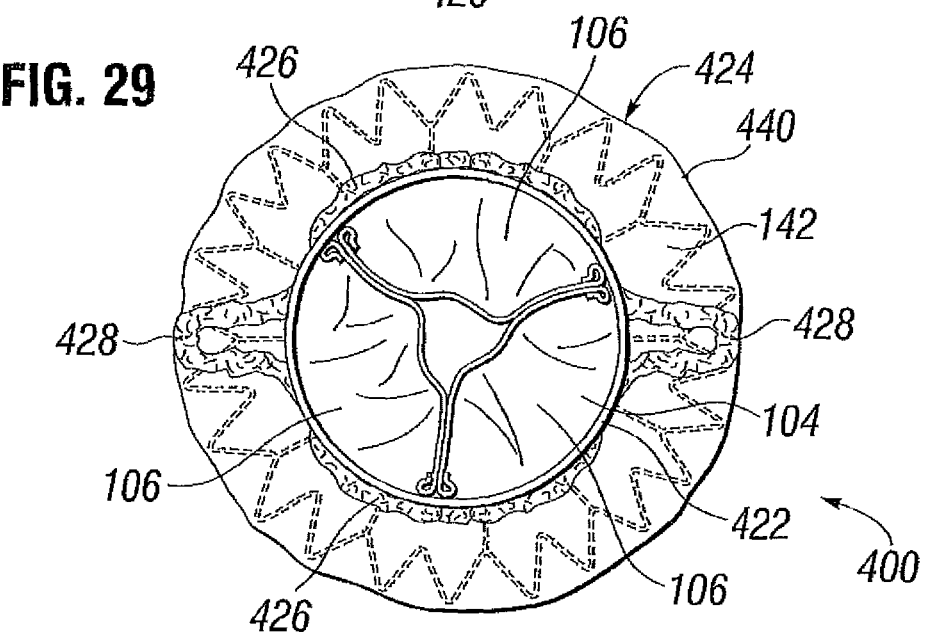

In some embodiments, the main body 122 can comprise at least one extension member, or pushing member, that extends downward from the ventricular end 130 of the main body 122. The frame 202 shown in FIG. 25, for example, comprises an extension member in the form of a prong 204 that extends from the lower vertex of one of the "V" shaped portions of a main body 222. The prong 204 can have an upside-down "T" shape comprising a lower pushing surface 206. In another embodiment, the frame 302 shown in FIG. 26 comprises a "V" shaped pushing member 304 that extends from two adjacent lower vertices of a main body 322 and comprises a pushing surface 306. The pushing surfaces 206 and 306 can comprise the lowermost points on the frames 202 and 302, respectively, and can provide a pushing surface for the frame to be expelled out of a delivery device without contacting the ventricular anchors 226, 326, as described in more detail below.

With reference again to the embodiment shown in FIGS. 8-10, the atrial sealing member 124 of the frame 102 can be integral with the main body 122 and can be comprised of the same wire mesh lattice as the main body 122 such that the atrial sealing member 124 can also be radially collapsible and expandable. In the expanded state, the atrial sealing member 124 can be generally frustoconical and extend from the atrial end 132 of main body 122 both radially outward and axially downward toward the ventricular end 130 of the main body 122. An outer rite 140 of the atrial sealing member 124 can be sized and shaped to contact the atrial side of the mitral annulus and tissue of the left atrium 8 when the frame 102 is implanted, as shown in FIG. 23. The end view profile of the outer rim 140, as shown in FIG. 10, can have a generally circular, oval, or other shape that generally corresponds to the native geometry of the atrial walls 18 and the mitral annulus 8. The contact between the atrial sealing member 124 and the tissue of the atrial walls 18 and/or the mitral annulus 8 can promote tissue ingrowth with the frame, which can improve retention and reduce paravalvular leakage.

The atrial sealing member 124 desirably is sized such that when the prosthetic valve 100 is implanted in the native mitral valve, as shown in FIG. 23, the outer rim 140 contacts the native annulus 8 around the entire native valve and therefore completely covers the opening between the native leaflets 10, 12. The atrial sealing member 124 desirably includes a sealing layer 142 that is impervious to the flow of blood. In this manner, the atrial sealing member 124 is able to block blood from flowing back into the left atrium between the outer surfaces of the prosthetic valve 100 and the native valve tissue. The atrial sealing member also ensures that all, or substantially all, of the blood passes through the one-way valve as it flows from the left atrium to the left ventricle.

As shown in FIGS. 5-7, at least one biocompatible sheet or layer 142 can be connected to the inner and/or outer surfaces of the main body 122 and the atrial sealing member 124 to form at least one layer or envelope covering the openings in the wire mesh. The layer 142 can be connected to the frame 102 by sutures, for example. The layer 142 can form a fluid-occluding and/or sealing member that can at least partially block the flow of blood through the wire mesh to reduce paravalvular leakage and can promote tissue ingrowth with the frame 102. The layer 142 can provide a mounting surface, or scaffold, to which the portions of the valve structure 104, such as the leaflets 106, can be secured. For example, the dashed line 108 in FIGS. 5 and 6 represents where the inlet ends of the leaflets 106 can be sewn, sutured, or otherwise secured to the layer 142. This seam between the inlet ends of the leaflets 106 and the layer 142 can form a seal that is continuous around the inner perimeter of the layer 142 and can block blood flow between the inner surface of the layer 142 and the outer surface of the leaflets 106. This seal can allow the prosthetic valve 100 to direct blood to flow between the plurality of leaflets 106.

The same layer 142 and/or one or more separate cuffs 144 can also wrap around, or cover, the end edges of the frame 102, such as the ventricular end 130 of the main body 122 and/or the outer rim 140 of the atrial sealing member 124. Such a cuff 144 can cover and protect sharp edges at the ends of the frame 102. For example, in the embodiment shown in FIG. 5, the layer 142 extends from the outer rim 140 across the upper surface of the atrial sealing member 124 and downward along the inner surface of the main body 122 and comprises a cuff 144 that wraps around and covers a ventricular end portion of the main body 122. The layer 142 can be sutured to the outer rim 140 and to the inner surface of the main body 122.

The layer 142 can comprise a semi-porous fabric that blocks blood flow but can allow for tissue ingrowth. The layer 142 can comprise synthetic materials, such as polyester material or a biocompatible polymer. One example of a polyester material is polyethylene terephthalate (PET). Alternative materials can be used. For example, the layer can comprise biological matter, such as natural tissue, pericardial tissue (e.g., bovine, porcine, or equine pericardium) or other biological tissue.

With reference to FIGS. 8 and 9, one or more ventricular anchors 126 can extend from the main body 122 of the frame 102, such as from the ventricular end 130 of the main body. The ventricular anchors 126 can function to retain the frame 102, with or without the valve structure 104, within a native valve region of the heart. In the embodiment shown in FIGS. 8 and 9, the frame 102 comprises two diametrically opposed ventricular anchors 126 that can function to secure the frame 102 to the anterior and posterior mitral leaflets 10, 12, respectively, when the frame 102 is implanted in the mitral valve region, as shown in FIG. 23. In alternate embodiments, the frame 102 can have three or more ventricular anchors 126, which can be angularly spaced around the main body 122 of the frame.

When the frame 102 is in an expanded state, as in FIG. 9, the geometry of the frame can cause the ventricular anchors 126 to be urged against the outer surface of the main body 122. Alternatively, the ventricular anchors 126 can be configured to be spaced apart from the outer surface of the main body 122 when the frame 102 is in the expanded state (see FIG. 39, for example). In any case, when the frame 102 is radially compressed to the compressed state, the space or gap between the ventricular anchors 126 and the outer surface of the main body 122 can increase, as shown in FIGS. 11-16.

Figure 59:
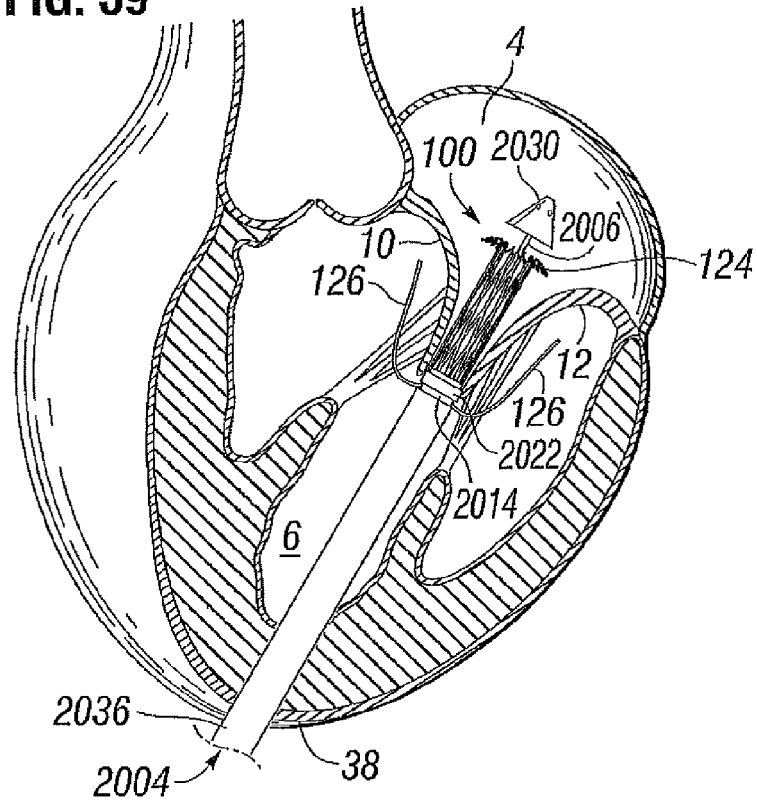
FIG. 59 is a cross-sectional view of the heart showing the prosthetic valve being implanted in the mitral valve region using the delivery system of FIG. 49 with the native leaflets positioned between the ventricular anchors and the inner sheath.

While the main body 122 and the atrial sealing member 124 are in the compressed state, the frame 102 can be inserted into the mitral valve orifice such that the spaced apart ventricular anchors 126 wrap around the leaflets 10, 12 and extend upward between the leaflets and the ventricular walls 20 (see FIG. 59, for example). With reference to FIG. 23, an anterior ventricular anchor 146 can be located behind the anterior leaflet 10 and a posterior ventricular anchor 148 can be located behind the posterior leaflet 12. With reference to FIGS. 3 and 4, the two ventricular anchors are desirably located behind the respective leaflets near the middle portions of the leaflets A2, P2 about midway between the commissures 36 where the two leaflets meet. These middle portions A2, P2 of the leaflets 10,12 are desirable ventricular anchor locations because the chordae tendineae 16 attachments to the leaflets are sparser in these locations compared to locations nearer to the commissures 36.

When the main body 122 is subsequently expanded or allowed to self-expand to the expanded state, as shown in FIGS. 11-16 in reverse order, the ventricular anchors are configured to pivot radially inward relative to the main body 122, without external compressive forces on the ventricular anchors. This causes the gaps between the ventricular anchors 126 and the outer surface of the main body 122 to decrease, thereby enabling the capture of the leaflets 10, 12 between the ventricular anchors and the main body. Conversely, compressing the main body 122 causes the ventricular anchors 126 to pivot away from the main body to increase the gaps between the outer surface of the main body and the ventricular anchors. In some embodiments, the free ends, or apexes, 162 of the ventricular anchors 126 can remain substantially the same distance apart from one another as the main body 122 is radially compressed or expanded free of external forces on the ventricular anchors. In some embodiments, such as the embodiment shown in FIG. 23, the frame is configured to compress the native mitral leaflets 10, 12 between the main body and the ventricular anchors when the frame expands to the expanded state. In other embodiments, such as the embodiment shown in FIG. 39, the ventricular anchors do not compress or clamp the native leaflets against the main body but still prevent the prosthetic valve from migrating toward the left atrium by the hooking of the ventricular anchors around the native leaflets 10, 12. In such embodiments, the prosthetic valve 100 can be retained in place against migration toward the left ventricle by the atrial sealing member 124 as further described below.

With reference to the embodiment shown in FIGS. 8-10, each ventricular anchor 126 can comprise a flexible, elongate member, or wire, 150 comprised of a shape memory material, such as, for example, Nitinol. In some embodiments, as shown in FIG. 8, each wire 150 can comprise a first end portion 152 coupled to a first attachment location 156 of the main body 122, and a second end portion 154 coupled to a second attachment location 158 of the main body. The first and second end portions 152, 154 form a base of the ventricular anchor. The first and second attachment locations 152, 154 of the main body can be at, or adjacent to, the ventricular end 130 of the main body 122. The two end portions 152, 154 of each wire 150 can be extensions of the wires or struts that make up the lattice mesh of the main body 122. Each wire 150 further comprises an intermediate portion 160 extending in a direction lengthwise of the main body between the end portions 152, 154. The intermediate portion 160 includes a bend 162 that forms the free end portion, or apex, of the ventricular anchor.

The wire 150 can have a circular or non-circular cross-sectional profile perpendicular to a length of the wire, such as a polygonal cross-sectional profile. With reference to FIG. 8A, the wire 150 can comprise a rectangular cross-sectional shape having a length "L" and a relatively narrower width "W" such that when the two end portions 152, 154 of the ventricular anchor 126 attached to the frame 102 are moved toward each other, such as when the frame is compressed, the wire 150 bends primarily in the width direction. This promotes bending of the ventricular anchor 126 in a direction radially outward away from the main body 122, widening the gap between the ventricular anchor 126 and the main body 122. This feature can help to capture a leaflet between the ventricular anchor 126 and the main body 122 during implantation.

Ventricular anchors can comprise various shapes or configurations. Some frame embodiments, such as the frame 102 shown in FIG. 8, comprise generally "U" or "V" shaped ventricular anchors 126 that connect to the main body 122 at two attachment locations 156, 158. The upper apex 162 of the ventricular anchors 126 can function like a wedge to facilitate moving the ventricular anchors behind respective leaflets while minimizing the risk of chordae entanglement. The end portions 152, 154 of each wire 150 can extend downward from attachment locations 156, 158, respectively, at the ventricular end 130 of the main body 122. The wire 150 can then curve back upward from each end portion 152, 154 toward the apex 162.

The wires 150 can be covered by biocompatible materials, such as in the embodiment shown in FIGS. 5-7. A first material 164 can be wrapped around, or coat, at least some portion of the wire 150. A second material 166 can span across two portions of the wire 150 to form a web, which can improve tissue ingrowth. The first and second materials 164, 166 can comprise the same material or different materials, such as a biocompatible semi-porous fabric, for example. The covering materials 164, 166 can increase tissue ingrowth with the ventricular anchor 126 to improve retention. Furthermore, the covering materials can decrease the frictional properties of the ventricular anchors 126 to facilitate implantation and/or increase the frictional properties of the ventricular anchors to improve retention.

Figure 24:
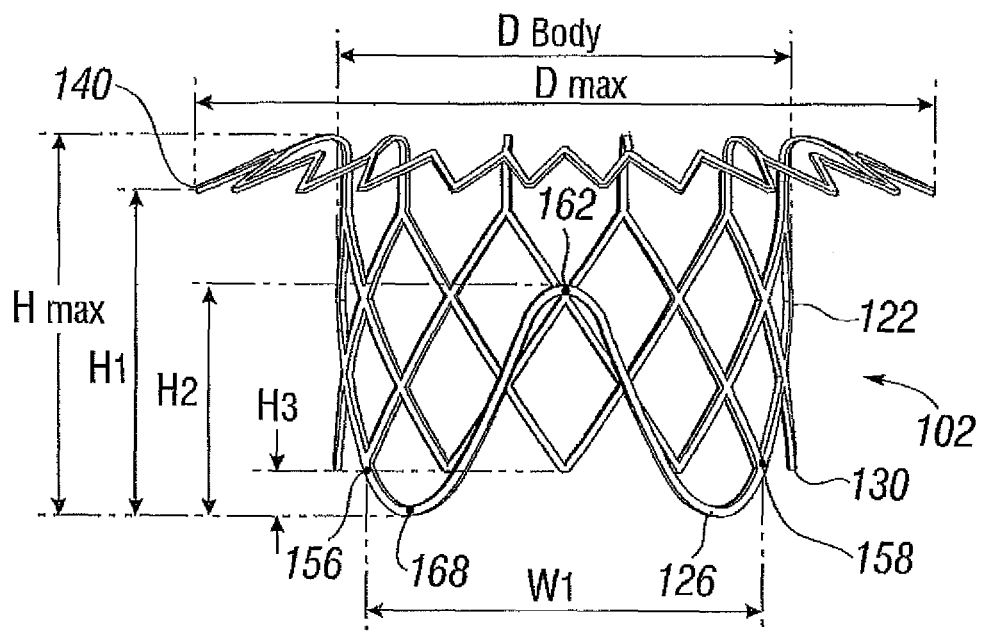
FIG. 24 shows exemplary dimensions of the atrial sealing member, main body and ventricular anchors of FIG. 9.

FIG. 24 shows exemplary dimensions of the embodiment of the frame 102 shown in FIG. 9. The diameter "Dmax" of the outer rim 140 of the atrial sealing member 124 can range from about 50 mm to about 70 mm, and is about 50 mm in one example. The diameter "Dbody" of the outer surface of the main body 122 can range from about 23 min to about 50 mm, and is about 29 mm in one example. The distance "W1" between the two attachment points 156, 158 for one ventricular anchor 126 can range from about 8 mm to about 50 mm, and is about 25 mm in one example. The overall axial height "Hmax" of the frame 102 can range from about 20 mm to about 40 mm, and is about 30 mm in one example. The axial height "H1" from the outer rim 140 to the lowermost portion 168 of the ventricular anchors 126 can range from about 10 mm to about 40 mm, and is about 23 mm in one example. The axial distance "H2" from the apex 162 of the ventricular anchor 126 to the lowermost portion 168 of the ventricular anchor 126 can range from about 10 mm to about 40 mm, and is about 18 mm in one example. The axial distance "H3" from the lower end 130 of the main body 122 to the lowermost portion 168 of the ventricular anchor 126 can range from about 0 mm to about 10 mm, and is about 5 mm in one example.

Some frame embodiments comprise more than two ventricular anchors. For example, a frame can have two or more ventricular anchors configured to attach to multiple locations along a single leaflet of a native valve. In some such embodiments (not shown), the frame can comprise two ventricular anchors that attach to the anterior mitral leaflet 10 and/or two ventricular anchors that attach to the posterior mitral leaflet 12. Ventricular anchors can also attach to other regions of the leaflets instead of, or in addition to, the A2 and P2 regions.

Figure 33:
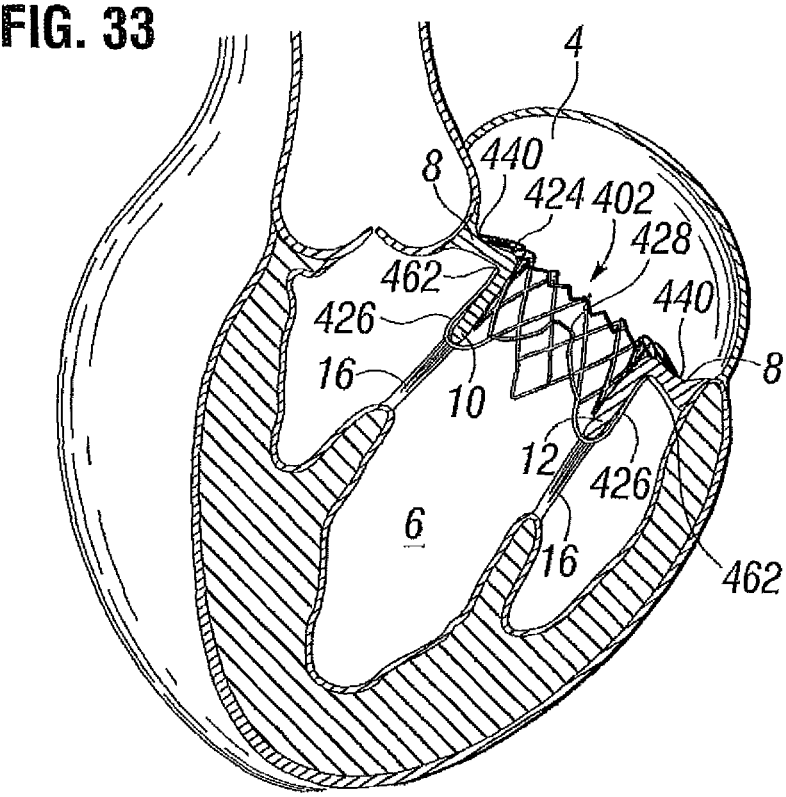
FIG. 33 is a cross-sectional view of the heart showing the frame of FIGS. 30-32 implanted in the mitral valve region.

Some prosthetic valve embodiments comprise four ventricular anchors spaced evenly apart around a main body. FIGS. 27-32 show one such prosthetic valve embodiment 400 comprising a frame 402 that comprises a pair of ventricular anchors 426 on diametrically opposed sides of a main body 422 and a pair of diametrically opposed commissure anchors 428 located about midway between the ventricular anchors 426. The ventricular anchors 426 extend downward from attachment points 456 and 458 and comprise a neck portion 450 (see FIG. 31). These ventricular anchors 426 can function similarly to the ventricular anchors 126 of the frame 102 to capture leaflets and retain the frame 402 within the mitral orifice, as shown in FIG. 33. The commissure anchors 428 can extend upward from the same attachment locations 456, 458 on the main body 422 (see FIG. 30). While the ventricular anchors 426 can clip the mitral leaflets 10, 12 at the A2 and P2 regions, respectively, the commissure anchors 428 can hook around and extend upward behind the mitral commissures 36, not compressing the leaflets. The apexes 464 of the commissure anchors 428 can extend upward to abut the ventricular side of the mitral annulus 8 and compress the mitral annulus 8 between the outer rim 440 of the atrial sealing member 424 and the apexes 464 of the commissure anchors 428. This compression of the mitral annulus 8 can provide additional retention against both atrial and ventricular movement.

Other frame embodiments can comprise more than four ventricular anchors. For example, a frame can comprise six or more ventricular anchors that can engage multiple locations on the leaflets 10, 12 and/or the commissures 36.

Figure 34:
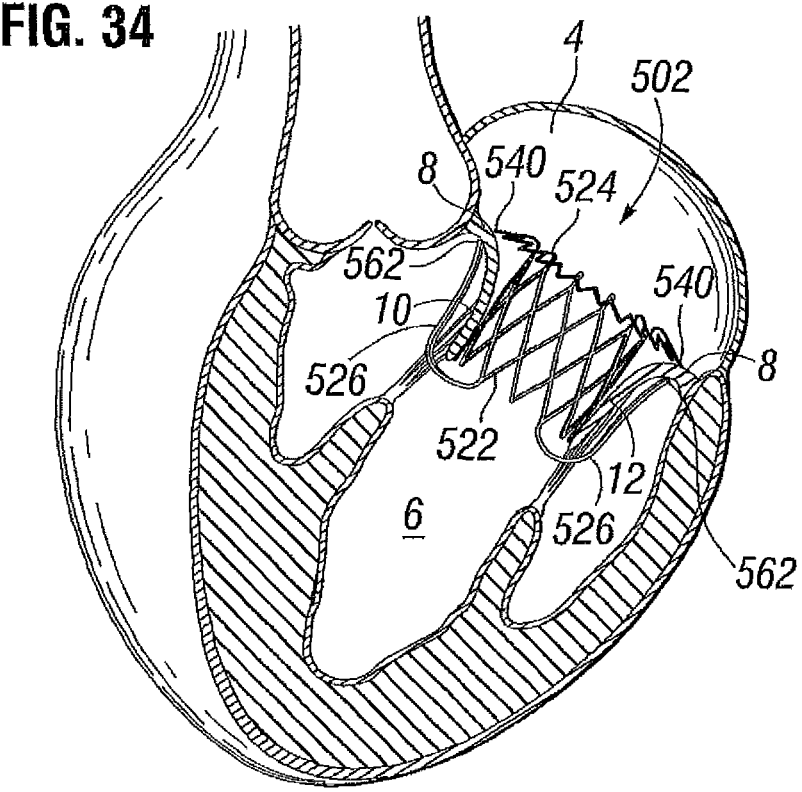
FIG. 34 is a cross-sectional view of the heart showing an embodiment of a frame, comprising extended ventricular anchors and an atrial sealing member, implanted in the mitral valve region such that the mitral annulus and/or native leaflets are compressed between the ends of the extended ventricular anchors and the atrial sealing member.

FIG. 34 shows a frame embodiment 502 that comprises extended ventricular anchors 526 that are configured to extend around the ends of the leaflets 10, 12 and extend upward behind the leaflets to locations proximate the outer rim 540 of a downwardly extending frustoconical atrial sealing member 524. The upper apexes 562 of the extended ventricular anchors 526 contact the ventricular surface of the mitral annulus 8 and/or portions of the native leaflets 10, 12 adjacent to the annulus, or annulus connection portions of the leaflets, while the outer rim 540 of the atrial sealing member 524 contacts the atrial surface of the mitral annulus and/or the annulus connection portions of the leaflets. The extended ventricular anchors 526 and the atrial sealing member 524 can be configured to oppose one another and desirably compress the mitral annulus 8 and/or annulus connection portions of the leaflets 10, 12 to retain the frame 502 from movement in both the atrial and ventricular directions. Thus, in this embodiment, the ventricular anchors 526 need not compress the native leaflets 10, 12 against the outer surface of the main body 522 of the frame. Instead, as shown in FIG. 34, the leaflets 10, 12 can be captured loosely between the extended ventricular anchors 526 and the outer surface of the main body 522.

Figure 35:
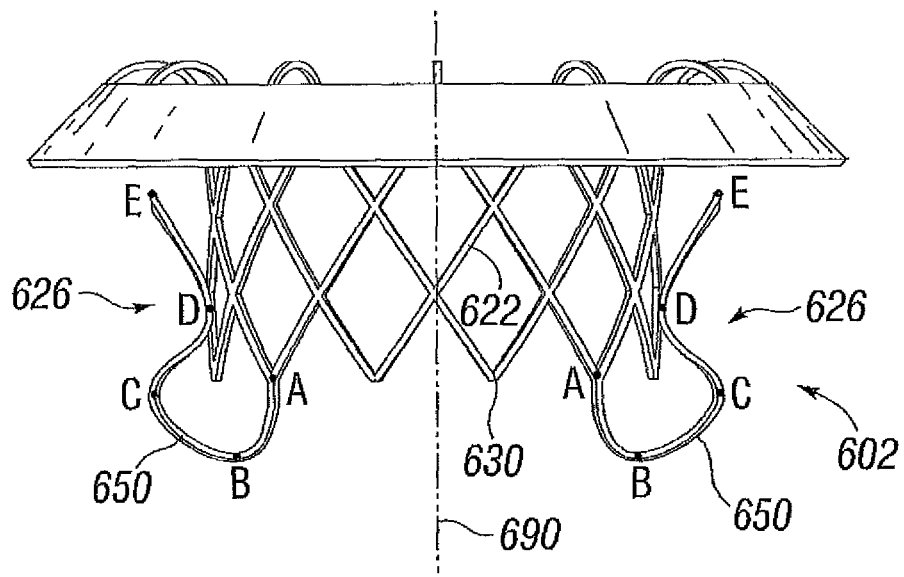
FIGS. 35 and 36 are side views of an exemplary embodiment of a frame comprising "S" shaped ventricular anchors.
Figure 36:
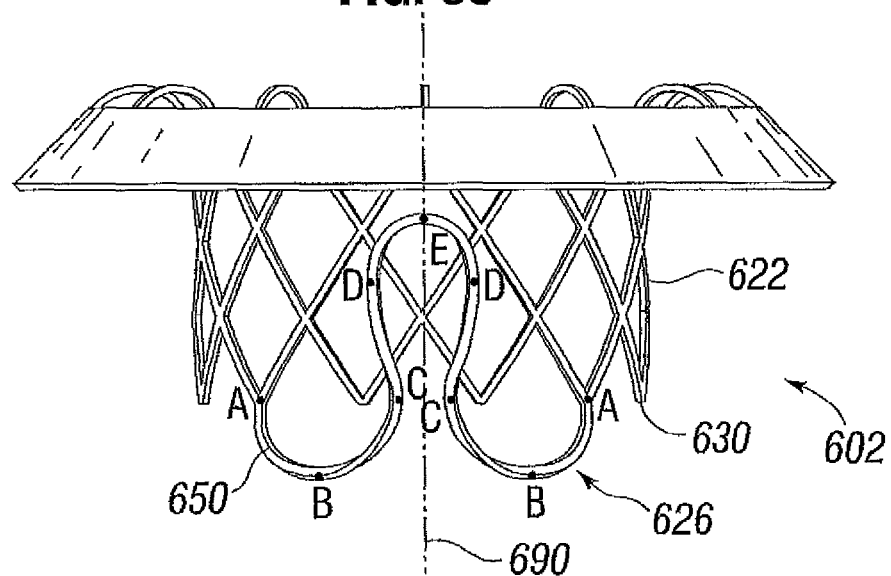

FIGS. 35 and 36 show a frame embodiment 602 comprising necked, "S" shaped ventricular anchors 626. From the side view of FIG. 35, the "S" shape of the ventricular anchors 626 is apparent. Starting from one attachment point A on the ventricular end 630 of the main body 622, the ventricular anchor wire 650 extends downward and radially outward from the main body to a point B, then curves upward and outward to a point C, then curves upward and inward to a point D, and then curves upward and back outward to an uppermost point, or apex, E. The ventricular anchor wire 650 then continues to extend back to the second attachment point following a similar, but mirrored path. From the frontal view of FIG. 36, the ventricular anchor wire 650 forms a necked shape that is symmetrical about a longitudinal center axis 690 extending through the center of the main body 622, forming two mirrored halves. Each half of ventricular anchor wire 650 begins at an attachment point A on the ventricular end 630 of the main body 622, curves downward and inward (toward the other half) to point B, then curves upward and inward to a necked portion at point C, then curves upward and outward (away from the other half) to a point D, then curves upward and inward again to an uppermost point, or apex, E where the two halves join together. Referring to FIG. 35, the radial distances from a longitudinal center axis 690 of the main body 622 to points C and E are both greater than the radial distances from the axis 690 to points D. Furthermore, the distance between the two points C is less than the distance between the two points D. The "S" shaped ventricular anchor 626 can help distribute stresses more evenly along the wire 650 and reduce stress concentrations at certain locations, such as the attachment points A.

Figure 37:
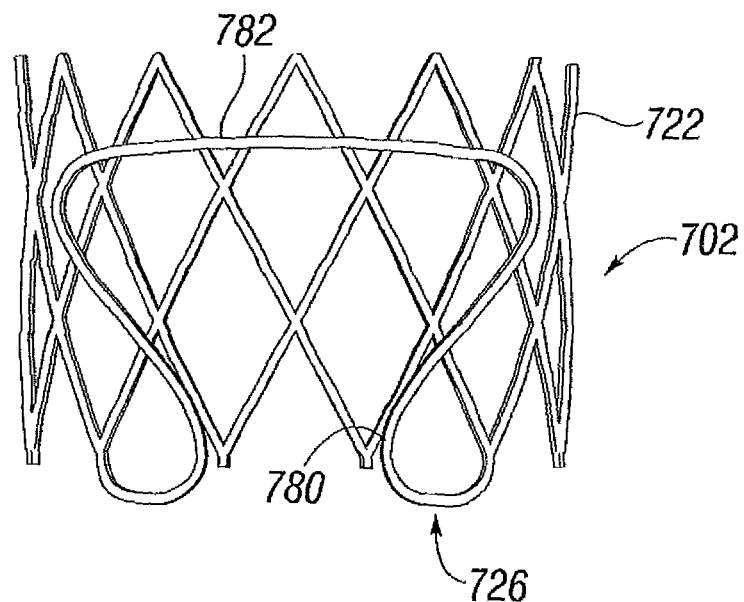
FIGS. 37 and 38 are side and top views, respectively, of an exemplary embodiment of a frame, with the atrial sealing member excluded, comprising wider shaped ventricular anchors.
Figure 38:
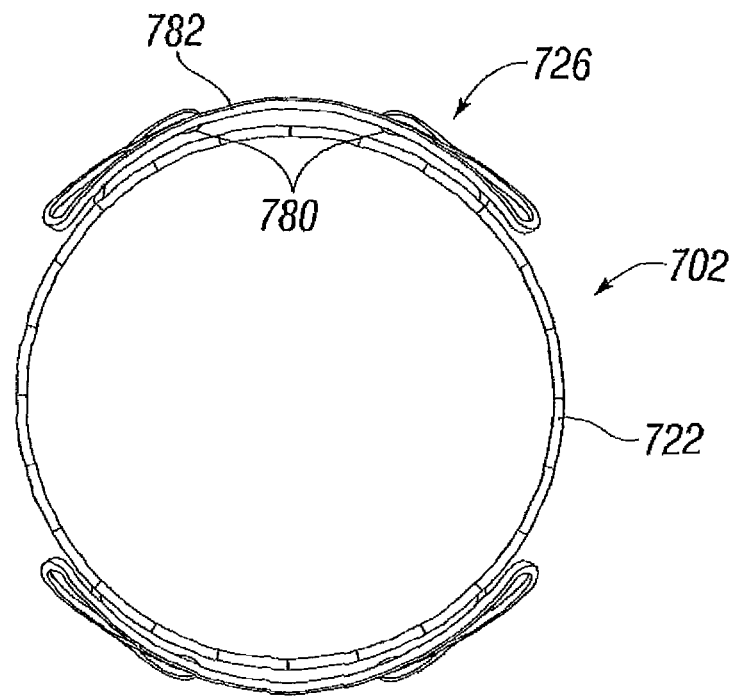

FIGS. 37 and 38 show a frame embodiment 702 that comprises two wider shaped ventricular anchors 726. Each wider shaped ventricular anchors 726 comprises a necked mid portion 780 and a broad upper portion 782. The upper portion 782 can extend generally parallel to the inflow opening of the frame 702 and can be curved around the outer surface of a main body 722. This wider shape can increase surface contact with the native leaflet and/or other cardiac tissue to reduce pressure and thereby reduce abrasion. In some embodiments, the broad upper portion 782 of the wider shaped ventricular anchors 726 can have a curvature that corresponds to the curvature of the outer surface of the main body 722 (see FIG. 38) to further improve tissue contact. The wider shaped ventricular anchor can have a longer surface contact with the atrial sealing member; thereby increasing retention performance and reducing paravalvular leak.

Figure 39:
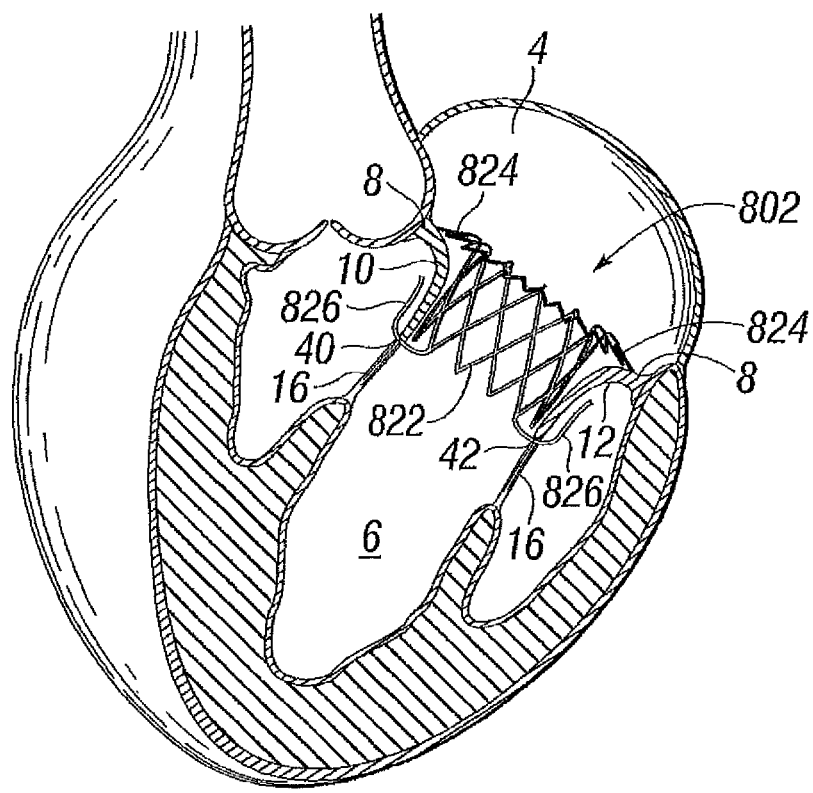
FIG. 39 is a cross-sectional view of the heart showing an embodiment of a frame implanted in the mitral valve region, wherein the ventricular anchors remain separated from the body of the frame after expansion and the ventricular anchors contact the lower ends of the mitral leaflets to utilize tension from the chordae tendineae to retain the frame.

FIG. 39 shows a frame embodiment 802 comprising ventricular anchors 826 that are configured to define a separation, or gap, between the anchors and the main body 822 even after the frame 802 expands (although the anchors 826 can otherwise function similar to ventricular anchors 126, such that the gaps between the anchors 826 and the frame main body 822 can increase and decrease upon compression and expansion of the main body, respectively, to facilitate placement of the anchors 826 behind the native leaflets). The gap can be sized to facilitate capturing the native leaflets 10, 12 with little or no compression of the native leaflets. Since little or no leaflet compression occurs, this frame embodiment 802 can minimize trauma to the native leaflets. Instead of compressing the leaflets 10, 12 for valve retention, the ventricular anchors 826 can hook the ventricular edges 40, 42 of the leaflets 10, 12, respectively, while an atrial sealing member 824 of the frame presses downwardly on the atrial side of the mitral valve annulus 8. The contact between the atrial sealing member 824 and the annulus 8 causes the main body 822 to shift slightly upwardly pulling the ventricular anchors 826 upwardly against the ventricular edges of the leaflets 10, 12. The upward force of the ventricular anchors in conjunction with downward tension on the leaflets from the chordae tendineae 16 restrain the implant from moving upward toward the left atrium 4.

Figure 40:
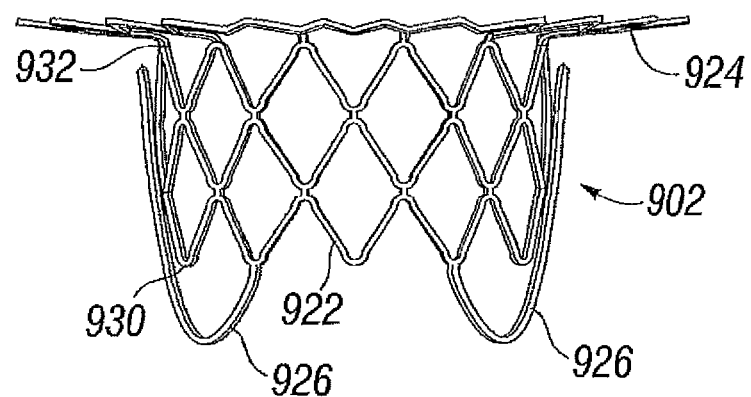
FIG. 40 shows an exemplary embodiment of a frame comprising a substantially flat atrial sealing member.

FIG. 40 shows a frame embodiment 902 that comprises a main body 922, ventricular anchors 926 and a disk-like atrial sealing member 924 that extends radially outward from the upper end 932 of the main body 922. In this embodiment, the atrial sealing member 924 extends substantially perpendicular to the frame opening defined by the upper and 932 rather than downwardly toward the frame's lower end 930. The disk-like atrial sealing member 924 can be positioned flat across the top surface of the mitral annulus 8 and provide increased surface area contact for tissue ingrowth.

Figure 41:
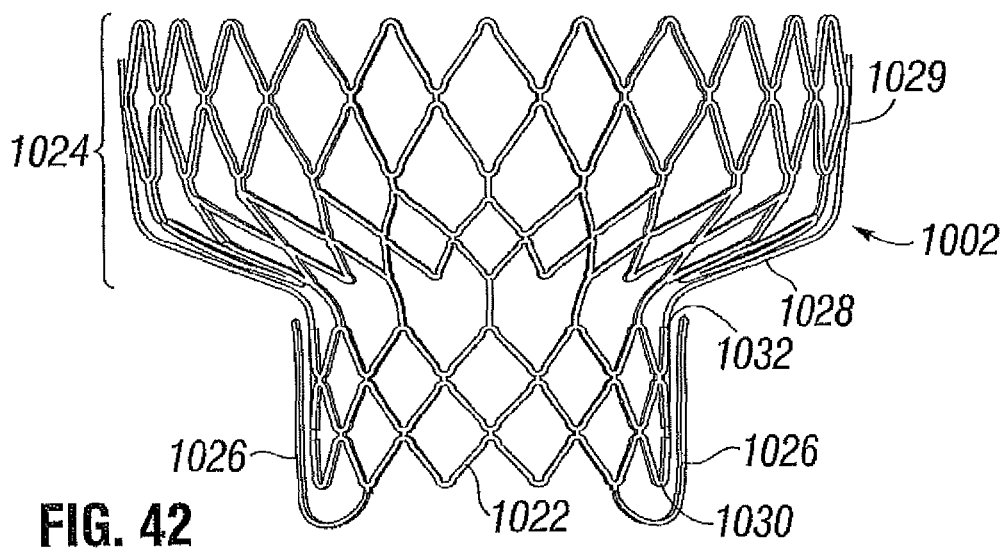
FIG. 41 shows an exemplary embodiment of a frame comprising an upwardly extending atrial sealing member.
Figure 42:
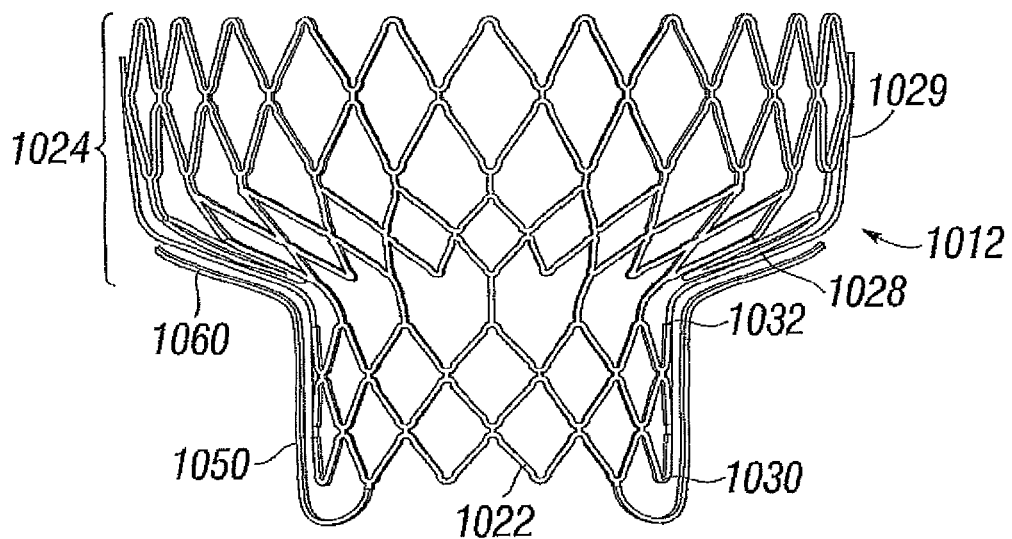
FIG. 42 shows an exemplary embodiment of a frame comprising an upwardly extending atrial sealing member and extended ventricular anchors.

FIGS. 41 and 42 show frame embodiments 1002 and 1012, respectively, that comprise an atrial sealing member 1024 having a generally frustoconical portion 1028 that extends from the upper end 1032 of a main body 1022 both radially outward and axially upward away from the main body. The atrial sealing member 1024 can also include a generally cylindrical upper, or inlet, portion 1029 that extends further upward from the frustoconical portion 1028 opposite the upper end 1032 of the main body 1022. The atrial sealing member 1024 can generally correspond to the shape of the atrial walls 18 adjacent to the mitral annulus 8 and provide for increased contact area between the atrial wall tissue and the atrial sealing member 1024. The frame 1002 includes ventricular anchors 1026 that extend from a ventricular end 1030 of the main body 1022 and along the majority of the length of the main body.

The frame 1012 shown in FIG. 42 comprises extended ventricular anchors 1050. The extended anchors 1050 can extend from the ventricular end 1030 of the main body 1022 along the outer surface of the main body and bend radially outward to form upper portions 1060 that extend along the lower surface of the frustoconical portion 1028. This configuration can allow the extended ventricular anchors 1050 to trap more of the leaflets 10, 12 and/or the mitral annulus 8 against the frame, thereby reducing paravalvular leakage and improving tissue ingrowth and retention.

Figure 43:
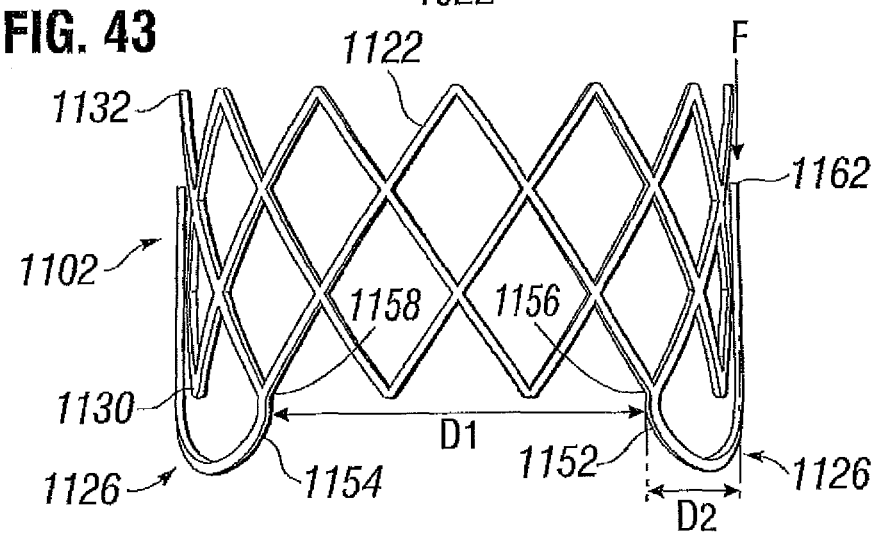
FIG. 43 shows an exemplary embodiment of a frame, with the atrial sealing member excluded, comprising wide-set ventricular anchors.

FIG. 43 shows a frame embodiment 1102 having ventricular anchors 1126 that have shorter moment arms D2 compared to the ventricular anchors 126 of the frame 102 shown in FIG. 9. The shorter moment arms D2 can result in reduced torque at the ventricular anchor attachment points 1156, 1158. The distance D2 can be reduced by increasing the distance D1 between the attachment points 1158 and 1156 on the main body 1122 of neighboring ventricular anchors 1126. The distance D1 between the ventricular anchors 1126 of the frame 1102 is greater than the distance D1 between the attachment points 158 and 156 of frame 102 (see FIG. 9), thus shortening the moment arm D2 of the force F relative to the attachment point 1156. The reduced torque at the attachment points 1156 and 1158 can reduce fatigue and thus improve the durability of the frame 1102.

Some embodiments of ventricular anchors can optionally also comprise one or more barbs (not shown) that can protrude radially from a ventricular anchor toward the ventricular walls 20 or toward the leaflets 10, 12. Such barbs can help retain a frame, particularly against movement towards the left ventricle 6.

Figure 44:
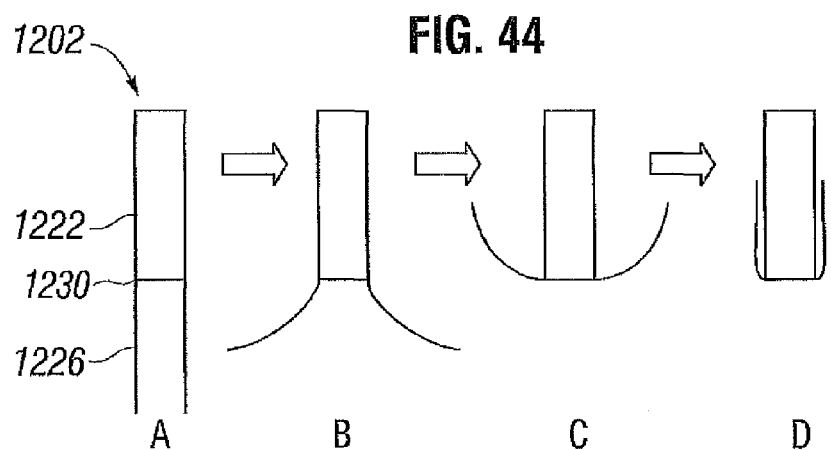
FIG. 44 depicts a series of side views of an exemplary embodiment of a frame, with the atrial sealing member excluded, having ventricular anchors that flip up into a final configuration.

FIGS. 44A-44D illustrate a frame embodiment 1202 comprising "flip-up" ventricular anchors 1226. Each ventricular anchor 1226 can be finger-like and can extend from only one attachment point on the lower end 1230 of the main body 1222. Alternatively, each ventricular anchor can comprise a wire or similar element that extends from two attachment points on the main body 1222. In the illustrated embodiment, the ventricular anchors 1226 can be pre-formed to extend along the outer side of the main body 1222 in the functional, deployed state, as shown in FIG. 44D. During delivery, the ventricular anchors 1226 can be partially or completely straightened, as shown in FIG. 44A, and retained in that state by a delivery device, such as a sheath. As the frame 1202 is advanced from the sheath, for example, the ventricular anchors 1226 spring back to their pre-formed shape, as shown in FIGS. 44B-44D, capturing the leaflets 10, 12 between the ventricular anchors 1226 and the main body 1222.

Figure 45:
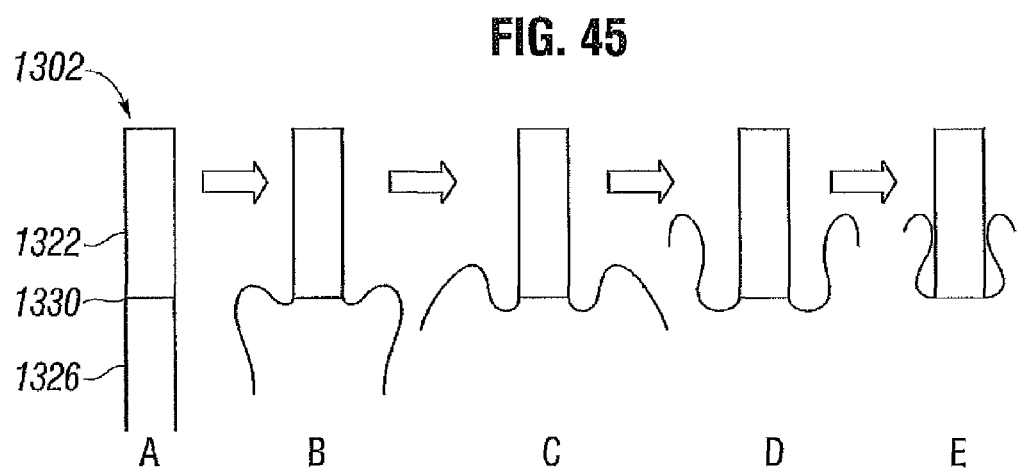
FIG. 45 depicts a series of side views of an exemplary embodiment of a frame, with the atrial sealing member excluded, having ventricular anchors that curl up into a final configuration.

FIGS. 45A-45E represent a frame embodiment 1302 comprising "curl-up" ventricular anchors 1326. As with the ventricular anchors 1226 of FIG. 44, each ventricular anchor 1326 can be finger-like and can extend from two or more points on lower end 1330 of the main body 1322. The ventricular anchors 1326 can be pre-formed in a curved shape, as shown in FIG. 45E, that extends along the side of the main body 1322 in the deployed state. During delivery, the ventricular anchors 1326 can be partially or completely straightened, as shown FIG. 45A, and retained in that state by a delivery device, such as a sheath. As the frame 1302 is advanced from the sheath, for example, the ventricular anchors 1326 are allowed to spring back to their pre-formed curved shape, as shown in FIGS. 45B-45E, capturing the leaflets 10, 12 between the ventricular anchors 1326 and the main body 1322.

Figure 46A:
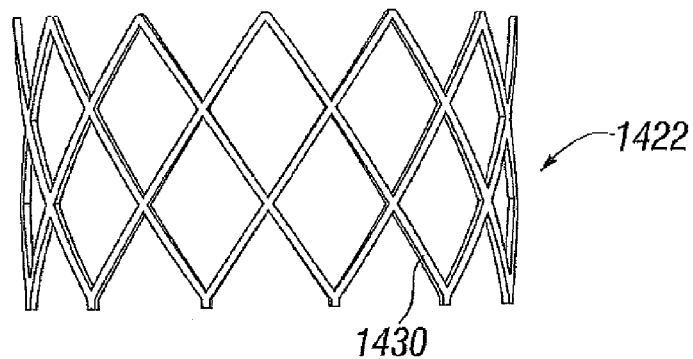
FIGS. 46A-46C show an exemplary embodiment of a frame, with the atrial sealing member excluded, wherein the main body is manufactured separately from the ventricular anchors.
Figure 46B:
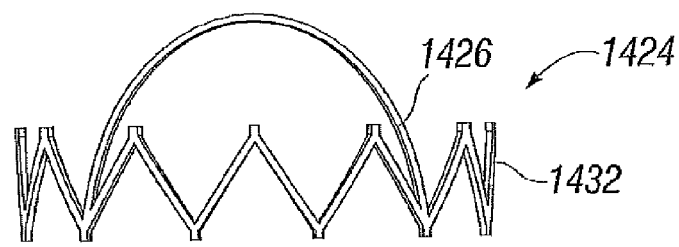
Figure 46C:
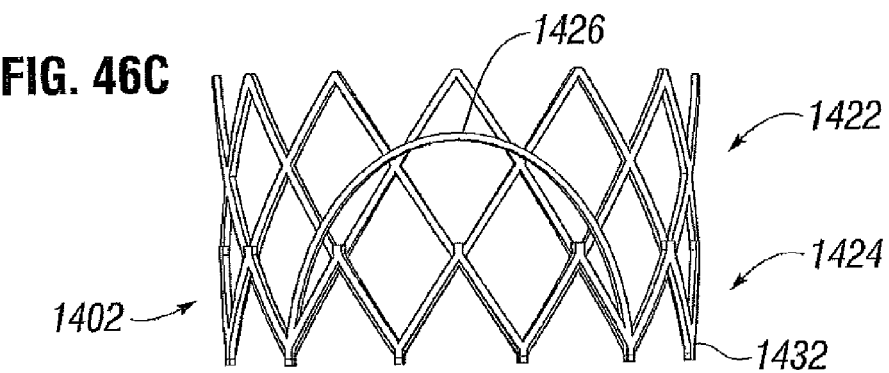
Figure 47A:
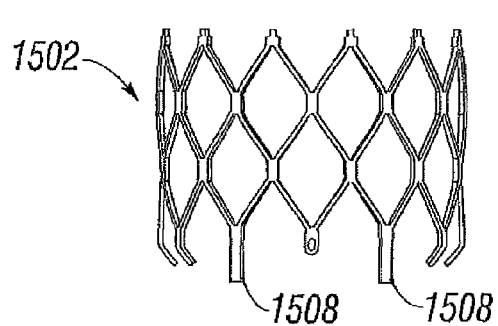
FIGS. 47A-47D show another embodiment of a frame, with the atrial sealing member excluded, wherein the main body is manufactured separately from the ventricular anchors and attached using a sleeve.
Figure 47B:
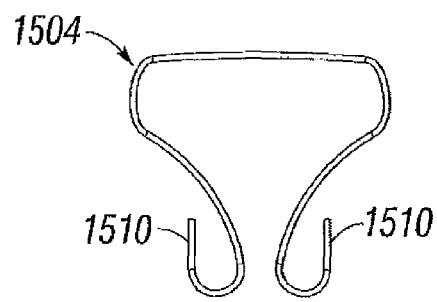
Figure 47C:
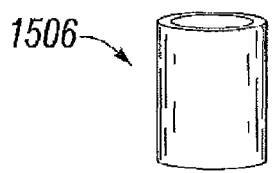
Figure 47D:
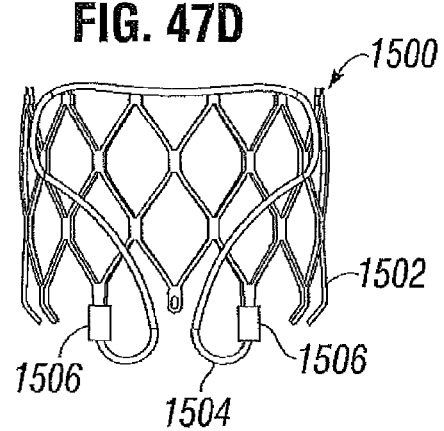

In some frame embodiments, one or more ventricular anchor components can be formed separately from the main body and later assembled together to form a frame. In one such frame embodiment 1402, as shown in FIGS. 46A-46C, a main body 1422 is formed separately from at least one ventricular anchor portion 1424. The ventricular anchor portions 1424 can comprise one or more ventricular anchors 1426 extending from an at least partially annular base 1432, which can comprise side-by-side "V" shaped strut portions connected together at their upper ends. The lower ends of the ventricular anchors 1426 in the illustrated embodiment are connected to the base 1432 at the lower vertexes of the "V" shaped portions. After the main body and the ventricular anchor portions are separately formed, the ventricular anchor portions 1424 can be attached to the lower portion 1430 of the main body 1422. For example, the bases 1432 can be placed on opposite sides of the outer surface of the main body 1422 and then sewn, welded, or otherwise attached to the lower portion 1430 of the main body 1422 in a suitable manner, such as by using a locking mechanism. The bases 1432 can be attached to the main body 1422 such that the "V" shaped portions of the bases overlap with corresponding "V" shaped portions of the lower end 1430 of the main body 1422. In some embodiments, the ventricular anchor portion 1424 can comprise a complete ring having all of the ventricular anchors 1426 extending from one annular base such that the ventricular anchors are pre-spaced relative to one another. The annular base can then be attached around the lower end 1430 of the main body 1422. In other embodiments, multiple ventricular anchor portions 1424, each having one or more ventricular anchors 1426 extending from a respective base 1432 comprising a partial ring, are secured to the main body 1422.

Figure 48A:
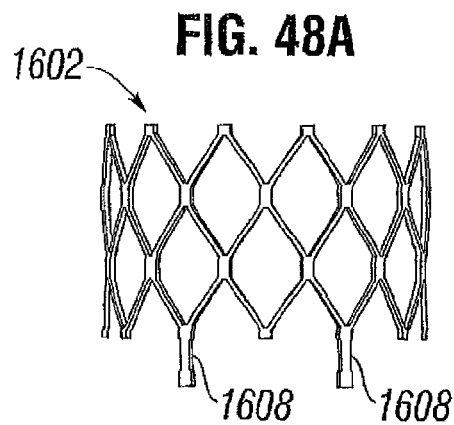
FIGS. 48A-48C show another embodiment of a frame, with the atrial sealing member excluded, wherein the main body is manufactured separately from the ventricular anchors and attached using a sleeve with a mechanical lock.
Figure 48B:
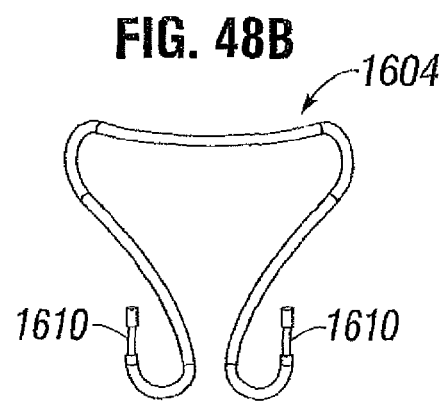
Figure 48C:
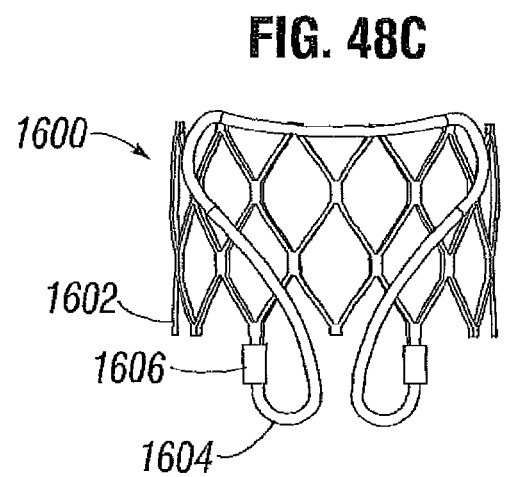

FIGS. 47A-47D and FIGS. 48A-48C show alternative frame embodiments wherein one or more ventricular anchor components are formed separately from a main body and later assembled together to form a frame. In these frame embodiments, the main body can comprise attachment portions to which anchor portions can be attached using sleeves. For example, FIGS. 47A-47D show an exemplary frame 1500 comprising a main body 1502 having at least two ventricular anchor attachment portions 1508 and at least one ventricular anchor 1504 having two attachment portions 1510 connected to respective attachment portions 1508 with respective sleeves 1506. Similarly, FIG. 48A-48C show an exemplary frame 1600 comprising a main body 1602 having at least two ventricular anchor attachment portions 1608 and at least one ventricular anchor 1604 having two attachment portions 1610 connected to respective attachment portions 1608 with respective sleeves 1606. The sleeves can comprise, for example, a metal material, such as Nitinol, having superelastic and/or shape-memory characteristics. In some embodiments, the sleeves can comprise metal of an anneal state suitable for a crimping process. The sleeves can be attached to the anchor portions and to the attachment portions of the main body by any suitable attachment means, such as by welding. As shown in FIGS. 48A-48C, the attachment portion 1610 of the anchors 1604 and the attachment portions 1608 of the main body 1602 can comprise geometric features, such as narrow regions, or cut-outs, which allow the sleeves 1606 to integrate the anchor portions 1604 to the main body 1602, such as by forming a mechanical lock.

Multi-part construction of a frame, as shown in FIG. 46-48, can reduce strain and fatigue at the ventricular anchor attachment locations compared to a unibody, or one-piece, construction. By contrast, in some embodiments comprising a unibody construction, the ventricular anchors are initially laser cut and expanded such that they extend downward from the lower end of the main body, and are then formed, or bent, to a desired configuration adjacent to the outside of the main body of the frame. Such bending can strain and weaken the bent portion.

To avoid strain caused by plastic deformation of the ventricular anchors, the ventricular anchors can be pre-formed in a desired implantation (deployed) shape without plastically bending the ventricular anchors. The ventricular anchors can then be elastically deformed, such as straightened and/or compressed, to fit into a delivery device for delivery through the body to the mitral valve region of the heart. The deformed ventricular anchors can resiliently regain their pre-formed shape once freed from the axial constraint of a delivery device to facilitate capturing the leaflets 10, 12 between the ventricular anchors and the main body of the frame.

Figure 70:
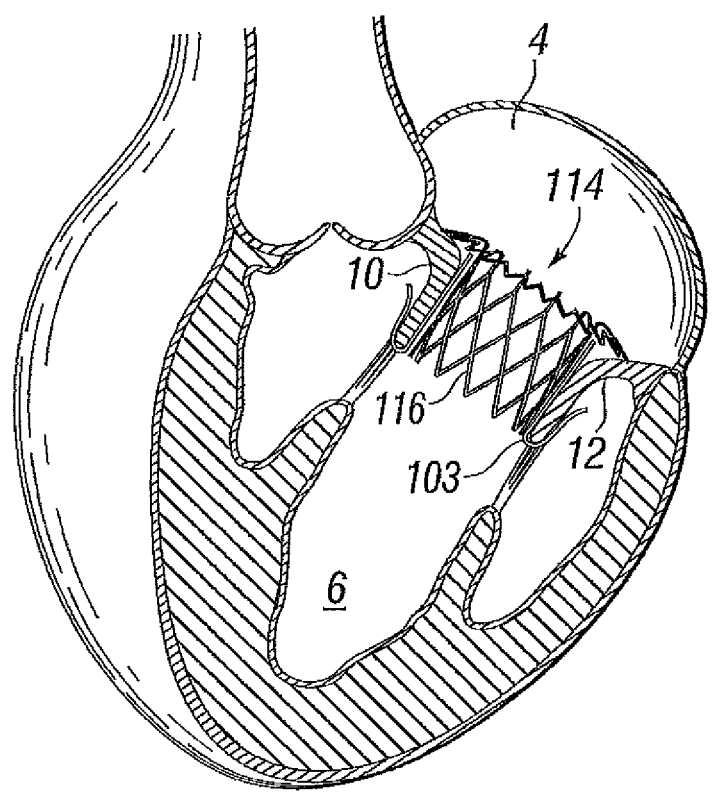
FIG. 70 is a cross-sectional view of the heart showing an embodiment of a docking frame that is secured to the native tissue of mitral valve region and a separately deployed prosthetic valve that is secured to the docking frame within the lumen of the docking frame.

Any of the various embodiments of frames described above can be combined with a fluid-occluding member, such as valve structure 104, to form a fully assembled prosthetic valve that can be implanted within the native mitral valve. In other embodiments, any of the frames described above can be provided without a fluid-occluding member and can be used as a scaffolding or docking structure for receiving a separate prosthetic valve in a two-stage delivery process. With reference to the exemplary embodiment shown in FIG. 70, a docking frame 103 (which can have a construction similar to the frame 102) can be deployed first, for example by any of the anchoring techniques discussed above. Then, a separate prosthetic valve 114 can be delivered and deployed within the lumen formed by the previously deployed docking frame 103. The separate prosthetic valve 114 desirably comprises a radially compressible and expandable frame 116 that mounts a fluid-occluding member (not shown in FIG. 70), such as the valve structure 104 (see FIG. 7) having a plurality of leaflets 106. When expanded inside the docking frame 103, the frame 116 of the prosthetic valve 114 engages the inside surface of the docking frame 103 so as to retain, such by friction or mechanical locking feature, the prosthetic valve 114 within the docking frame 103. Examples of prosthetic valves that can be used in such a two-stage process are disclosed in U.S. Pat. No. 7,510,575, which is incorporate herein by reference. In particular embodiments, the prosthetic valve can comprise any of various transcatheter heart valves, such as the Sapien valve, available from Edwards Lifesciences LLC (Irvine, Calif.).

The technique of capturing the leaflets 10, 12 between a ventricular anchor and the main body of a frame, such as shown in FIG. 23, can provide several advantages. First, this can allow for anchoring onto the native leaflets 10, 12 for retention within the mitral valve region. Second, this technique can utilize the native chordae 16 for retention. Third, this technique can prevent the anterior leaflet 10 from being "pulled" toward the aortic valve 14 when the left ventricle 6 contracts and blood rushes out through the aortic valve (systolic anterior motion). Fourth, this technique tends to force the native leaflets 10, 12 to collapse around the main body of the frame, which can reduce leakage between the outside of the prosthetic valve 100 and the native mitral valve 2. Fifth, this technique allows for implantation from either the left atrium 4 or from the left ventricle 6, as described in detail below.

As described above, various frame embodiments can utilize one or more anchoring techniques other than compressing the leaflets 10, 12 to retain the prosthetic valve 100 in a desired position within the mitral valve orifice. These anchoring techniques can include, for example, utilizing tension of the native chordae 16, extending the ventricular anchor length such that the apex of the ventricular anchor is pressed up against the mitral annulus 8 so as to form a stop, and compressing the mitral annulus 8 and/or atrial tissue between the apex of an ventricular anchor and the outer rim of an atrial sealing member of the frame.

Delivery Approaches

The various methods and apparatus described hereinafter for delivery and implantation at the native mitral valve region are described with respect to the prosthetic valve 100, though it should be understood that similar methods and apparatus can be used to deliver and/or implant a component of the prosthetic valve 100, such as the frame 102 without the valve structure 104, or other prosthetic apparatus.

The prosthetic valve 100 can be delivered to the mitral valve region from the left ventricle 6 or from the left atrium 4. Because of the anatomy of the native mitral valve 2, different techniques and/or equipment can be used depending on the direction the prosthetic valve 100 is delivered.

Figure 57:
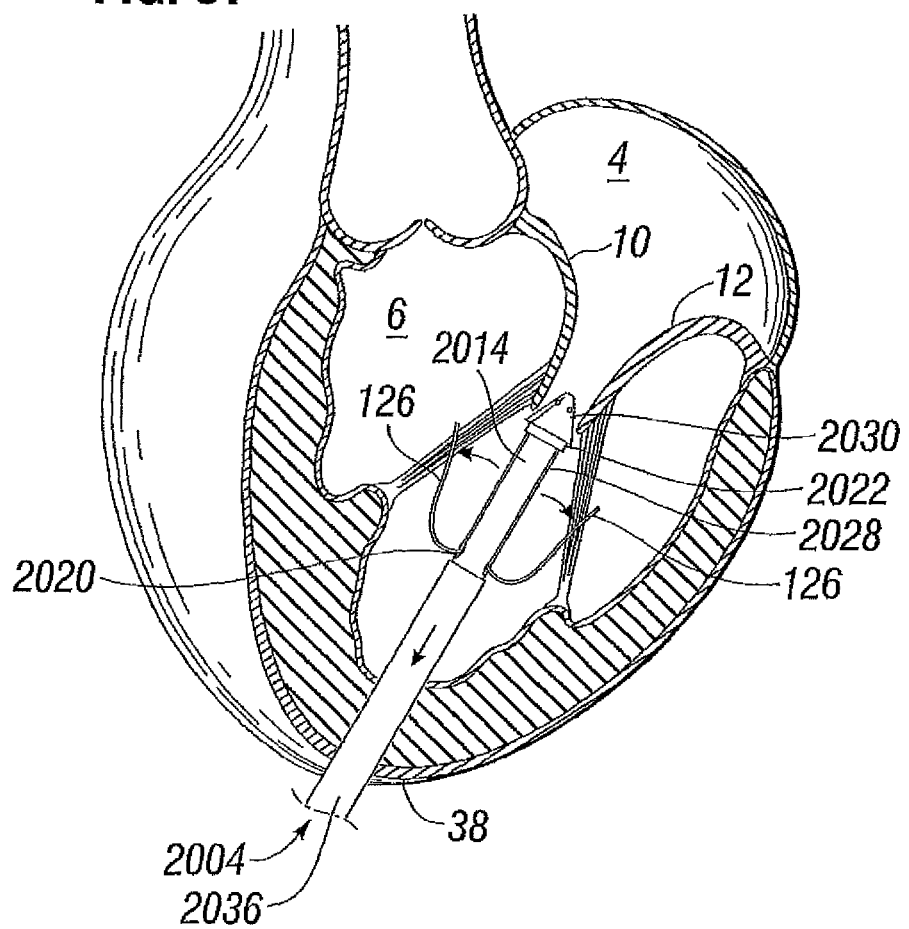
FIG. 57 is a cross-sectional view of the heart showing the ventricular anchors of the prosthetic valve being pre-deployed in the left ventricle using the delivery system of FIG. 49.

Delivery from the ventricular side of the mitral annulus 8 can be accomplished in various manners. For example, the prosthetic valve 100 can be delivered via a transapical approach in which access is made to the left ventricle 6 via the heart apex 38, as shown in FIG. 57.

Figure 66:
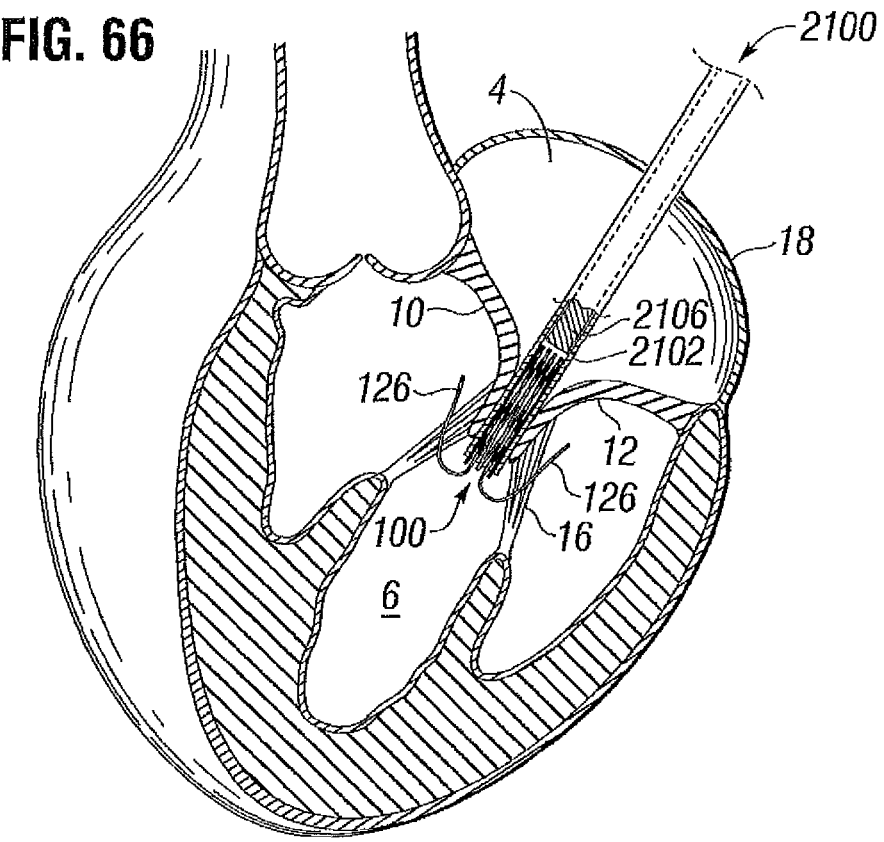
FIG. 66 is a cross-sectional view of the heart showing the prosthetic valve of FIG. 65 being implanted in the native mitral valve region using a transatrial approach.
Figure 67:
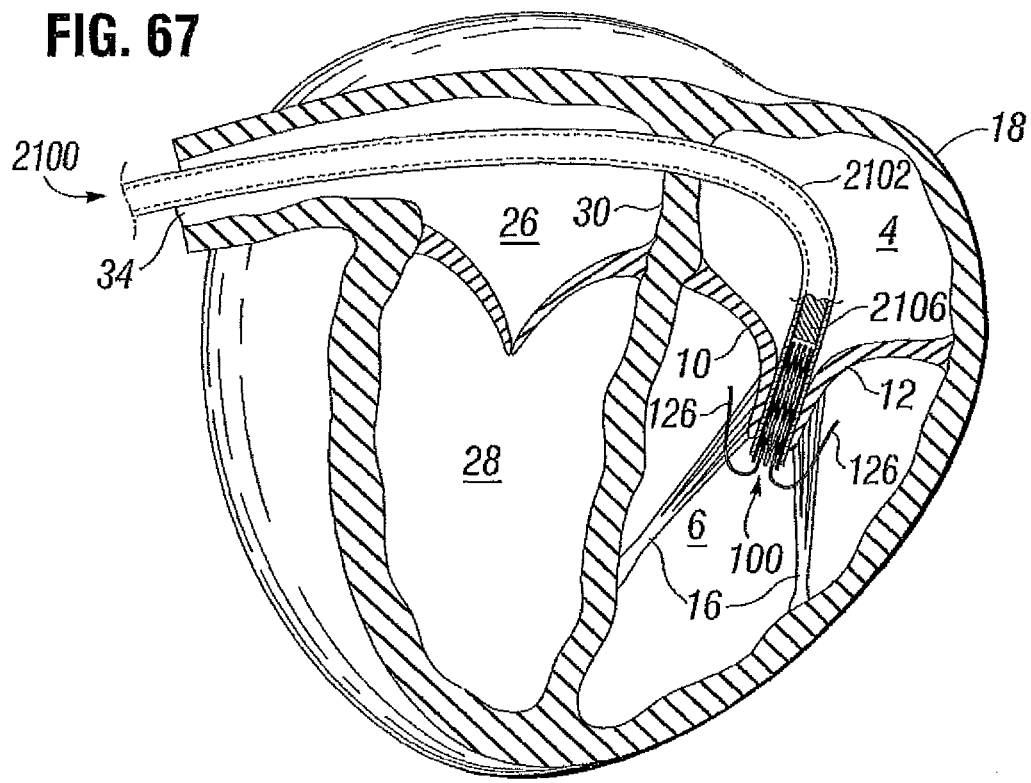
FIG. 67 is a cross-sectional view of the heart showing the prosthetic valve of FIG. 65 being implanted in the native mitral valve region using a transeptal approach.

Delivery from the atrial side of the mitral annulus 8 can also be accomplished in various manners. For example, a transatrial approach can be made through an atrial wall 18, as shown in FIG. 66, for example by an incision through the chest. An atrial delivery can also be made from a pulmonary vein 32 (see FIG. 1). In addition, atrial delivery can be made via a transeptal approach, as shown in FIG. 67, wherein an incision is made in the atrial portion of the septum 30 to allow access from the right atrium 26, such as via the inferior or superior vena cava 34.

Ventricular Approaches

One technique for delivering a compressed prosthetic apparatus, such as the prosthetic valve 100, to the mitral valve region includes accessing the native mitral valve region from the left ventricle 6, one example being the transapical approach. Alternatively, access to the left ventricle 6 can be made through the aortic valve 14. In the transapical approach, access to the left ventricle 6 can be made through an incision in the chest and an incision at the heart apex 38, as shown in FIG. 57. A transapical delivery system can be used with the transapical approach.

FIGS. 49-53 show an exemplary transapical delivery system, or delivery tool, 2000 that is configured to deliver and implant the prosthetic valve 100. The delivery system 2000 can comprise a series of concentric shafts and sheaths aligned about a central axis and slidable relative to one another in the axial directions. The delivery system 2000 can comprise a proximal handle portion 2002 for physician manipulation outside of the body while a distal end portion, or insertion portion, 2004 is inserted into the body.

The delivery system 2000 can comprise an inner shaft 2006 that runs the length of the delivery system and comprises a lumen 2008 through which a guidewire (not shown) can pass. The inner shaft 2006 can be positioned within a lumen of a pusher shaft 2010 and can have a length that extends proximally beyond the proximal end of the pusher shaft and distally beyond the distal end of the pusher shaft. The delivery system 2000 can comprise an annular space 2012 between the outer surface of the inner shaft 2006 and the inner surface of the pusher shaft 2010. This annular space can be used for flushing with saline or for allowing blood to be expelled distally.

The delivery system 2000 further comprises an inner sheath 2014 positioned concentrically around at least a distal portion of the pusher shaft 2010. The inner sheath 2014 is axially slidable relative to the pusher shaft 2010 between a delivery position (see FIG. 55) and a retracted position (see FIG. 50). In the delivery position, a distal end portion 2016 of the inner sheath 2014 is positioned distal to a distal end, or pusher tip 2018, of the pusher shaft 2010. In the delivery position, the distal end portion 2016 of the inner sheath 2014 forms an inner cavity that can contain a compressed prosthetic valve 100. In the retracted position (see FIG. 50), the distal end 2017 of the inner sheath 2014 is positioned proximal to or aligned axially with the pusher tip 2018. As the inner sheath 2014 moves from the delivery position toward the retracted position (either by retracting the inner sheath 2014 proximally relative to the pusher shaft 2010 or advancing the pusher shaft distally relative to the inner sheath), the pusher tip 2018 can force the prosthetic valve 100 out of the distal end portion 2016 of the inner sheath.

As shown in FIG. 50, the inner sheath 2014 comprises one or more longitudinally disposed slots 2028 extending proximally from a distal end 2017 of the inner sheath. These slots 2028 can allow ventricular anchors 126 of a prosthetic valve 100 contained within the inner sheath 2014 to extend radially outward from the compressed main body of the prosthetic valve while the main body is retained in the compressed state within the inner sheath. In the embodiment shown in FIG. 50, two slots 2028 are shown oriented on diametrically opposed sides of a longitudinal central axis of the inner sheath 2014. This embodiment corresponds to the prosthetic valve 100, which comprises two opposed ventricular anchors 126. In other embodiments, the inner sheath 2014 can comprise a different number of slots 2028, for example four slots, that correspond to the number and location of ventricular anchors on a selected prosthetic valve. In some embodiments, such as shown in FIG. 50, the proximal end portion 2020 of the each slot 2028 comprises a rounded opening that has a greater angular width than the rest of the slot.

A break-away, or frangible, retaining band 2022 can be positioned around the distal end portion 2016 of the inner sheath 2014, as shown in FIG. 50. The band 2022 can help retain the distal end portion 2016 of the inner sheath 2014 from splaying apart from the force of a compressed prosthetic valve 100 contained within the inner sheath 2014. The band 2022 comprises a proximal edge 2024 that can comprise at least one notch 2026 located over a slot 2028 in the inner sheath 2014. The band 2022 can comprise a frangible material and can be configured to tear or break apart at the notch location when a sufficient axial force is applied at the notch 2026. In use, the band 2022 is configured to break at notches 2026 under the force of the ventricular anchors 126 of the valve 100 as it is deployed from the inner sheath 2014, as further described below.

An outer sheath 2036 is positioned concentrically around a portion of the inner sheath 2014 and is slidable axially relative to the inner sheath. The outer sheath 2036 can be positioned to cover at least a portion of the distal end portion 2016 of the inner sheath 2014. In such a covered position, such as shown in FIG. 55, the ventricular anchors can be contained between the inner and outer sheath. The outer sheath 2036 is in this covered position while the loaded delivery system 2000 is inserted through the body and into the left ventricle 6. The outer sheath 2036 can be retracted proximally relative to the sheath 2014 to uncover the slots 2028 and allow the ventricular anchors 126 to spring outward through the slots in the inner sheath 2014 during deployment. Alternatively, the inner sheath 2014 can be advanced distally relative to the outer sheath 2036 to uncover the slots 2028.

With reference to FIG. 51, the handle portion 2002 of the delivery system 2000 can comprise components that facilitate sliding the inner sheath 2014 and the outer sheath 2036 back and forth along their respective ranges of axial movement to load, deliver, and deploy the prosthetic valve 100. An outer sheath grip 2052 can be attached to the proximal end of the outer sheath 2036. A physician can grasp the outer sheath grip 2052 and push or pull the outer sheath 2036 proximally or distally relative to the rest of the delivery system 2000. The outer sheath can also be mounted on a lead screw (not shown). The handle portion 2002 of the delivery system 2000 can further comprise a housing 2054 that provides a hand grip or handle for the physician to hold the delivery system 2000 steady while she uses the other hand to actuate the sheaths. A sliding lead screw 2056 can be fixed (e.g., bonded, mechanically locked, etc.) to a proximal end portion 2058 of the inner sheath 2014 and be positioned within the housing 2054. The lead screw 2056 can be fixed rotationally relative to the housing 2054 and can be constrained to an axial sliding range within the housing. A rotatable sleeve 2060 can be positioned concentrically between the outer housing 2054 and the inner lead screw 2056 and can comprise a proximal knob portion 2062 that extends free of the housing 2054 to provide a hand grip for the physician to rotate the rotatable sleeve 2060. The rotatable sleeve 2060 can be free to rotate relative to the housing 2054, but be fixed axially relative to the housing. The lead screw 2056 can comprise an outer helical groove 2064 that interacts with inwardly projecting ridges 2066 on the rotatable sleeve 2060 such that when the knob 2062 is rotated relative to the lead screw 2056 and the housing 2054, the ridges 2066 cause the lead screw 2056 to slide axially, thereby causing the inner sheath 2014 to also slide axially. Thus, the physician can move the inner sheath 2014 proximally by rotating the knob 2062 one direction relative to the housing 2054 and distally by rotating the knob the opposite direction relative to the housing. The housing 2054 can be fixed relative to the pusher shaft 2010 such that when the knob 2062 is rotated relative to the housing, the lead screw 2056 and the inner sheath 2014 slide axially together relative to the pusher shaft 2010 and the housing 2054.

As shown in FIG. 51, the inner shaft 2006 passes all the way through the handle portion 2002 of the delivery system 2000 and the pusher shaft 2010 can terminate at or near a proximal end cap 2068 of the handle portion 2002. The annular space 2012 between the outer surface of the inner shaft 2006 and the inner surface of the pusher shaft 2010 (see FIGS. 52 and 53) can be fluidly connected to at least one flushing port 2070 in the end cap 2068 of the handle portion 2002. The flushing port 2070 can provide access to inject fluid into the annular space 2012 and/or allow fluid to escape from the annular space.

As shown in FIG. 49, a nose cone 2030 can be attached to the distal end of the inner shaft 2006. The nose cone 2030 can be tapered from a proximal base 2034 to a distal apex 2032. The base 2034 can have a diameter about equal to the diameter of the outer sheath 2036. The nose cone 2030 can be retracted proximally, by sliding the inner shaft 2006 proximally relative to the rest of the delivery system 2000, to mate against the distal end of the outer sheath 2036 and/or the inner sheath 2014 to further contain the compressed prosthetic valve 100, as shown in FIG. 55. The nose cone 2030 can also be moved distally away from the sheaths to provide space for the prosthetic valve 100 to be loaded and/or deployed. During insertion of the delivery system 2000 through the body, the tapered nose cone 2030 can act as a wedge to guide the insertion portion 2004 of the delivery system 2000 into the body and provides an atraumatic tip to minimize trauma to surrounding tissue as the delivery system is advanced through the body.

Figure 56:
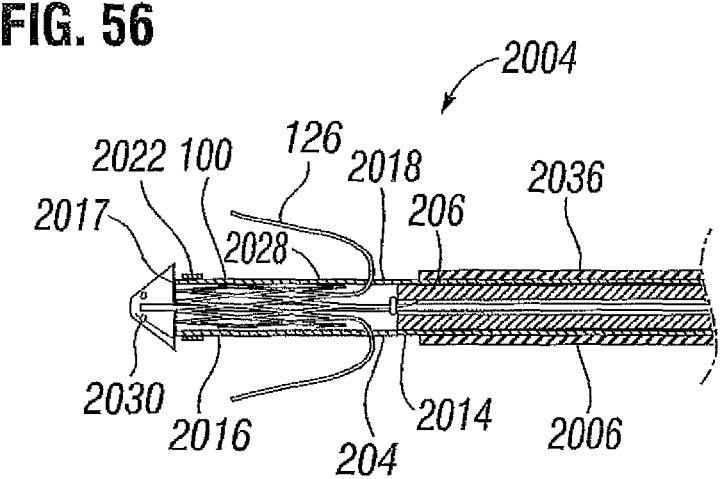
FIG. 56 is a cross-sectional view of a distal end portion of the delivery system of FIG. 49 showing the outer sheath of the delivery system retracted such that ventricular anchors extend outward through slots of the inner sheath.

To load the prosthetic valve 100 into the delivery system 2000, the nose cone 2030 must be moved distally away from the sheaths and the inner sheath 2014 must be advanced distally to the delivery position, as shown in FIG. 54 (without retaining band 2022). The outer sheath 2036 can be retracted to expose the slots 2028 in the inner sheath 2014. The prosthetic valve 100 is then positioned between the nose cone 2030 and the inner sheath 2014 and around the inner shaft 2006. The prosthetic valve 100 is then compressed to the compressed state and slid into the inner sheath 2014 such that the proximal, or lower, end of the prosthetic valve is adjacent to or contacting the pusher tip, as shown in FIG. 56. A loading cone or equivalent mechanism can be used to insert the valve 100 into the inner sheath 2014. In embodiments of the prosthetic valve 100 comprising a pusher member 204, such as in FIG. 25, the bottom end 206 of the pusher member 204 can contact the pusher tip 2018, as shown in FIG. 56. The ventricular anchors 126 can be allowed to extend out through the rounded proximal end portions 2020 of the respective slots 2028, as shown in FIG. 54. The proximal end portion 2020 of each slot can have sufficient angular width to allow the two end portions of the ventricular anchor 126 to reside side-by-side within the slot, which can cause the intermediate portion of the ventricular anchor to assume a desired shape for implanting behind the leaflets 10, 12. The break-away retaining band 2022 can be placed around the distal end portion of the inner sheath 2014 such that each notch 2026 in the band 2022 is located over a respective slot, as shown in FIG. 50. The outer sheath 2036 is then advanced distally to cover the slots 2028, as shown in FIG. 55, thereby compressing the ventricular anchors 126 and constraining the ventricular anchors within the outer sheath 2036. Alternatively, the prosthetic valve can be inserted into the inner sheath 2014 while the outer sheath 2036 is covering the slots 2028, such that the ventricular anchors 126 are positioned in the slots, but cannot extend out of the slots. The ventricular anchors 126 can also be constrained between the outer surface of the inner sheath 2014 and inner surface of the outer sheath 2036. In any case, the ventricular anchors 126 are free to spring radially outward once the outer sheath 2036 is retracted. After the prosthetic valve 100 is within the inner sheath 2014, the inner shaft 2006 can be retracted to pull the nose cone 2030 against the distal end of the inner sheath 2014 and/or the outer sheath 2036, as shown in FIG. 55. With the prosthetic valve 100 within the inner shaft 2006, the nose cone 2030 retracted and the outer sheath 2036 constraining the ventricular anchors 126, the delivery system 2000 is in the loaded configuration and ready for insertion into the body.

Figure 58:
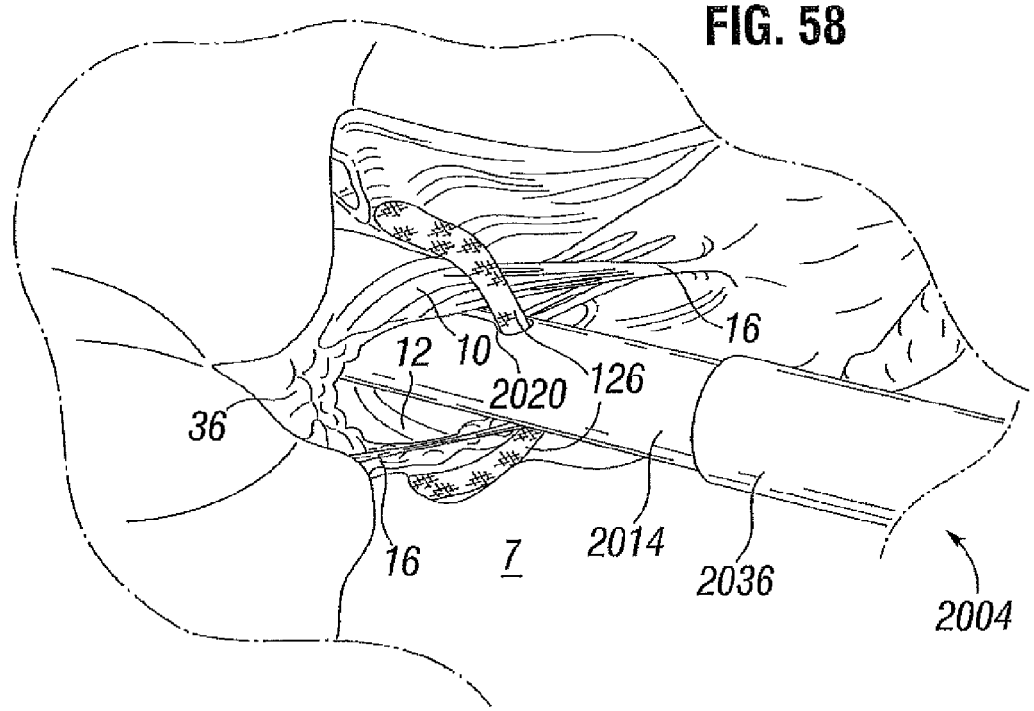
FIG. 58 is a view of the mitral valve region of the heart from the left ventricle showing the ventricular anchors extending from the slots in the delivery system and showing the ventricular anchors positioned between respective mitral leaflets and the ventricular walls.

In the loaded configuration shown in FIG. 55, the loaded delivery system 2000 can be inserted, nose cone 2030 first, through heart apex 38 into the left ventricle 6 and positioned near the mitral valve region for deployment. An introducer sheath (not shown) can be initially inserted through an incision in the heart to provide a port for introducing the delivery system 2000 into the heart. In addition, the delivery system 2000 can be advanced over a conventional guide wire (not shown) that is advanced into the heart ahead of the delivery system 2000. The grip 2052 can then be moved proximally relative to the rest of the delivery system to retract the outer sheath 2036 relative to the inner sheath 2014 and allow the ventricular anchors 126 to spring outwardly away from the inner sheath 2014, as shown in FIGS. 56 and 57, such that the ventricular anchors extend through the rounded proximal end portion 2020 of the slots 2028. The delivery system desirably is oriented rotationally such that each ventricular anchor 126 is positioned between sets of chordate tendineae 16 attached to one of the native mitral valve leaflets 10, 12. Next, the delivery system 2000 can be advanced atrially such that the nose cone 2030 enters the native mitral valve orifice and the protruding ventricular anchors 126 move between respective leaflets 10, 12 and the ventricular walls 20, as shown in FIG. 58. Then, while holding a housing 2054 of the delivery system 2000 steady, the physician can rotate the knob 2062 of the rotatable sleeve 2060 relative to the housing to retract the inner sheath 2014 proximally. The pusher tip 2018 remains stationary while the inner sheath 2014 retracts, thereby leaving the compressed prosthetic valve 100 in the same axial location as it is uncovered and deployed from the inner sheath 2014. Alternatively, the inner sheath 2014 can be held stationary while the pusher tip 2060 is moved distally to push the valve 100 out of the inner sheath 2014. While the inner sheath 2014 is being retracted relative to the pusher tip 2018, the pusher tip can exert an axial force in the distal direction upon the proximal, or lowermost, surface of the prosthetic valve 100. In embodiments of the prosthetic valve having a pusher member 204, the pusher member 204 can direct this axial force directly to the main body 122 and prevent direct contact between the pusher tip 2018 and the ventricular anchor 126 to reduce the risk of damage to the ventricular anchors.

When the inner sheath 2014 is retracted relative to the prosthetic valve 100, the distal, or upper, portion of the prosthetic valve comprising the downwardly folded atrial sealing member 124 is uncovered first. With reference to FIGS. 59 and 60, when the inner sheath 2014 has been retracted beyond the outer rim of the atrial sealing member 124 of the prosthetic valve 100, the atrial sealing member can spring radially outward away from the main body 122, pivoting about the distal end of the main body.

Figure 62:
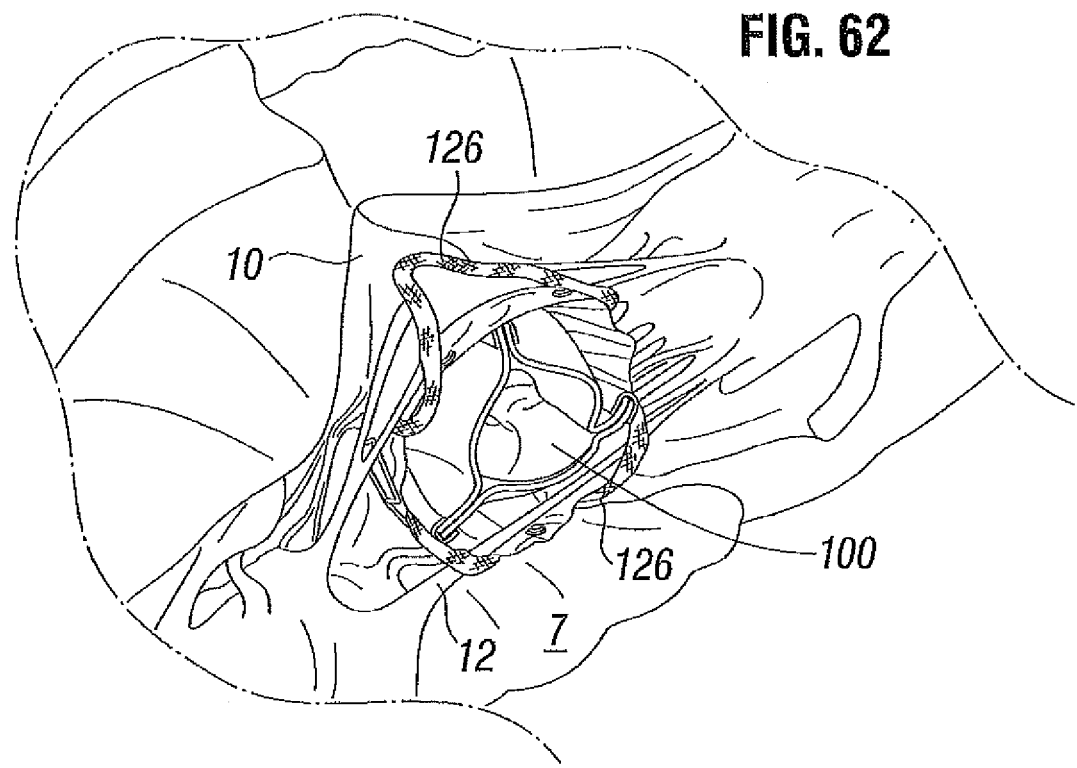
FIG. 62 is a view of the mitral valve region of the heart from the left ventricle showing an exemplary embodiment of a prosthetic valve fully implanted with the mitral leaflets captured between a main body and ventricular anchors.

As the inner sheath 2014 is retracted relative to the prosthetic valve 100, the end portions of the ventricular anchors 126 passing through the rounded proximal end portion 2020 of the slots 2028 are forced through the narrower distal portions of the slots 2028 toward the retaining band 2022, as shown in FIGS. 59 and 60. The end portions of the ventricular anchors are initially side-by-side in the wider proximal end portion 2020 of the slot. When forced into the narrower portion of a slot 2028, the two end portions of each ventricular anchor 126 can be radially overlapping, or oriented one on top of the other, as opposed to side-by-side. In other embodiments, the slots 2028 can be wider such that the two end portions of the ventricular anchor 126 can move about the slots 2028 side-by-side. As the ventricular anchor 126 moves toward the distal end of a slot 2028, the ventricular anchor can contact the notch 2026 in the retaining band 2022, as shown in FIG. 60, and can cut the band 2022 or otherwise cause the band to tear or split apart at the notched location, as shown in FIG. 61. When the inner sheath 2014 is retracted beyond the proximal, or lower, end of the prosthetic valve 100, the compressed body of the prosthetic valve can resiliently self-expand to the expanded state, as shown in FIG. 61. As the prosthetic valve expands, the gaps between the ventricular anchors 126 and the outer surface of the main body 122 decreases, capturing the leaflets 10, 12 between the ventricular anchors 126 and the main body 122, as shown in FIGS. 23 and 62. The expansion of the main body 122 of the prosthetic valve 100 can force open the native mitral leaflets 10, 12, holding the native mitral valve 2 in an open position. The prosthetic valve 100 can then replace the functionality of the native mitral valve 2. After the prosthetic valve 100 is expanded, the inner shaft 2006 of the delivery system can be retracted, pulling the nose cone 2030 back through the prosthetic valve, and the whole delivery system 2000 can be retracted out of the body.

In some embodiments, the delivery system 2000 can be guided in and/or out of the body using a guide wire (not shown). The guide wire can be inserted into the heart and through the native mitral orifice, and then a proximal end of the guidewire can be threaded through the lumen 2008 of the inner shaft 2006. The delivery system 2000 can then be inserted through the body using the guidewire to direct the path of the delivery system.

Atrial Approaches

The prosthetic valve 100 can alternatively be delivered to the native mitral valve region from the left atrium 4. Referring to FIGS. 63-67, one approach for delivering the prosthetic valve from the atrial side of the mitral valve region utilizes a delivery catheter 2100. The prosthetic valve 100 is first crimped from the expanded state to the radially compressed state and loaded into a primary sheath 2102, and optionally also a secondary sheath, at the distal end portion of the delivery catheter 2100, as shown in FIG. 63. The delivery catheter 2100 is used to guide the prosthetic valve 100 through the body and into the left atrium 4. The prosthetic valve 100 is oriented within the sheath 2102 such that the outflow end 112 of the prosthetic valve 100 (the end supporting the ventricular anchors 126) is closest to the distal end of the sheath and thus enters the left atrium 4 first and the inflow end 110 (the atrial sealing member 124) of the prosthetic valve enters last. The sheath 2102 can then be inserted into the left atrium 4 in various manners, one example being the transatrial approach shown in FIG. 66, and another example being the transeptal approach shown in FIG. 67. When the delivery catheter 2100 is used to access the heart via the patient's vasculature, such as shown in FIG. 67, the catheter 2100 can comprise a flexible, steerable catheter.

Once in the left atrium 4, the distal end 2104 of the primary sheath 2102 can be moved across the mitral annulus 8 such that the ventricular anchors 126 are positioned beyond the mitral leaflets 10, 12 prior to deploying the ventricular anchors from the sheath.

The prosthetic valve 100 can then be partially expelled from of the distal end 2104 of the primary sheath 2102 using a rigid pusher shaft 2106 (see FIG. 64) that is positioned within the sheath 2102 and can slide axially relative to the sheath. When the sheath 2102 is retracted proximally relative to the pusher shaft 2106 and the prosthetic valve 100, the pusher shaft 2106 urges the prosthetic valve distally out of the sheath 2102, as shown in FIG. 64. Alternatively, the pusher shaft 2106 can be moved distally while the sheath 2102 is held in place, thereby pushing the prosthetic valve 100 distally out of the sheath.

Figure 68:
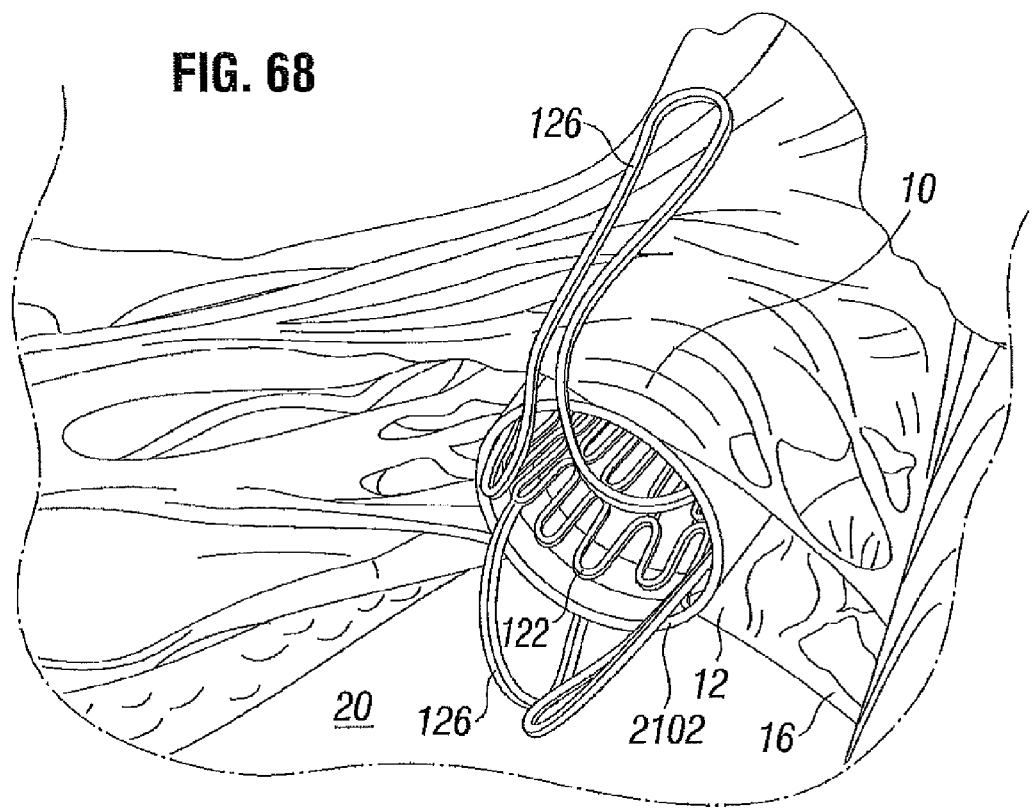
FIG. 68 is a view of the mitral valve region from the left ventricle showing an embodiment of an atrially delivered prosthetic valve having ventricular anchors extending free of a sheath and positioned between the native mitral valve leaflets and the ventricular walls.

When the primary sheath 2102 is inserted across the mitral annulus 8 and past the lower ends of the leaflets 10, 12, the prosthetic valve 100 can be partially expelled to free the ventricular anchors 126, as shown in FIG. 64. The freed ventricular anchors 126 can spring outwardly when they are freed from the sheath 2102. Optionally, the sheath 2102 can then be slid back over the exposed portion of the main body 122, such that only the ventricular anchors are showing, as shown in FIG. 65. To accomplish this step, the atrial end of the frame can comprise features (not shown), such as mechanical locking features, for releasably attaching the prosthetic valve 100 to the pusher shaft 2106, such that the pusher shaft can pull the prosthetic valve back into the sheath 2102. The sheath 2102 and the prosthetic valve 100 are then retracted atrially, proximally, such that the outwardly protruding ventricular anchors 126 move between respective leaflets 10, 12, and the ventricular walls 20, as shown in FIGS. 66-68. In other embodiments, such as those shown in FIGS. 44 and 45, the ventricular anchors can elastically deflect upward or bend around respective leaflets 10, 12 when the ventricular anchors are freed from the sheath 2102.

Optionally, the delivery catheter 2100 can also include a secondary sheath (not shown) within the outer sheath 2102 and can contain the pusher shaft 2106, the atrial sealing member 124 and the main body 122 of the frame, but not the anchors 126. In the position shown in FIG. 63, the distal end of the secondary sheath can be positioned between the anchors 126 and the main body 122. As the outer primary sheath 2102 is retracted, as in FIG. 64, the secondary sheath can remain in a position compressing the main body 122 of the frame while the anchors 126 are freed to extend outward. Because the secondary sheath remains covering and compressing the main body 122, there is no need recover the main body with the primary sheath 2102, as in FIG. 65. Instead, the prosthetic valve 100 is moved proximally by moving the secondary sheath and pusher shaft proximally in unison. Then, to expel the prosthetic valve 100 from the secondary sheath, the secondary sheath is retracted proximally relative to the pusher shaft 2106.

Figure 69:
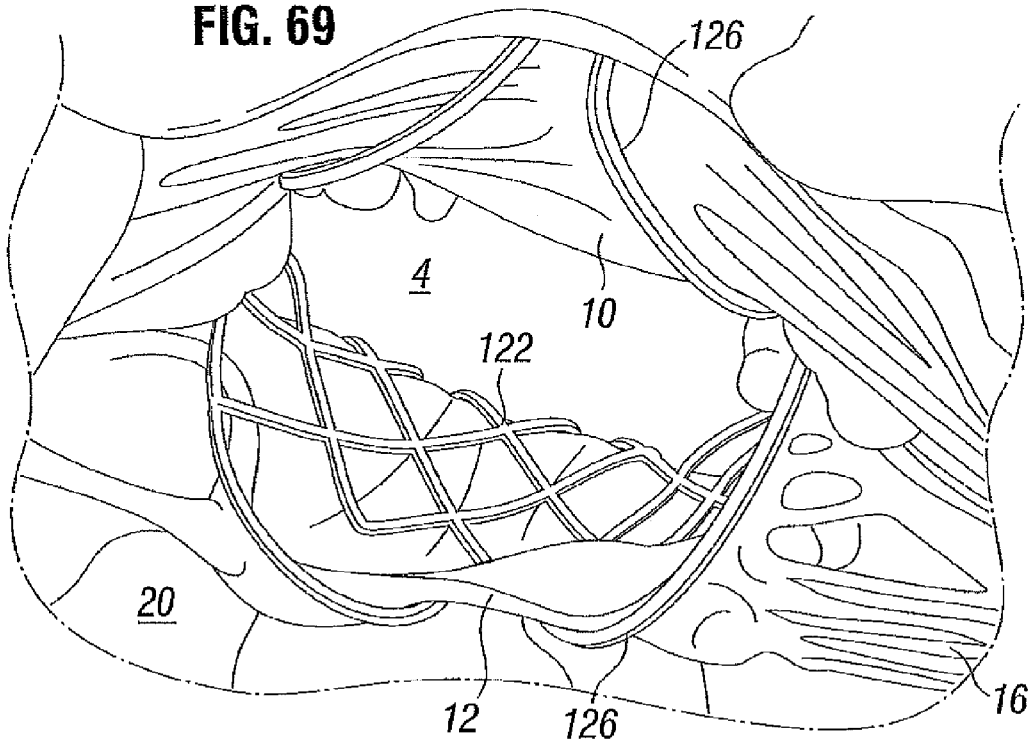
FIG. 69 is a view of the mitral valve region from the left ventricle showing the prosthetic valve of FIG. 68 fully expanded and anchored to the native mitral valve leaflets.

After the ventricular anchors 126 are positioned behind the leaflets 10, 12 and the remaining portion of the prosthetic valve 100 is expelled from the primary sheath 2102, the prosthetic valve 100 can expand to its functional size, as shown in FIGS. 62 and 69, thereby capturing the leaflets 10, 12 between the ventricular anchors 126 and the main body 122. Once the prosthetic valve 100 is implanted, the delivery catheter 2100 can be retracted back out of the body.

In alternative prosthetic valve embodiments, the main body and the atrial sealing member of the frame can be plastically expandable and can be expanded by a balloon of a balloon catheter (not shown) when the prosthetic valve is positioned at the desired location. The ventricular anchors in such an embodiment can exhibit a desired amount of elasticity to assist in positioning the leaflets 10, 12 between the ventricular anchors and the main body during deployment. Once the prosthetic valve is fully expanded, the balloon can be retracted through the expanded prosthetic valve and out of the body.

Mitral Regurgitation Reduction

Mitral regurgitation (MR) occurs when the native mitral valve fails to close properly and blood flows into the left atrium from the left ventricle during the systole phase of heart contraction. MR is the most common form of valvular heart disease. MR has different causes, such as leaflet prolapse, dysfunctional papillary muscles and/or stretching of the mitral valve annulus resulting from dilation of the left ventricle. MR at a central portion of the leaflets can be referred to as central jet MR and MR nearer to one commissure of the leaflets can be referred to as eccentric jet MR.

Rather than completely replacing the native mitral valve, another way to treat MR is by positioning a prosthetic spacer between the leaflets that decreases the regurgitant orifice area, allowing the mitral valve to function with little or no regurgitation, while minimizing impact to the native valve and left ventricle function and to the surrounding tissue. Additional information regarding treatment of MR can be found in U.S. Pat. No. 7,704,277 and U.S. Publication No. 2006/0241745 A1, both of which are incorporated by reference herein.

Figure 71:
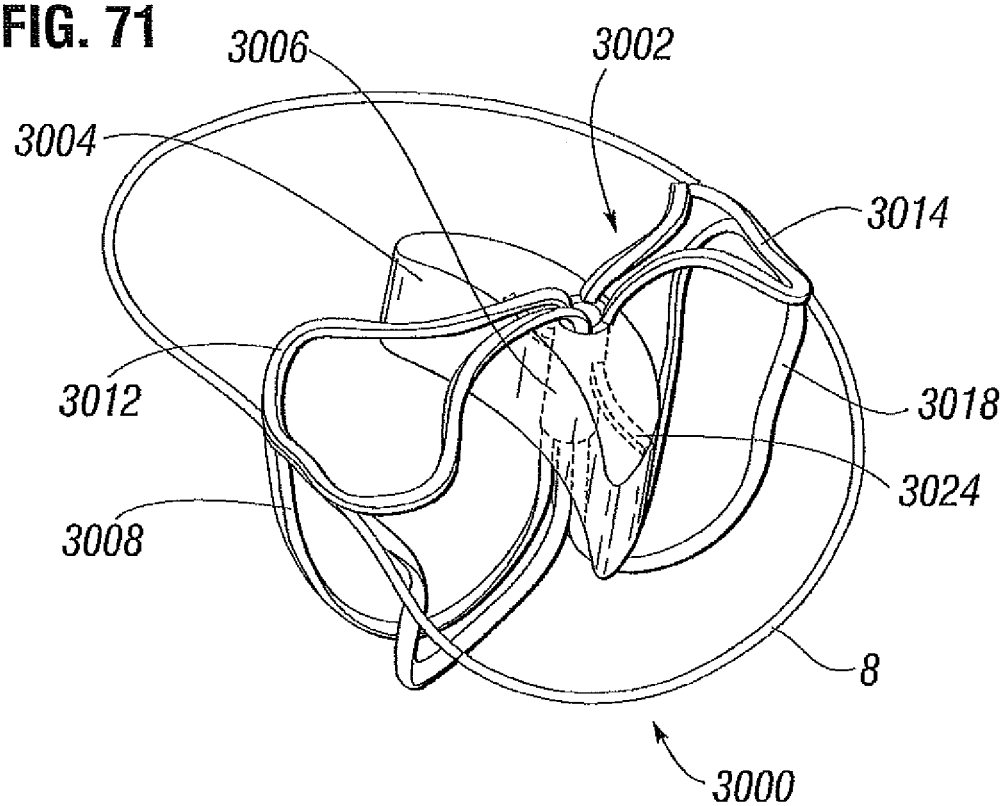
FIG. 71 a perspective view of an embodiment of a prosthetic apparatus for implanting at the native mitral valve region to treat mitral regurgitation.
Figure 72:
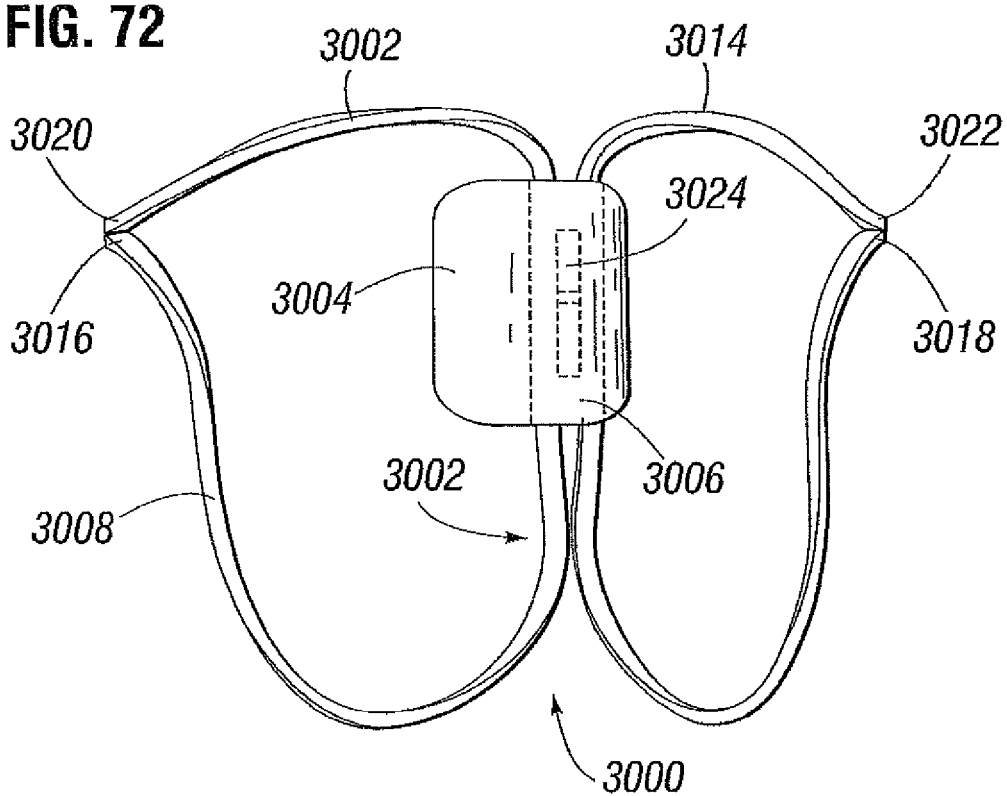
FIG. 72 is a side view of the prosthetic apparatus of FIG. 71.
Figure 73:
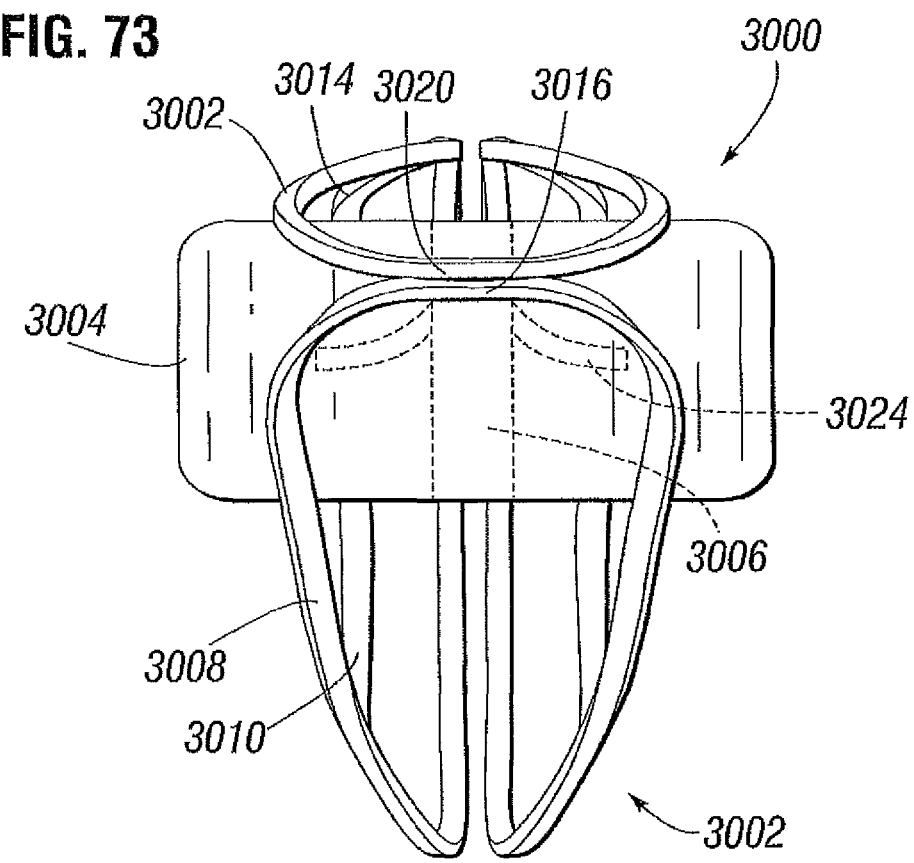
FIG. 73 is another side view of the prosthetic apparatus of FIG. 71.

FIG. 71 shows an exemplary prosthetic spacer embodiment 3000 with which a spacer, or other body, can be suspended or "floated" between the leaflets using anchoring concepts described herein. The prosthetic spacer 3000 can comprise a frame 3002 and spacer body 3004. The spacer body 3004 can comprise polyurethane, foam, and/or other suitable material(s) and can optionally be coated with Teflon and/or other suitable material(s). The spacer body 3004 can comprise a crescent shape that conforms to the crescent shaped juncture between the anterior leaflet 10 and the posterior leaflet 12 (see FIGS. 4A and 4B), or the spacer body can comprise other suitable shapes, such as an ellipse, circle, hourglass, etc. Depending on the shape of the spacer body 3004 and the positioning of the spacer body relative to the native structure, embodiments of the prosthetic spacer 3000 can help treat central jet MR, eccentric jet MR, or both.

Furthermore, the spacer body 3004 can comprise a minimal transverse cross-sectional area and tapered edges. This shape can reduce diastolic forces from blood flowing through the mitral valve from the left atrium to the left ventricle. This shape can also reduce systolic forces on the spacer body 3004 when the native valve is closed around the spacer body and naturally place a larger portion of the systolic forces on the native leaflets and chordae. The shape of the spacer body 3004 can therefore reduce the forces transferred to the native valve tissue at anchor engagement locations, which can reduce the likelihood of perforation and erosion at the engagement locations and rupture of the native chordae that support the leaflets. The overall minimal size of the prosthetic spacer 3000 can further provide an opportunity to decrease the required cross-sectional size of a delivery system, allowing for delivery via narrower vasculature and/or less invasive incisions in the body and heart.

The frame 3002 can be made of a strong, flexible material, such as Nitinol. As shown in FIG. 71, the frame 3002 can comprise a frame body 3006, an anterior ventricular anchor 3008, a posterior ventricular anchor 3010, an anterior atrial anchor 3012 and a posterior atrial anchor 3014. The frame body 3006 can comprise a generally longitudinal column extending through the spacer body 3004. Various embodiments of the frame body 3006 are described in detail below.

The frame 3002 can further comprise one or more spacer expanders 3024 extending laterally from the frame body 3006 through the spacer body 3004. The expanders 3024 can resiliently expand away from the frame body and assist in the expansion of the spacer body 3004 during deployment. In some embodiments, the spacer expanders 3024 can be rectangular cut-out portions of a cylindrical frame body 3006, as shown in FIG. 71, that are bent radially away from the frame body.

The anterior ventricular anchor 3008 is configured to extend from the ventricular end of the frame body 3006, around the A2 edge of the anterior leaflet 10 and extend upward behind the leaflet to a location on the ventricular surface of the mitral annulus 8 and/or the annulus connection portion of the anterior leaflet, while the anterior atrial anchor 3012 is configured to extend radially from the atrial end of the frame body 3006 to a location on the atrial surface of the mitral annulus 8 opposite the anterior ventricular anchor 3008. Similarly, the posterior ventricular anchor 3010 is configured to extend from the ventricular end of the frame body 3006, around the P2 edge of the posterior leaflet 12 and extend upward behind the leaflet to a location on the ventricular surface of the mitral annulus 8 and/or the annulus connection portion of the posterior leaflet, while the posterior atrial anchor 3014 is configured to extend radially from the atrial end of the frame body 3006 to a location on the atrial surface of the mitral annulus 8 opposite the posterior ventricular anchor 3010.

The ventricular anchors 3008, 3010 and the atrial anchors 3012, 3014 can comprise broad engagement portions 3016, 3018, 3020 and 3022, respectively, that can be configured to compress the mitral annulus 8 and/or annulus connection portions of the leaflets 10, 12 to retain the prosthetic spacer 3000 from movement in both the atrial and ventricular directions. The broad engagement portions can provide a greater area of contact between the anchors and the native tissue to distribute the load and reduce the likelihood of damaging the native tissue, such as perforation or erosion at the engagement location. The ventricular anchors 3008, 3010 in the illustrated configuration loop around the native leaflets 10, 12 and do not compress the native leaflets against the outer surface of the spacer body 3004, allowing the native leaflets to naturally open and close around the spacer body 3004.

Figure 74:
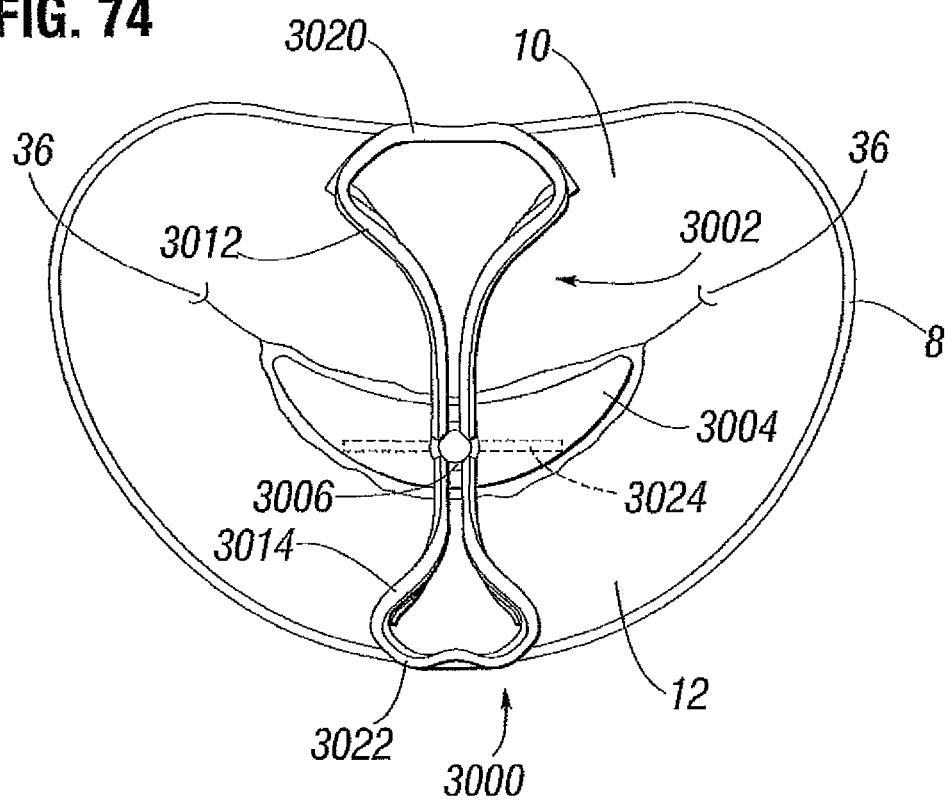
FIG. 74 is an end view of the prosthetic apparatus of FIG. 71.

As shown in FIG. 74, the mitral annulus 8 is generally kidney shaped such that the anterior-posterior dimension is referred to as the minor dimension of the annulus. Because the prosthetic spacer 3000 can anchor at the anterior and posterior regions of the native mitral valve 2, the prosthetic spacer can be sized according to the minor dimension of the annulus 8. Echo and CT measuring of the minor dimension of the mitral annulus 8 are exemplary methods of sizing the prosthetic spacer 3000.

Figure 75:
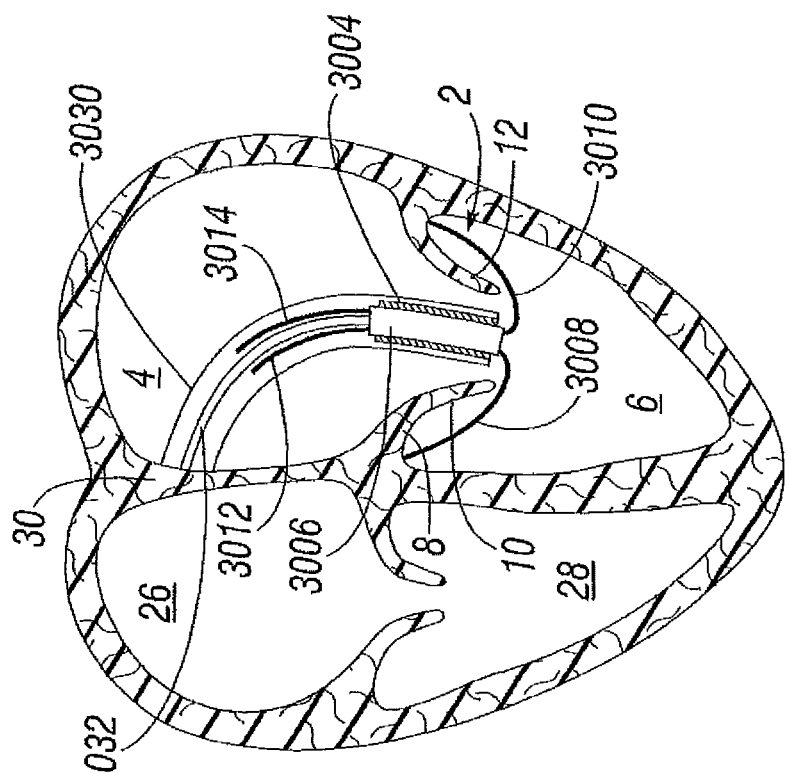
FIGS. 75-79 are cross-sectional views of the heart showing a transeptal delivery of the prosthetic apparatus of FIG. 71.

FIGS. 75-79 illustrate an exemplary method for delivering the prosthetic spacer 3000 to the native mitral valve region of the heart. The prosthetic spacer 3000 can be delivered into the heart using a delivery system comprising an outer sheath 3030 and inner torque shaft 3032. The prosthetic spacer 3000 is compressed and loaded into a distal end of the outer sheath 3030 with the atrial anchors 3012, 3014 loaded first. As shown in FIG. 75, the atrial anchors are resiliently extended proximally and the ventricular anchors 3008, 3010 are resiliently extended distally such that the prosthetic spacer 3000 assumes a sufficiently narrow cross-sectional area to fit within the lumen of the outer sheath 3030. Within the outer sheath 3030, the prosthetic spacer 3000 is positioned such that the atrial end of the frame body 3006 abuts the distal end of the torque shaft 3032, the atrial anchors 3012, 3014 are between the torque shaft and the inner wall of the outer shaft, the compressed spacer 3004 abuts the inner wall of the outer sheath, and the distal ends of the ventricular anchors 3008, 3010 are adjacent to the distal opening of the outer sheath. The torque shaft 3032 can be releasably coupled to the atrial end of the prosthetic spacer 3000, such as at the proximal end of the frame body 3006.

Once loaded, the delivery system can be introduced into the left atrium 4, such as via the atrial septum 30, and the distal end of the outer sheath 3030 can be passed through the native mitral valve 2 and into the left ventricle 6, as shown in FIG. 75.

Figure 76:
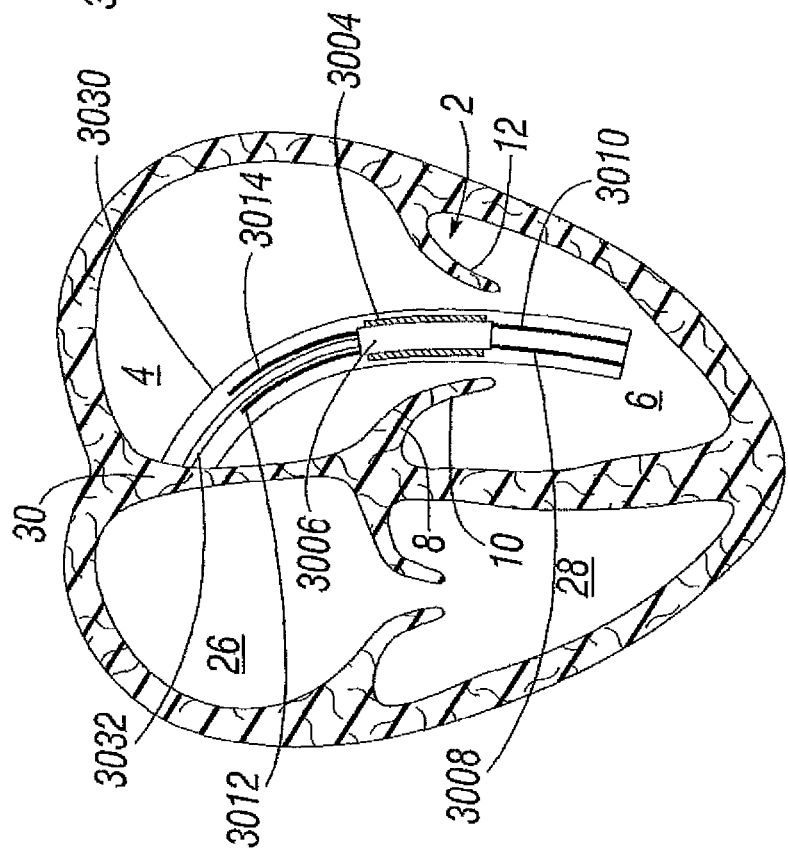

Next, the outer sheath 3030 can be retracted relative to the torque shaft 3032 to expel the ventricular anchors 3008, 3010 from the distal opening of the outer sheath. At this point, the torque shaft 3032 can be rotated to rotate the prosthetic spacer 3000 within the outer sheath 3030 (or optionally, the torque shaft and the outer sheath can both be rotated) as needed to align the ventricular anchors with the A2/P2 aspects of the native valve 2. The releasable attachment between the torque shaft 3032 and the prosthetic spacer 3000 can be sufficient to transfer torque from the torque shaft to the prosthetic in order to rotate the prosthetic as needed. The ventricular anchors 3008, 3010 can be pre-formed such that, as they are gradually expelled from the outer sheath 3030, they begin to curl apart from each other and around the A2/P2 regions of the leaflets. This curling movement can be desirable to avoid entanglement with the ventricular walls. When the outer sheath 3030 is retracted to the ventricular end of the frame body 3006, as shown in FIG. 76, the ventricular anchors 3008, 3010 are fully expelled from the outer sheath and positioned behind the leaflets. The entire delivery system and prosthetic can them be moved proximally until the engagement portions 3016, 3018 of the ventricular anchors abut the ventricular side of the mitral annulus 8 and/or the annulus connection portions of the leaflets 10, 12.

Figure 77:
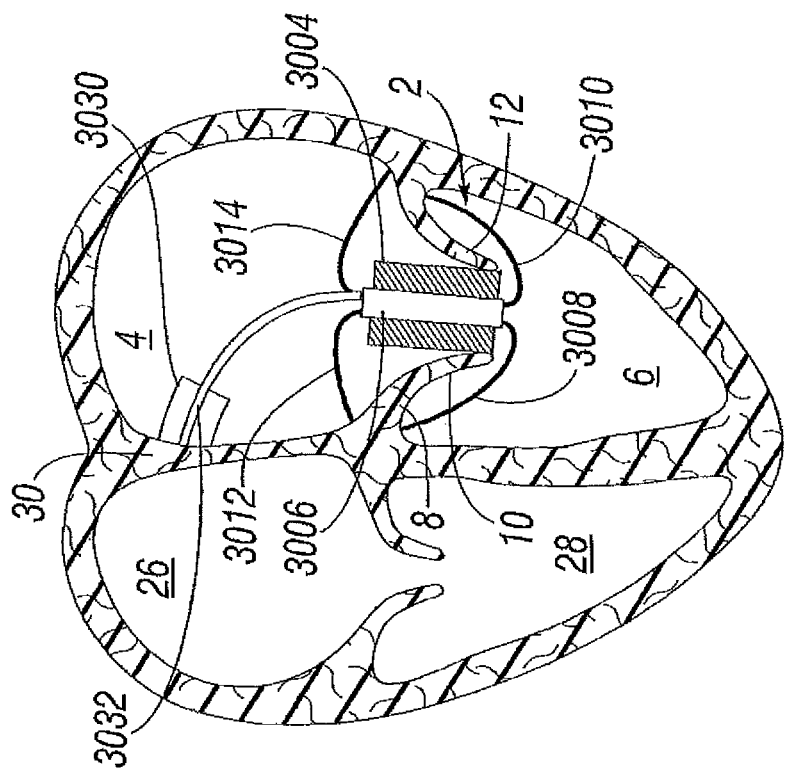

Next, the outer sheath 3030 can be further retracted to relative to the torque shaft 3032 such that the distal end of the outer sheath is even with the atrial end of the frame body 3006, as shown in FIG. 77, which allows the compressed spacer expanders 3024 and the compressed spacer body, or other body, 3004 to resiliently self-expand radially outward to the fully expanded, functional state. Note that the spacer body 3004 expands mostly in a direction perpendicular to the minor dimension of the annulus, or toward the commissures 36 (see FIG. 74). In some embodiments, the spacer body 3004 can unfold or unfurl from the compressed state to the expanded state and in some embodiments the spacer body can be inflated, such as with saline or with an epoxy that hardens over time.

Once the spacer body is expanded within the valve, as shown in FIG. 77, hemodynamic evaluation of the spacer can be performed to assess the effectiveness of the prosthetic spacer 3000 in reducing MR. Depending on the result of the evaluation, deployment can continue or the prosthetic spacer 3000 can be recovered, retracted and/or repositioned for deployment.

From the position shown in FIG. 77, the outer sheath 3030 can be advanced back over the spacer body 3004 (by advancing the outer sheath 3030 relative to the torque shaft 3032), causing the spacer body to re-compress, as shown in FIG. 76. In some embodiments, the ventricular anchors are not recoverable, though in some embodiments the ventricular anchors can be sufficiently pliable to be re-straightened and recovered, in which case then entire delivery process can be reversed and restarted. From the position shown in FIG. 76, the delivery system can be repositioned and the spacer body 3004 can be redeployed and reassessed.

Figure 78:
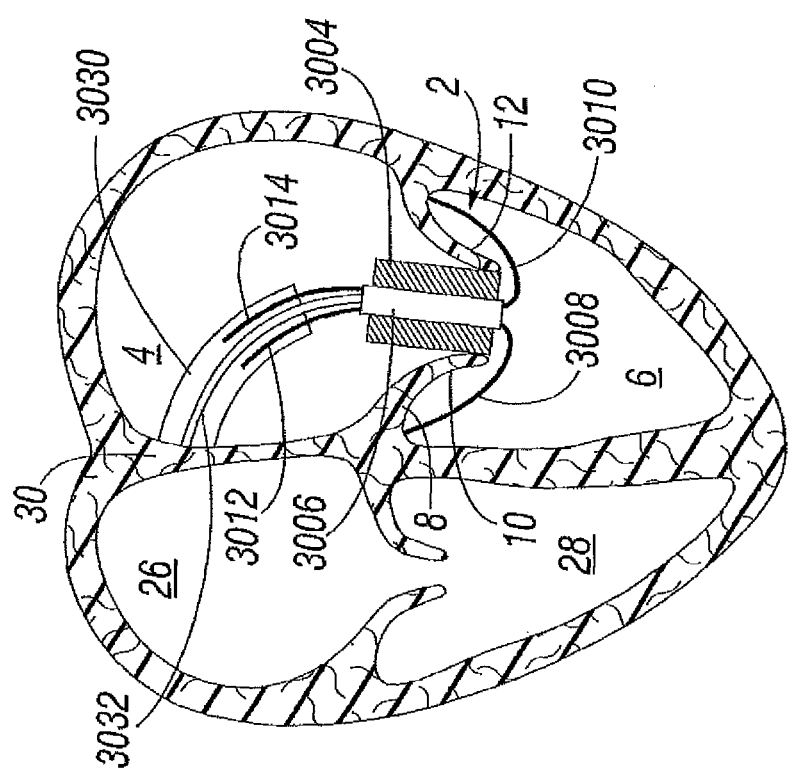

Once the ventricular anchors 3008, 3010 and the spacer body 3004 are acceptably deployed, the outer sheath 3030 can be further retracted relative to the prosthetic spacer 3000 and the torque shaft 3032 to expel the atrial anchors 3012, 3014 from the outer sheath, as shown in FIG. 78. Once fully expelled, the atrial anchors resiliently curl into their final deployment position shown in FIG. 78 with their engagement portions 3020, 3022 pressed against the atrial side of the annulus 8 and/or the annulus connection portions of the leaflets 10, 12 opposite the engagement portions 3016, 3018, respectively, of the ventricular anchors, thereby compressing the annulus and/or the annulus connection portions of the leaflets at the A2 and P2 regions to retain the prosthetic spacer 3000 within the native mitral valve region 2.

Figure 79:
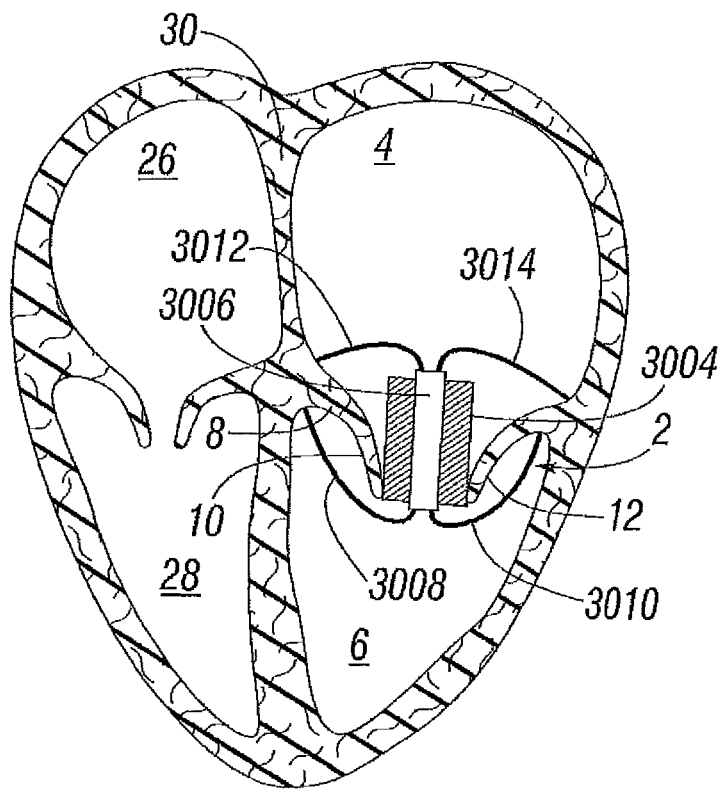

Once the atrial anchors 3012, 3014 are deployed, the torque shaft 3032 can be released from the atrial end of the frame body 3006. The delivery system can then be retracted back out of the body, leaving the prosthetic spacer 3000 implanted, as shown in FIG. 79.

Figure 80:
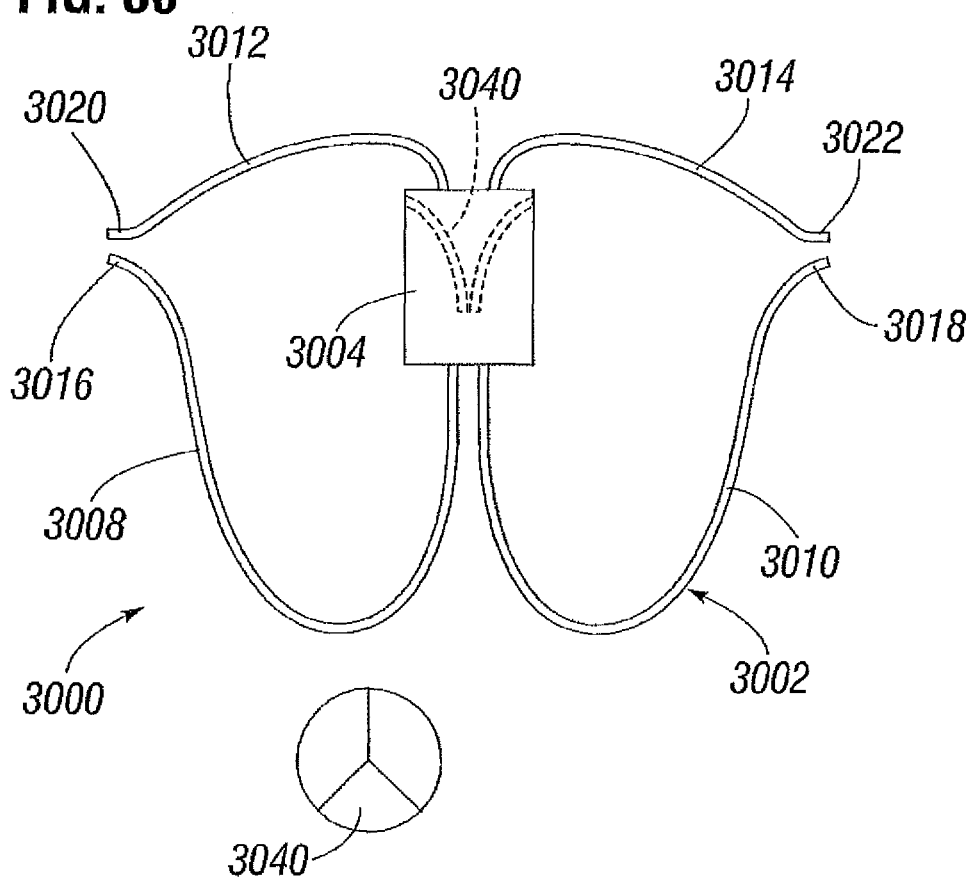
FIG. 80 is a side view of an alternative embodiment of a prosthetic apparatus of FIG. 71, comprising prosthetic valve.
Figure 82:
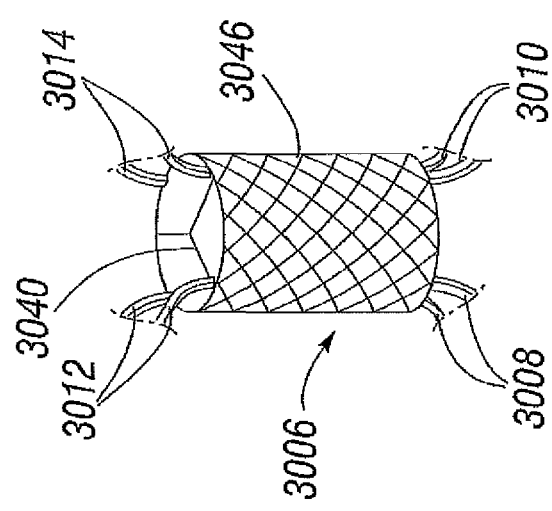
FIG. 82 is a partial side view of an alternative embodiment of a prosthetic apparatus of FIG. 71, comprising a lattice frame body and a prosthetic valve.

In some embodiments, the spacer body 3004 can comprise a valve structure 3040, such the embodiments shown in FIGS. 80 and 82. The valve structure 3040 can function in conjunction with the native mitral valve 2 to regulate blood flow between the left atrium 4 and the left ventricle 6. For example, the valve structure 3040 can be positioned between the native leaflets such that the native leaflets close around the outside of the valve structure such that some blood flows through the valve structure while other blood flows between the outside of the valve structure and the native leaflets. The valve structure 3040 can comprise a three-leaflet configuration, such as is described herein with reference to the valve structure 104 and shown in FIGS. 5-7.

In some embodiments, the frame body 3006 can comprise a cylinder, which can optionally comprise solid-walled tube, such as in FIGS. 71-74, a mesh-like wire lattice 3046, such as in FIG. 82, or other cylindrical configurations. With reference to FIGS. 71-75, the frame body 3006 and optionally one or more of the anchors can be formed from a solid-walled tube, such as of Nitinol, wherein the atrial anchors are formed, such as by laser cutting, from one portion of the tube and the ventricular anchors are formed from a second portion of the tube and the frame body is formed from a portion of the tube between the first and second portions. The anchors can then be formed, such as by heat treatment, to a desired implantation configuration. In such embodiments, the anchors and the frame body can be a unibody, or monolithic, structure.

Figure 83:
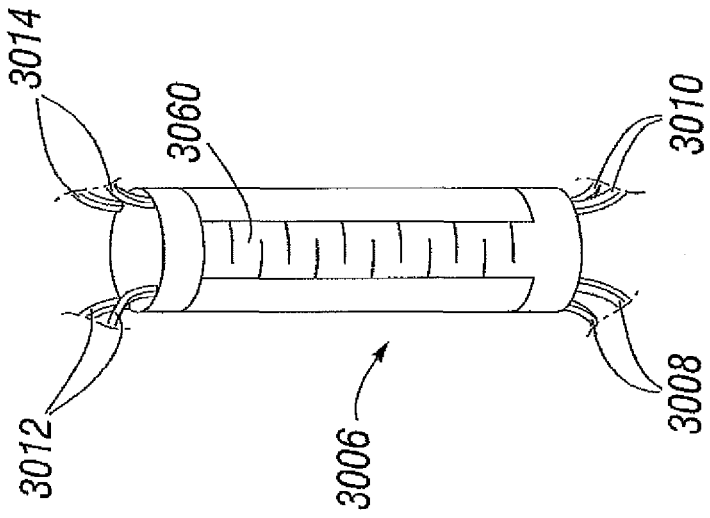
FIG. 83 is a partial side view of an alternative embodiment of a prosthetic apparatus of FIG. 71 comprising a helical frame body.

In other embodiments, the frame body 3006 can comprise a spring-like helically coiled wire column 3050, as shown in FIG. 83. Such a coiled column 3050 can be made from wire having a round or rectangular cross-section and can comprise a resiliently flexible material, such as Nitinol, providing lateral flexibility for conforming to the native valve structure while maintaining longitudinal column stiffness for delivery. In some of these embodiments, the frame body 3006 can comprise a quadrahelical coil of four wires having four atrial ends that extend to form the atrial anchors 3012, 3014 and four ventricular ends that extend to form the four ventricular anchors 3008, 3010.

In other embodiments, the frame body 3006 can comprise a plurality of longitudinal members (not shown). In one such example, the frame body 3006 can comprise four longitudinal members: two longitudinal members that extend to form the anterior anchors 3012, 3014 and two longitudinal members that extend to from the posterior anchors 3008, 3010.

Figure 81:
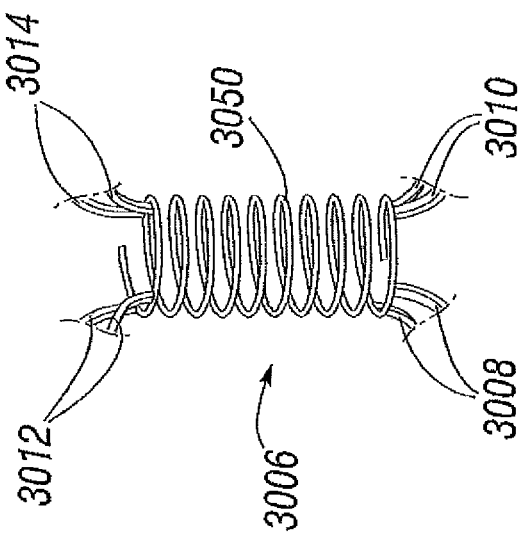
FIG. 81 is a partial side view of an alternative embodiment of a prosthetic apparatus of FIG. 71, comprising a Z-cut frame body.

In other embodiments, the frame body 3006 can comprise a zig-zag cut pattern 3050 along the longitudinal direction of the body, as shown in FIG. 81, that can also provide lateral flexibility while maintaining column strength.

In some embodiments, the prosthetic spacer 3000 can have additional anchors. In some embodiment (not shown), the prosthetic spacer 3000 can have three pairs of anchors: one pair of anchors centered around the posterior leaflet 12, such as the posterior anchors 3010 and 3014 described above, and one pair of anchors at each commissure 36 between the native leaflets 10, 12. These commissure anchors pairs can similarly comprise a ventricular anchor and an atrial anchor and can similarly compress the native annulus 8. In other embodiments, the anterior anchors 3008 and 3012 can also be included as a fourth pair of anchors. Other embodiments can comprise other combinations of these four pairs of anchors and/or additional anchors.

In addition to filling the regurgitant orifice area and blocking blood from flowing toward the left atrium, the prosthetic spacer 3000 can also add tension to the chordae tendinae to prevent further enlargement of the left ventricle and prevent further dilation of the mitral valve annulus.

Anchoring Beneath the Mitral Valve Commissures

Some embodiments of prosthetic devices comprising ventricular anchors, including both prosthetic valves and prosthetic spacers, can be configured such that the ventricular anchors anchor beneath the commissures 36 of the native mitral valve 2 instead of, or in addition to, anchoring behind the A2/P2 regions of the native mitral leaflets 10, 12. FIGS. 84-87 show exemplary prosthetic device embodiments that comprise ventricular anchors that anchor beneath the two commissures 36 of the native mitral valve 2, and related delivery methods. These commissure-anchoring concepts are primarily for use with prosthetic valves, but can be used with other prosthetic devices, including prosthetic spacers.

As shown in FIGS. 3, 4 and 88, the commissures 36 are the areas of the native mitral valve 2 where the anterior leaflet 10 and the posterior leaflet 12 are joined. Portions 39 of the native mitral annulus 8 adjacent to each commissure 36, as shown in FIG. 88, can be relatively thicker and/or stronger than the portions of the mitral annulus 8 adjacent to the intermediate portions of the leaflets A2/P2, providing a rigid, stable location to anchor a prosthetic apparatus. These annulus regions 39 can comprise tough, fibrous tissue that can take a greater load than the native leaflet tissue, and can form a natural concave surface, or cavity.

FIGS. 84 and 85 show an exemplary prosthetic apparatus 4000 being implanted at the native mitral valve region 2 by positioning a ventricular anchor 4002 at one of the cavities 39. The prosthetic apparatus 4000 can be a prosthetic valve having a leaflet structure or a spacer device having a spacer body 3004 for reducing MR. The chordae tendinae 16 attach to the leaflets 10, 12 adjacent to the commissures 36, which can present an obstacle in positioning ventricular anchors in the cavities 39 behind the chordae. It is possible, however, to deliver anchors, such as anchor 4002, around the chordae 16 to reach the cavities 39. Positioning engagement portions, such as the engagement portion 4004, of the ventricular anchors behind the chordae 16 in these natural cavities 39 can be desirable for retaining a prosthetic apparatus at the native mitral valve region 2. However, to avoid entanglement with and/or damage to the native chordae 16, it can be desirable to first guide the engagement portions of the anchors vertically behind the leaflets 10, 12 at the A2/P2 regions, between the chordae 16 from the postero-medial papillary muscle 22 and the chordae 16 from the antero-lateral papillary muscle 24, as shown in FIG. 84, an then move or rotate the engagement portions of the anchors horizontally around behind the chordae 16 toward the commissure cavities 39, as shown in FIG. 85.

In some such methods, the ventricular anchors are first deployed behind the A2/P2 regions of the leaflets and then the entire prosthetic apparatus is rotated or twisted to move the engagement portions of the anchors horizontally toward the cavities 39, as shown in FIGS. 84 and 85. For example, a first anchor deployed behind the anterior leaflet 10 can move toward one of the cavities 39 while a second anchor deployed behind the posterior leaflet 12 can move toward the other cavity 39. This method can also be referred to as a "screw method" because the entire prosthetic is rotated to engage the anchors with the native tissue.

As shown in FIGS. 84 and 85, a prosthetic apparatus 4000 comprising bent, curved, hooked, or generally "L" shaped, anchors 4002 can be used with the screw method. The "L" shaped anchors 4002 can comprise a leg portion 4006 the extends vertically upward from the body of the apparatus 4000, a knee portion 4008, and a foot portion 4010 extending horizontally from the knee portion and terminating in the engagement portion 4004. In some of these embodiments, the "L" shaped anchor 4002 can comprise a looped wire that attaches to the body of the apparatus 4000 at two locations, such that the wire forms a pair of leg portions 4006, a pair of knee portions 4008 and a pair of foot portions 4010. In other embodiments, the anchor 4002 can have other similar shapes, such as a more arced shape, rather than the right angle shape shown in FIG. 84. During delivery into the heart, the foot portion 4010 can be curled or wrapped around the outer surface of the body of the apparatus 4000.

As shown in FIG. 84, in order to move the foot portion 4010 vertically behind the leaflet 10 without entanglement with the chordae, the leg portion 4006 can be positioned slightly off center from the A2 region, closer to the chordae opposite the cavity 39 of desired delivery. As shown in FIG. 84, the leg portion 4006 is positioned to the right such that the foot portion 4010 can pass between the chordae 16.

After the foot portion 4010 clears the chordae 16 and is positioned behind the leaflet, the apparatus 4000 can be rotated to move the engagement portion 4004 horizontally into the cavity 39, as shown in FIG. 85. Note that in FIG. 85 the leg portion 4006 can end up positioned at the A2/P2 region between the chordae 16 to avoid interference with the chordae.

While FIGS. 84 and 85 show a single anchor 4002, both an anterior and a posterior anchor can be delivery in symmetrical manners on opposite sides of the native valve 2, one being anchored at each cavity 39. The feet 4010 of the two anchors 4002 can point in opposite directions, such that the twisting motion shown in FIG. 85 can move them simultaneously to the two cavities 39. During delivery of two anchor embodiments, the two foot portions 4010 can wrap around the outer surface of the body of the apparatus 4000 such that the two foot portions 4010 overlap one another.

In similar embodiments, the anchors 4002 can comprise a paddle shape (see FIG. 37 for example) having two foot portions 4010 extending in opposite directions. While more difficult to move between the chordae, these paddle shaped anchors can allow the apparatus 4000 to be rotated in either direction to engage one of the foot portions 4010 at a cavity 39. In some embodiments, the paddle shaped anchors can be wide enough such that one foot portion 4010 can be positioned at one cavity 39 while the other foot portion is positioned at the other cavity.

Because the anchors 4002 each attach to the body of the apparatus 4000 at two locations, the anchors can spread apart from the main body of the apparatus when the main body is compressed, forming a gap to receive a leaflet, as described in detail above with reference to FIGS. 11-22. In some embodiments, the anchors can separate from the main body when the main body is compressed and either remain separated from the main body, such that the leaflets are not pinched or compressed between the anchors and the main body of the apparatus, or close against the main body during expansion to engage the leaflets. In some embodiments, the main body can move toward the anchors to reduce the gap when then main body expands while maintaining the distance between the foot portions 4010 of the opposing anchors.

Figure 86:
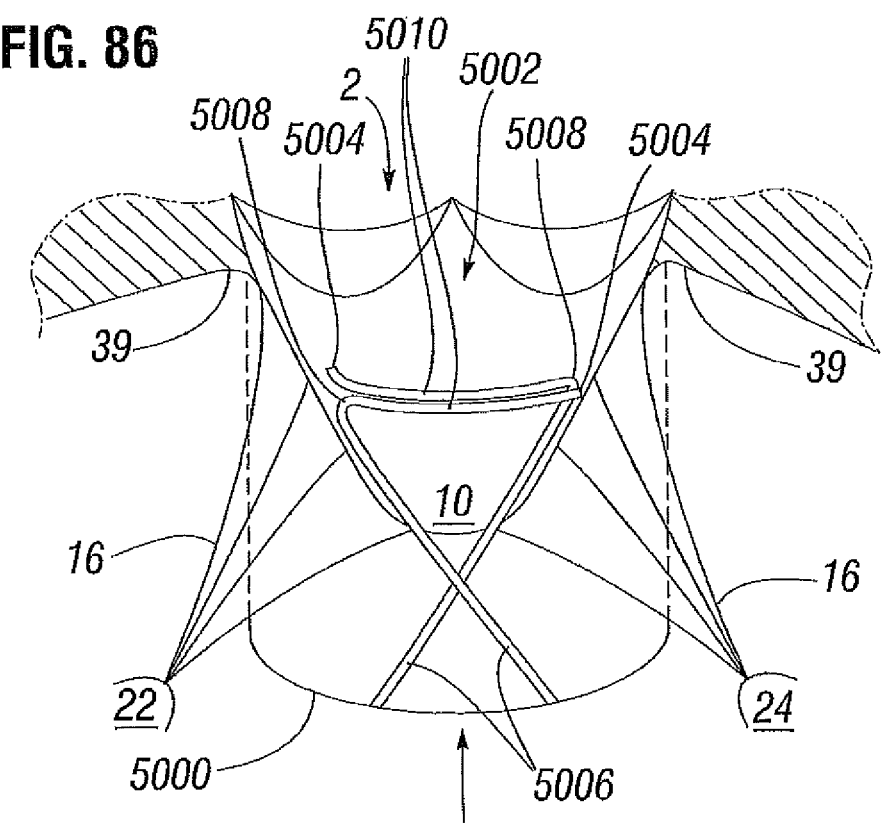
FIGS. 86 and 87 show another exemplary method for implanting another prosthetic apparatus having "L" shaped ventricular anchors.
Figure 87:
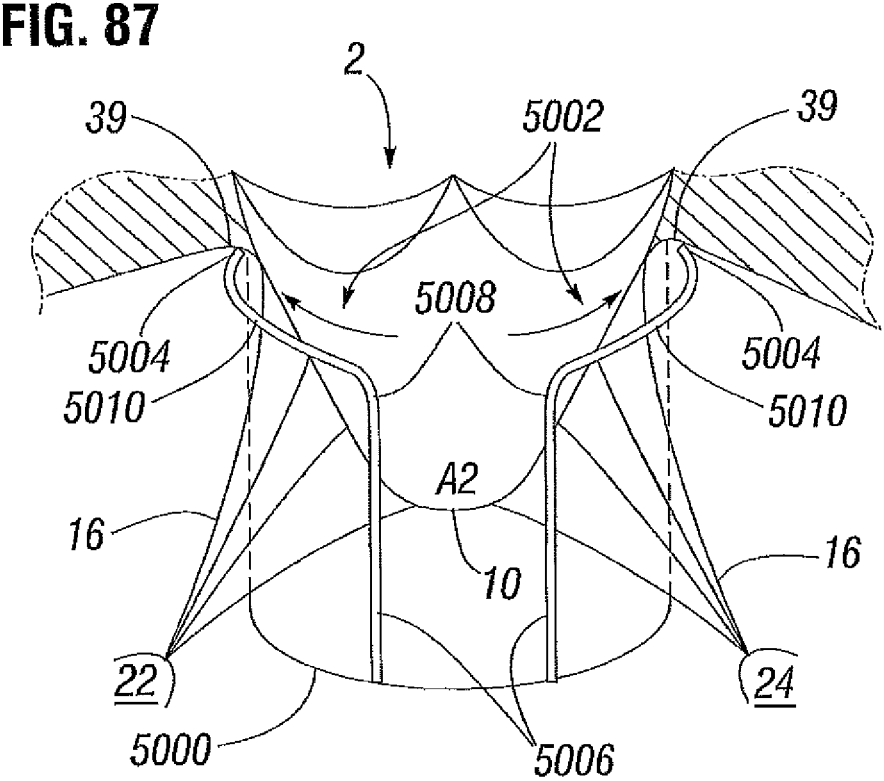

FIGS. 86 and 87 shown another exemplary prosthetic apparatus 5000 being implanted at the native mitral valve region 2 by positioning ventricular anchors 5002 at the cavities 39 and a corresponding method for do so. In this embodiment, the apparatus 5000 can comprise a pair of "L" shaped anchors 5002 on each side (only one pair is visible in FIGS. 86 and 87), with each pair comprising one anchor for positioning in one of the cavities 39 and another anchor for positioning in the other cavity. Each of the anchors can comprise a leg portion 5006 extending vertically from the body of the apparatus 5000 to a knee portion 5008, and a foot portion 5010 extending horizontally from the knee portion 5008 to an engagement portion 5004. In other embodiments, the anchors 5002 can have other similar shapes, such as a more arced shape, rather than the angled shape shown in FIG. 86.

Each pair of anchors 5002 can comprise a resiliently flexible material, such as Nitinol, such that they can be pre-flexed and constrained in a cocked position for delivery behind the leaflets, as shown in FIG. 86, and then released to resiliently spring apart to move the engagement portions 5004 in opposite directions toward the two cavities 39, as shown in FIG. 87. Any suitable constrainment and release mechanisms can be used, such as a releasable mechanical lock mechanism. Once released, one anterior anchor and one posterior anchor can be positioned at one cavity 39 from opposite directions, and a second anterior anchor and a second posterior anchor can be positioned at the other cavity from opposite directions. Some embodiments can include only one anchor on each side of the apparatus 5000 that move in opposite directions toward opposite cavities 39 when released.

Because each pair of anchors 5002 are initially constrained together, as shown in FIG. 86, each pair of anchors can act like a single anchor having two attachment points to the main body of the apparatus 5000. Thus, the anchor pairs can separate, or expand away, from the main body when the main body is compressed and either remain spaced from the main body, such that the leaflets are not pinched or compressed between the anchors and the main body of the apparatus, or close against the main body during expansion to engage the leaflets. In some embodiments, the main body can move toward the anchor pairs to reduce the gap when then main body expands while maintaining the distance between the foot portions 5010 of the opposing anchor pairs.

In the embodiments shown in FIGS. 84-87, the prosthetic apparatus 4000 or 5000 can have a main frame body similar to the embodiments shown in FIG. 5, from which the ventricular anchors 4002, 5002 can extend, and can further comprise one or more atrial anchors, such as an atrial sealing member similar to the atrial sealing member 124 shown in FIG. 5 or a plurality of atrial anchors similar to the atrial anchors 3012 and 3014 shown in FIG. 71, for example. The atrial anchors can extend radially outward from an atrial end of the prosthetic apparatus and contact the native tissue opposite the cavities 39 and thereby compress the tissue between the atrial anchors and the engagement portions 4004, 5004 of the ventricular anchors 4002, 5002 to retain the prosthetic apparatus at the native mitral valve region. The atrial anchors and the ventricular anchors can comprise a broad contact area to distribute the load over a wider area and reduce the likelihood of damaging the native tissue.

In view of the many possible embodiments to which the principles disclosed herein may be applied, it should be recognized that the illustrated embodiments are only preferred examples and should not be taken as limiting the scope of the disclosure. Rather, the scope is defined by the following claims. We therefore claim all that comes within the scope and spirit of these claims.

We claim:

1. A method of implanting a prosthetic heart valve at the native mitral valve region of a heart, the native mitral valve having a native mitral valve orifice and native mitral valve leaflets, the method comprising:
   positioning a docking frame within the native mitral valve orifice such that the docking frame is secured to the native mitral valve leaflets, wherein positioning the docking frame within the native mitral valve orifice comprises positioning a first ventricular anchor behind the anterior native mitral valve leaflet and positioning a second ventricular anchor behind the posterior native mitral valve leaflet; and then
   securing a prosthetic valve within the docking frame.

2. The method of claim 1, wherein positioning the docking frame within the native mitral valve orifice comprises delivering the docking frame into the mitral valve orifice in a radially compressed state and allowing the docking frame to self-expand to a radially expanded state contacting inner surfaces of the native mitral valve leaflets.

3. The method of claim 1, wherein the docking frame comprises an annular main body that comprises a lumen for receiving the prosthetic valve.

4. The method of claim 1, wherein the anterior native mitral valve leaflet is compressed between the first ventricular anchor and an outer surface of a main body of the docking frame, and the posterior native mitral valve leaflet is compressed between the second ventricular anchor and an outer surface of the main body of the docking frame.

5. The method of claim 1, wherein securing a prosthetic valve within the docking frame comprises delivering the prosthetic valve in a radially compressed state into a lumen formed within the docking frame, and allowing the prosthetic valve to self-expand to a radially expanded state contacting inner surfaces of the docking frame.

6. The method of claim 1, wherein securing a prosthetic valve within the docking frame comprises delivering the prosthetic valve in a radially compressed state into a lumen formed within the docking frame, and causing the prosthetic valve to expand to a radially expanded state contacting inner surfaces of the docking frame.

7. The method of claim 1, wherein the prosthetic valve comprises a radially compressible and expandable frame configured to engage with the inside of the docking frame.

8. The method of claim 1, wherein the prosthetic valve is secured within the docking frame via friction.

9. The method of claim 1, wherein the prosthetic valve is secured within the docking frame via a mechanical locking feature.

10. The method of claim 1, wherein the prosthetic valve comprises an atrial anchor that is positioned within the left atrium so as to engage an atrial surface of the native mitral valve when the prosthetic valve is secured within the docking frame.

11. A method of implanting a prosthetic heart valve at the native mitral valve region of a heart, the native mitral valve having a native mitral valve orifice and native mitral valve leaflets, the method comprising:

implanting a radially expandable docking frame within the native mitral valve orifice, the docking frame comprising an annular body defining an inner lumen and ventricular anchors positioned behind the native mitral valve leaflets; and then securing a radially expandable prosthetic valve within the docking frame.

12. The method of claim 11, wherein implanting the docking frame within the native mitral valve orifice comprises delivering the docking frame into the mitral valve orifice in a radially compressed state and allowing the docking frame to self-expand to a radially expanded state contacting inner surfaces of the native mitral valve leaflets.

13. The method of claim 11, wherein implanting the docking frame within the native mitral valve orifice comprises positioning a first ventricular anchor behind the anterior native mitral valve leaflet and positioning a second ventricular anchor behind the posterior native mitral valve leaflet.

14. The method of claim 11, wherein securing a prosthetic valve within the docking frame comprises delivering the prosthetic valve in a radially compressed state into the inner lumen of the annular body of the docking frame, and allowing the prosthetic valve to self-expand to a radially expanded state contacting inner surfaces of the annular body of the docking frame.

15. The method of claim 11, wherein the prosthetic valve comprises a radially compressible and expandable frame configured to engage with the annular body of the docking frame.

* * * * *